(12) United States Patent
Cherpes et al.

(10) Patent No.: US 11,850,279 B2
(45) Date of Patent: *Dec. 26, 2023

(54) PLATFORMS AND METHODS FOR OPTIMIZING HOST ANTIGEN PRESENTATION AND HOST ANTITUMOR AND ANTIPATHOGEN IMMUNITY

(71) Applicant: OHIO STATE INNOVATION FOUNDATION, Columubus, OH (US)

(72) Inventors: Thomas L Cherpes, Columbus, OH (US); Nirk E. Quispe Calla, Hilliard, OH (US); Rodolfo Daniel Vicetti Miguel, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 795 days.

This patent is subject to a terminal disclaimer.

(21) Appl. No.: 16/317,247

(22) PCT Filed: Jul. 13, 2017

(86) PCT No.: PCT/US2017/041948
§ 371 (c)(1),
(2) Date: Jan. 11, 2019

(87) PCT Pub. No.: WO2018/013820
PCT Pub. Date: Jan. 18, 2018

(65) Prior Publication Data
US 2019/0224298 A1     Jul. 25, 2019

Related U.S. Application Data

(60) Provisional application No. 62/444,460, filed on Jan. 10, 2017, provisional application No. 62/361,591, filed on Jul. 13, 2016.

(51) Int. Cl.
| | | |
|---|---|---|
| *A61K 39/395* | (2006.01) | |
| *A61K 39/118* | (2006.01) | |
| *A61K 39/39* | (2006.01) | |
| *C07K 14/535* | (2006.01) | |
| *C07K 16/24* | (2006.01) | |
| *C07K 16/28* | (2006.01) | |
| *C07K 14/475* | (2006.01) | |
| *A61P 37/04* | (2006.01) | |
| *A61P 31/00* | (2006.01) | |
| *A61P 35/00* | (2006.01) | |
| *A61K 39/00* | (2006.01) | |

(52) U.S. Cl.
CPC ............ *A61K 39/118* (2013.01); *A61K 39/39* (2013.01); *A61P 31/00* (2018.01); *A61P 35/00* (2018.01); *A61P 37/04* (2018.01); *C07K 14/475* (2013.01); *C07K 14/535* (2013.01); *C07K 16/248* (2013.01); *C07K 16/2827* (2013.01); *C07K 16/2878* (2013.01); *A61K 2039/5154* (2013.01); *A61K 2039/585* (2013.01); *A61K 2039/892* (2018.08); *C07K 2317/75* (2013.01)

(58) Field of Classification Search
None
See application file for complete search history.

(56) References Cited

U.S. PATENT DOCUMENTS

| | | |
|---|---|---|
| 4,435,386 A | 3/1984 | Ribi et al. |
| 4,436,727 A | 3/1984 | Ribi |
| 4,436,728 A | 3/1984 | Ribi et al. |
| 4,505,899 A | 3/1985 | Ribi et al. |
| 4,505,900 A | 3/1985 | Ribi et al. |
| 4,579,945 A | 4/1986 | Schwartzman |
| 4,866,034 A | 9/1989 | Ribi |
| 5,108,910 A | 4/1992 | Curtis et al. |
| 5,229,496 A | 7/1993 | Deeley et al. |
| 5,554,512 A | 9/1996 | Lyman et al. |
| 6,406,705 B1 | 6/2002 | Davis et al. |
| 7,150,992 B1 | 12/2006 | Lynch et al. |
| 7,488,491 B2 | 2/2009 | Tsuji et al. |
| 7,988,963 B1 | 8/2011 | Banchereau et al. |
| 9,303,247 B2 | 4/2016 | Abe et al. |
| 10,688,171 B2 * | 6/2020 | Cherpes ............... A61K 39/118 |
| 10,835,601 B2 * | 11/2020 | Cherpes ................. A61P 31/12 |
| 2003/0118569 A1 | 6/2003 | Bankert et al. |

(Continued)

FOREIGN PATENT DOCUMENTS

| | | |
|---|---|---|
| CA | 2232865 | 4/1997 |
| EP | 0627487 | 12/1994 |

(Continued)

OTHER PUBLICATIONS

Communication pursuant to Rule 164(1) EPC. Issued by the European Patent Office in Application No. EP 17828469.1 dated Jan. 16, 2020. 19 pages.

Extended European Search Report. Issued by the European Patent Office in Application No. EP 17828469.1 dated Jun. 25, 2020. 14 pages.

Kim, Sung-Whan, et al. "Flt3 ligand induces monocyte proliferation and enhances the function of monocyte-derived dendritic cells in vitro." Journal of Cellular Physiology 230.8 (2015): 1740-1749.

(Continued)

*Primary Examiner* — Yunsoo Kim
(74) *Attorney, Agent, or Firm* — Meuner Carlin & Curfman LLC

(57) ABSTRACT

Disclosed herein are methods and platforms for increasing utility and efficacy of a cellular vaccine. Specifically, disclosed are steps that optimize ex vivo B cell expansion and boost host in vivo immunity. Also disclosed is a platform for enhancing effectiveness of antigen presentation and antigen-specific immune responses. Also disclosed is a method for enhancing effectiveness of APCs in a subject. Also disclosed are vaccines and kits based on the platform.

18 Claims, 30 Drawing Sheets

(56) References Cited

U.S. PATENT DOCUMENTS

| | | | |
|---|---|---|---|
| 2006/0240038 A1* | 10/2006 | Fensterle | A61P 43/00 424/204.1 |
| 2007/0048254 A1 | 3/2007 | Neal et al. | |
| 2009/0075886 A1 | 3/2009 | Brasel et al. | |
| 2010/0028380 A1 | 2/2010 | Kang et al. | |

FOREIGN PATENT DOCUMENTS

| | | |
|---|---|---|
| JP | 2008527051 A | 7/2008 |
| JP | 2011036258 A | 2/2011 |
| WO | 94/28391 | 12/1994 |
| WO | 97/12633 | 4/1997 |
| WO | 1999015157 A2 | 4/1999 |
| WO | 0034483 A2 | 6/2000 |
| WO | 2002048167 A1 | 6/2002 |
| WO | 2004007734 A1 | 1/2004 |
| WO | 2007126163 A1 | 11/2007 |
| WO | 2010149394 A1 | 12/2010 |
| WO | 2013/049941 A1 | 4/2013 |
| WO | 2013118899 A1 | 8/2013 |
| WO | 2013/132526 A1 | 9/2013 |
| WO | 2013158819 A2 | 10/2013 |
| WO | 2015016718 A1 | 2/2015 |

OTHER PUBLICATIONS

Massari, Paola, et al. "Toll-like receptor 2-dependent activity of native major outer membrane protein proteosomes of Chlamydia trachomatis." Infection and immunity 81.1 (2013): 303-310.

International Search Report and Written Opinion of the U.S. International Searching Authority. Application No. PCT/US2017/041948, dated Nov. 9, 2017. 14 pages.

Berhanu A, et al., Combinational FLt3 Ligand and Granulocyte Macrophage Colony-Stimulating Factor Treatment Promotes Enhanced Tumor Infiltration by Dendritic Cells and Antitumor CD8+ T-Cell Cross-priming but is Ineffective as a Therapy, Cancer Res, 2006, 66:4895-4903.

Burdin, et al., Immunization with α-galactosylceramide polarizes CD1-reactive NK T cells towards Th2 cytokine synthesis, Eur. J. Immunol., 29:2014 (1999).

Chang DH, et al., Sustained expansion of NKT cells and antigen-specific T cells after injection of α-galactosyl-ceramide loaded mature dendritic cells in cancer patients, J Ex Med, 2005, 201:1503-1517.

Chung, et al, CD1d-restricted T cells license B cells to generate long-lasting cytotoxic antitumor immunity in vivo, Cancer Res, 66:6843 (2006).

Fearon et al., 1998, The complement system and adaptive immunity. Semin. Immunol. 10: 355-61.

Figueroa-Perez, et al., Total synthesis of α-galactosyl cerebroside, Carbohydr. Res., 328:95 (2000).

Fujii S, et al. Prolonged IFN-γ-producing NKT response induced with α-galactosylceramide-loaded DCs, Nat Immunl, 2002, 3:867-874.

Giaccone et al., A phase I study of the natural killer T-cell ligand α-galactosylceramide (KRN7000) in patients with solid tumors, Clin Canc. Res., 8, 3702-3709 (2002).

Godfrey et al., Going both ways: immune regulation via CD1d-dependent NKT cells. J. Clin. Invest., 114:1379-1388 (2004).

Harrison et al., Reduction of recurrent HSV disease using imiquimod alone or combined with a glycoprotein vaccine, Vaccine 19: 1820-1826 (2001).

Hong, et al., The natural killer T-cell ligand alpha-galactosylceramide prevents autoimmune diabetes in non-obese diabetic mice. Nature Med., 7:1052-1056 (2002).

Houston et al., 1988, Protein engineering of antibody binding sites: recovery of specific activity in an anti-digoxin single-chain Fv analogue produced in *Escherichia coli.*, Proc. Natl. Acad. Sci. USA 85:5879-5883.

Kingston et al., The concerted action of GM-CSF and Flt3-ligand on in vivo dendritic cell homeostasis, Jul. 23, 2009; Blood: 114 (4).

Liao G, et al. Glucocorticoid-inducedTNF receptor family-related protein ligand is requisite for optimal functioning of regulatory CD4C T cells, Front Immunol, 2014, 5:35, 7 pages.

Lutz et al., Immature dendritic cells generated with low doses of GM-CSF in the absence of IL-4 are maturation resistant and prolong allograft survival in vivo, Eur. J. Immunol. 2000 30:1813-22.

Miyamoto, et al., A synthetic glycolipid prevents autoimmune encephalomyelitis by inducing TH2 bias of natural killer T cells, Nature, 413:531 (2001).

Moellenauer, et al., Endogenous CD28 expressed on myeloma cells up-regulates interleukin-8 production: implications for multiple myeloma progression, Blood 2001 98:187-193.

Mooney et. al., (1994), Bacterial superantigen signaling via HLA class II on human B lymphocytes, Mol. Immunol. 31: 675-681.

Morita, et al., Structure-activity relationship of. alpha.-Galactosylceramides against B16-bearing mice, J. Med. Chem., 38:2176 (1995).

Morita, et al., Syntheses of α-, β-monoglycosylceramides and four diastereomers of an α-galactosylceramide, Bioorg. Med. Chem. Lett., 5:699 (1995).

Nagar et al., 1998, X-ray crystal structure of C3d: a C3 fragment and ligand for complement receptor 2, Science; 280(5367):1277-81.

Parmiani et al., Opposite immune functions of GM-CSF administered as vaccine adjuvant in cancer patients, Annals of Oncology 18: 226-232, 2007.

Plettenburg, at al., Synthesis of α-Galactosyl Ceramide, a Potent Immunostimulatory Agent, J. Org. Chem., 67:4559 (2002).

Quittet et al., Low doses of GM-CSF (molgramostim) and G-CSF (filgrastim) after cyclophosphamide (4 g/m2) enhance the peripheral blood progenitor cell harvest: results of two randomized studies including 120 patients, Bone Marrow Transplantation (2006) 38, 275-284.

Rosborough BR, et al., Cutting Edge: Flt3 Ligand Mediates STAT3-Independent Expansion but STAT3-Dependent Activation of Myeloid-Derived Suppressor Cells, J Immunol 2014, 192:3470-3473.

Sharif, et al., Activation of natural killer T cells by α-galactosylceramide treatment prevents the onset and recurrence of autoimmune type 1 diabetes, Nature Med., 7:1057 (2001).

Singh, et al., Cutting Edge: Activation of NK T Cells by CD1d and α-Galactosylceramide Directs Conventional T Cells to the Acquisition of a Th2 Phenotype, J. Immunol., 163:2373 (1999).

Takada et al., (1995) Molecular and Structural Requirements of a Lipoteichoic Acid from Enterococcus hirae ATCC 9790 for Cytokine-Inducing, Antitumor, and Antigenic Activities, Infection and Immunity 63: 57-65.

Vasilakos et al., Adjuvant activities of immune response modifier R-848: comparison with CpG ODN. Cellular Immunology 204: 64-74 (2000).

Weigel et al., Comparative analysis of murine marrow-derived dendritic cells generated by Flt3L or GM-CSF/IL-4 and matured with immune stimulatory agents on the in vivo induction of antileukemia responses, Blood, Dec. 1, 2002 vol. 100, No. 12.

Xu et al., Differential Development of Murine Dendritic Cells by GM-CSF versus Flt3 Ligand Has Implications for Inflammation and Trafficking, J. Immunol. Dec. 1, 2007, 179(11).

Yang, at al., The C-glycoside analogue of the immunostimulant α-galactosylceramide (KRN7000): synthesis and striking enhancement of activity, Angew. Chem. Int. Ed., 43:3818-3822 (2004).

Yu, et al., Modulation of CD1d-restricted NKT cell responses by using N-acyl variants of α-galactosylceramides, Proc. Natl. Acad. Sci. USA, 102(9):3383-3388 (2005).

Zhan et al., The inflammatory cytokine, GM-CSF, alters the developmental outcome of murine dendritic cells, Eur. J. Immunol. 2012. 42: 2889-2900.

Office Action issued for Japanese Application No. 2019501578, dated Jun. 22, 2021.

Wennhold, Kerstin, et al. "CD40-activated B cells induce anti-tumor immunity in vivo." Oncotarget 8.17 (2017): 27740.

Office Action issued for Japanese Application No. 2019501578, dated Feb. 8, 2022.

Kim, S.-W., Choi, S.-M., Choo, Y. S., Kim, I.-K., Song, B.-W., & Kim, H.-S. (2015). Flt3 Ligand Induces Monocyte Proliferation and

(56) References Cited

OTHER PUBLICATIONS

Enhances the Function of Monocyte-Derived Dendritic Cells In Vitro. Journal of Cellular Physiology, 230(8), 1740-1749. doi:10.1002/jcp.24824.
Australian Intellectual Property Office. Examination report No. 1. Issued in AU Application No. 2017294751 dated Nov. 8, 2022. 5 pages.
Office Action for Canadian Application No. 3,030,779 dated May 8, 2023.

* cited by examiner

GM-CSF constant at 0.25 µg

FLT3L constant at 2 μg

EG.7-OVA lymphoma (10^6 SQ)

EG.7-OVA lymphoma (1.2x10⁶ SQ)

EG.7-OVA lymphoma (1.2x10^6 SQ)

OVA, whole protein antigen
SIINFEKL, $OVA_{257-264}$ (immunodominant epitope)
α-GC, α-galactosylceramide

PLATFORMS AND METHODS FOR OPTIMIZING HOST ANTIGEN PRESENTATION AND HOST ANTITUMOR AND ANTIPATHOGEN IMMUNITY

CROSS-REFERENCE TO RELATED APPLICATIONS

This application is a national stage application filed under 35 U.S.C. § 371 of PCT/US2017/041948 filed Jul. 13, 2017, which claims benefit of U.S. Provisional Application No. 62/361,591, filed Jul. 13, 2016, and U.S. Provisional Application No. 62/444,460, filed Jan. 10, 2017, which are hereby incorporated herein by reference in their entireties.

BACKGROUND

An antigen-presenting cell (APC) or accessory cell is a cell that displays antigen complexed with major histocompatibility complexes (MHCs) on their surfaces; this process is known as antigen presentation. T cells may recognize these complexes using their T cell receptors (TCRs). APCs process antigens and present them to T cells.

Almost all cell types can serve as some form of APC. They are found in a variety of tissue types. Professional APCs, including macrophages, B cells and dendritic cells, present foreign antigens to CD4$^+$ helper T cells, while other cell types can present antigens originating inside the cell to CD8$^+$ cytotoxic T cells. In addition to the MHC family of proteins, antigen presentation relies on other specialized signaling molecules on the surfaces of both APCs and T cells.

APCs are vital for effective adaptive immune response, as the functioning of both CD8$^+$ cytotoxic and CD4$^+$ helper T cells is dependent on APC function. Antigen presentation allows for specificity of adaptive immunity and can contribute to immune responses against both intracellular and extracellular pathogens. It is also involved in defense against tumors. Some cancer therapies involve the creation of artificial APCs to prime the adaptive immune system to target malignant cells.

Dendritic cells (DCs) are considered potent antigen-presenting cells (APCs), and are effective inducers of protective immunity against infectious diseases and cancer. These have prompted intense interest in the use of DCs as cellular vaccines; especially DCs differentiated form peripheral blood monocytes. DCs play a pivotal role in controlling the interface of innate and acquired immunity by recognizing pathogens or tumor cells and providing soluble and intercellular signals to immune cells. These functions of DCs are largely dependent on the expression of specialized surface receptors, 'pattern recognition receptors' (PRRs), represented, most notably, by toll-like receptors (TLRs) and C-type lectins or lectin-like receptors (LLRs).

B cells represent a large pool of potent APCs, and are likely the only autologous APCs alternative to DC that can be generated ex vivo in large numbers for immunotherapeutic purposes. While B cells have been described to induce T cell tolerance or even to block antitumor immune responses in vivo, these reports were restricted to resting B cells lacking high expression of important accessory and costimulatory molecules expression. On the other hand, B cells can be activated to become effective APCs by cells expressing CD40L in combination with cytokines or TLR ligands. However, these approaches either did not induce optimal B cell activation (in the case of TLR ligands) or required co-culture of B cells with transfected cell lines (in the case of CD40L). These limitations make them less suitable for clinical application. Hence, practical methods and platforms that induce activation and proliferation of APCs, as well as increase their efficacy in vivo, are needed in the art to target multiple types of tumors and infectious diseases.

SUMMARY

Disclosed herein is a platform for enhancing the effectiveness of in vivo antigen presentation and antigen-specific immune responses, wherein the platform comprises: a composition comprising at least two cytokines, wherein two of the cytokines are Fms-related tyrosine kinase 3 ligand (Flt-3L) and granulocyte-macrophage colony-stimulating factor (GM-CSF), wherein Flt-3L is present in an amount to be administered at 8 µg/kg or less; and wherein a population of APCs have been loaded with antigen and adjuvants to prime host antigen-specific immune responses in vivo. The platform can also include other factors used to boost this response including 1-ethyl 1-3-(3-dimethylaminopropyl)-carbodiimide (EDAC), cycloheximide (CHX), and α-galactosylceramide (α-GalCer). EDAC (or other chemical cross-linkers), CHX, and α-GalCer (and other similar adjuvants) can be used together or individually with the platform comprising Flt-3L and GM-CSF.

Also disclosed herein is a method for enhancing effectiveness of antigen presentation and antigen-specific immune responses in a subject in need thereof, the method comprising: administering to the subject a composition comprising at least two cytokines, wherein two of the cytokines are Flt-3L and GM-CSF, wherein Flt-3L is present at a dosage level of 8 µg/kg or less; and administering to the subject a population of antigen presenting cells (APCs) which have been cross-linked or loaded with antigen and adjuvants.

Disclosed herein is a platform for enhancing effectiveness of antigen presentation and antigen-specific immune responses, wherein the platform comprises: a composition comprising FTY720; and a population of APCs which have been cross-linked or loaded with antigen and adjuvants. Such adjuvants are known to those of skill in the art.

Also disclosed is a method for enhancing effectiveness of antigen-presenting cells (APCs) in a subject in need thereof, the method comprising: administering to the subject a composition comprising FTY720; and administering to the subject a population of APCs which have been cross-linked or loaded with antigen and adjuvants.

Disclosed is a method for producing *Chlamydia*-activated antigen presenting cells (APCs) in a subject, the method comprising: obtaining APCs from a subject; exposing the APCs from step a) to *Chlamydia* spp., or an activating protein, peptide, or fragment thereof; exposing the APCs from step b) to anti-CD40 monoclonal antibodies; and exposing the APCs of step c) to a desired antigen, wherein the antigen is not derived from *Chlamydia* spp., thereby obtaining activated, antigen-presenting cells (CABs).

Also disclosed is a method for enhancing effectiveness of antigen-presenting cells (APCs) in a subject in need thereof, the method comprising: administering to the subject a composition comprising anti-IL6 and anti-PDL-1 monoclonal antibodies; and administering to the subject a population of APCs which have been cross-linked or loaded with antigen and adjuvant.

Also disclosed herein are vaccines and kits based on the platform.

The details of one or more embodiments of the invention are set forth in the accompanying drawings and the description below. Other features, objects, and advantages of the invention will be apparent from the description and drawings, and from the claims.

DETAILED DESCRIPTION

Definitions

Figure 1:
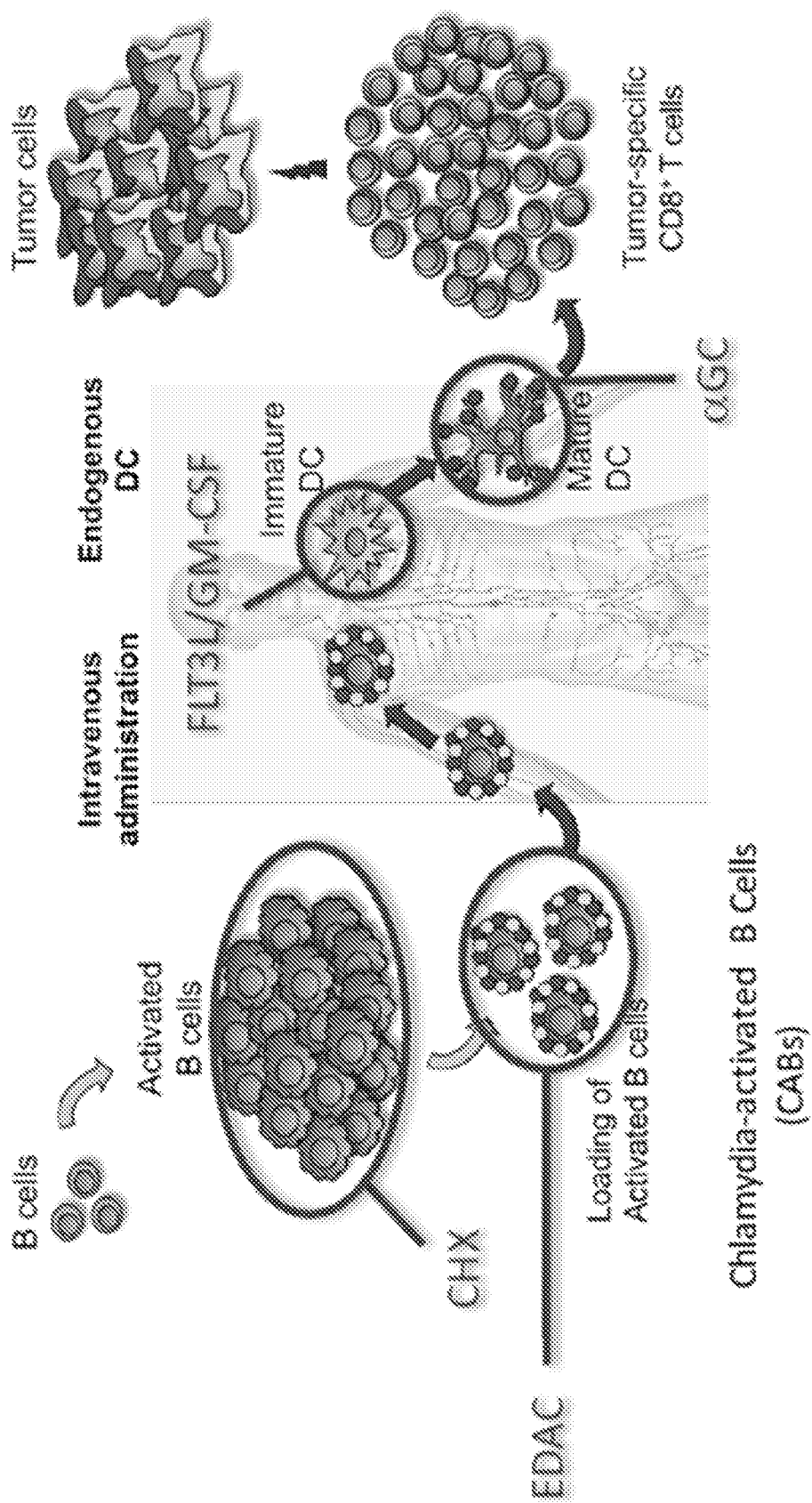
FIG. 1 shows a schematic of a methodology to improve in vivo antigen presentation and host antigen-specific immune responses. This methodology can be incorporated into vaccination strategies that increase host T cell responses and ability of the host to combat tumors and pathogens. Treatment of a tumor-bearing host with Flt-3L and GM-CSF, and FTY720 increases anti-tumor efficacy by increasing maturation of host dendritic cells (DCs).

"FTY720" is also known as "fingolimod." FTY720 is an immunomodulating drug, most often used clinically for treating multiple sclerosis (MS). Fingolimod is a sphingosine-1-phosphate receptor modulator, which sequesters lymphocytes in lymph nodes, preventing them from contributing to an autoimmune reaction. Also contemplated are analogs of FTY720, which are known to those of skill in the art.

"Anti-CD40 monoclonal antibody" is an antibody to CD40 (cluster of differentiation 40), which is a costimulatory protein found on antigen presenting cells which promotes their activation. The binding of CD154 (CD40L) on $T_H$ cells to CD40 activates antigen presenting cells and induces a variety of downstream effects.

"Anti-IL6 monoclonal antibody" refers to anti-interleukin-6 antibodies. Interleukin 6 is a cytokine involved in the host response to many inflammatory diseases and cancers.

"Anti-PDL-1 monoclonal antibody" refers to an antibody to programmed death-ligand 1 (PD-L1) also known as cluster of differentiation 274 (CD274) or B7 homolog 1 (B7-H1). It is a protein that in humans is encoded by the CD274 gene. Programmed death-ligand 1 (PD-L1) is a 40 kDa type 1 transmembrane protein.

"Fms-related tyrosine kinase 3 ligand" (Flt-3L) refers to a cytokine useful in stimulating proliferation and differentiation of hematopoietic progenitor cells.

"Granulocyte macrophage colony stimulating factor" (GM-CSF) refers to a cytokine which promotes monocyte migration into tissue and their differentiation into dendritic cells (DCs).

"1-ethyl 1-3-(3-dimethylaminopropyl)-carbodiimide" (EDAC) is a zero-length crosslinking agent.

"Cycloheximide" (CHX) is a protein biosynthesis inhibitor.

"α-Galactosylceramide" (α-GalCer) is a cerebroside that acts as a type 1 NKT cell activator.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of about 20% or about 10%, more preferably 5%, even more preferably 1%, and still more preferably 0.1% from the specified value, as such variations are appropriate to perform the disclosed methods.

The term "antigenic composition" refers to a composition comprising material which stimulates the immune system and elicits an immune response in a host or subject.

The term "elicit an immune response" refers to the stimulation of immune cells in vivo in response to a stimulus, such as an antigen. The immune response consists of both cellular immune responses, e.g., T cell and macrophage stimulation, and humoral immune responses, e.g., B cell and complement stimulation and antibody production. Immune response may be measured using techniques well-known in the art, including, but not limited to, antibody immunoassays, proliferation assays, cytokine production assays and others.

The term "vaccine" as used herein refers to a composition comprising an immunogenic epitope as described herein, which is useful to establish immunity to the pathogen or tumor cell in the subject. It is contemplated that the vaccine comprises a pharmaceutically acceptable carrier and/or an adjuvant. It is contemplated that vaccines are prophylactic or therapeutic.

A "prophylactic" treatment is a treatment administered to a subject who does not exhibit signs of a disease or exhibits only early signs for the purpose of decreasing the risk of developing pathology. The vaccines disclosed herein can be given as a prophylactic treatment to reduce the likelihood of developing a pathology or to minimize the severity of the pathology, if developed.

A "therapeutic" treatment is a treatment administered to a subject who exhibits signs or symptoms of pathology for the purpose of diminishing or eliminating those signs or symptoms. The signs or symptoms may be biochemical, cellular, histological, functional, subjective or objective.

The term "inactivated" is used herein to describe a microorganism, such as *Chlamydia* spp. (including *C. trachomatis, C. psittaci, C. pneumoniae* and *C. muridarum*), that is also known in the art as a "killed" or "dead" microorganism. An inactivated bacterium is a whole bacterium without infective properties and is produced from a "live" bacterium, regardless of whether the bacterium has been previously attenuated in any manner.

A "fragment" of a polypeptide refers to any portion of the polypeptide smaller than the full-length polypeptide or protein expression product. Fragments are, in one aspect, deletion analogs of the full-length polypeptide wherein one or more amino acid residues have been removed from the amino terminus and/or the carboxy terminus of the full-length polypeptide. Accordingly, "fragments" are a subset of deletion analogs described below.

The term "antibody," as used herein, refers to an immunoglobulin molecule which is able to bind to a specific epitope on an antigen. Antibodies can be intact immunoglobulins derived from natural sources or from recombinant sources and can be immunoreactive portions of intact immunoglobulins. Antibodies can be produced from the vaccines described herein, and may exist in a variety of forms including, for example, polyclonal antibodies, monoclonal antibodies, intracellular antibodies ("intrabodies"), Fv, Fab and F(ab)2, as well as single chain antibodies (scFv), heavy chain antibodies, such as camelid antibodies, synthetic antibodies, chimeric antibodies, and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

As used herein, to "alleviate" a disease means to reduce the frequency or severity of at least one sign or symptom of a disease or disorder.

An "effective amount" as used herein, means an amount which provides a therapeutic or prophylactic benefit.

As used herein, an "immunoassay" refers to any binding assay that uses an antibody capable of binding specifically to a target molecule to detect and quantify the target molecule.

As used herein, an "instructional material" includes a publication, a recording, a diagram, or any other medium of expression which can be used to communicate the usefulness of a compound, composition, method, platform, or system of the invention in the kit for practicing the methods described herein. The instructional material of the kit of the invention can, for example, be affixed to a container which contains the identified compound, composition, platform, or delivery system of the invention or be shipped together with a container which contains the identified compound, composition, method components, platform, or system of the invention. Alternatively, the instructional material can be shipped separately from the container with the intention that the instructional material and the compound be used cooperatively by the recipient.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The term "subject" refers to any individual who is the target of administration or treatment. The subject can be a vertebrate, for example, a mammal. Thus, the subject can be a human or veterinary patient, such as a companion animal or service animal. The term "patient" refers to a subject under the treatment of a clinical care provider (e.g., a physician).

As used herein, the terms "therapy" or "therapeutic regimen" refer to those activities taken to alleviate or alter a disorder or disease state, e.g., a course of treatment intended to reduce or eliminate at least one sign or symptom of a disease or disorder using pharmacological, surgical, dietary and/or other techniques. A therapeutic regimen may include a prescribed dosage of one or more drugs or surgery. Therapies will most often be beneficial and reduce or eliminate at least one sign or symptom of the disorder or disease state, but in some instances the effect of a therapy will have non-desirable or side effects. The effect of therapy will also be impacted by the physiological state of the subject, e.g., age, gender, genetics, weight, other disease conditions, etc.

The term "therapeutically effective amount" refers to the amount of the subject compound that will elicit the biological or medical response of a tissue, system, or subject that is being sought by a researcher, veterinarian, physician or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

To "treat" a disease as the term is used herein, means to reduce the frequency or severity of at least one sign or symptom of a disease or disorder experienced by a subject.

The term "cell" as used herein also refers to individual cells, cell lines, primary culture, or cultures derived from such cells unless specifically indicated. A "culture" refers to a composition comprising isolated cells of the same or a different type. A cell line is a culture of a particular type of cell that can be reproduced indefinitely, thus making the cell line "immortal." A cell culture can be a population of cells grown in vitro or ex vivo. A primary cell culture is a culture from a cell or taken directly from a living organism, which is not immortalized.

The term "biological sample" refers to a tissue (e.g., tissue biopsy), organ, cell (including a cell maintained in culture), cell lysate (or lysate fraction), biomolecule derived from a cell or cellular material (e.g. a polypeptide or nucleic acid), or body fluid from a subject. Non-limiting examples of body fluids include blood, urine, plasma, serum, tears, lymph, bile, cerebrospinal fluid, interstitial fluid, aqueous or vitreous humor, colostrum, sputum, amniotic fluid, saliva, anal and vaginal secretions, perspiration, semen, transudate, exudate, and synovial fluid.

The terms "tumor cell" or "cancer cell", used either in the singular or plural form, refer to cells that have undergone a malignant transformation that makes them pathological to the host organism. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but any cell derived from a cancer cell ancestor. This includes metastasized cancer cells, and in vitro cultures and cell lines derived from cancer cells.

The term "tumor-associated antigen" or "TAA" is used herein to refer to a molecule or complex which is expressed at a higher frequency or density by tumor cells than by non-tumor cells of the same tissue type. Tumor-associated antigens may be antigens not normally expressed by the host; they may be mutated, truncated, misfolded, or otherwise abnormal manifestations of molecules normally expressed by the host; they may be identical to molecules normally expressed but expressed at abnormally high levels; or they may be expressed in a context or milieu that is abnormal. Tumor-associated antigens may be, for example, proteins or protein fragments, complex carbohydrates, gangliosides, haptens, nucleic acids, or any combination of these or other biological molecules. Knowledge of the existence or characteristics of a particular tumor-associated antigen is not necessary for the practice of the invention.

The term "B cell" refers to a B lymphocyte. B cell precursors reside in the bone marrow where immature B cells are produced. B cell development occurs through several stages, each stage representing a change in the genome content at the antibody loci. In the genomic heavy chain variable region there are three segments, V, D, and J, which recombine randomly, in a process called VDJ rearrangement to produce a unique variable region in the immunoglobulin of each B cell. Similar rearrangements occur for the light chain variable region except that there are only two segments involved, V and J. After complete rearrangement, the B cell reaches the $IgM^+$ immature stage in the bone marrow. These immature B cells present a membrane bound IgM, i.e., B cell receptor (BCR), on their surface and migrate to the spleen, where they are called transitional B cells. Some of these cells differentiate into mature B lymphocytes. Mature B cells expressing the BCR on their surface circulate the blood and lymphatic system performing the role of immune surveillance. They do not produce soluble antibodies until they become fully activated. Each B cell has a unique receptor protein that will bind to one particular antigen. Once a B cell encounters its antigen and receives an additional signal from a $CD4^+$ T helper cell, it can further differentiate into either a plasma cell expressing and secreting soluble antibodies or a memory B cell.

The term "B cell" can also refer to any B lymphocyte which presents a fully rearranged, i.e., a mature, B cell receptor (BCR) on its surface. For example, a B cell can be an immature or a mature B cell and is preferably a naïve B cell, i.e., a B cell that has not been exposed to the antigen specifically recognized by the BCR on the surface of said B cell. The B cells can be memory B cells, preferably $IgG^+$ memory B cells. The term "B cells" can also refer to a mixture of B cells. A mixture of B cells can mean that the B cells in the mixture have different antigen-specificities, i.e., produce antibodies or fully rearranged BCRs which recognize a variety of antigens. The antibodies or BCRs of a single B cell are usually identical, also with respect to antigen-specificity.

The term "B cell secreting antibodies" preferably refers to plasma cells. The term "B cells carrying a BCR on their surface" preferably refers to B cells expressing a BCR, preferably a fully rearranged BCR, at their plasma membrane. In this context, "a BCR" preferably does not mean a single BCR but preferably means a multitude of BCRs.

The term "portion" refers to a fraction. A portion preferably means at least 20%, at least 30%, preferably at least 40%, preferably at least 50%, more preferably at least 60%, more preferably at least 70%, even more preferably at least 80%, and most preferably at least 90% of the entire entity. The term "substantial portion" preferably refers to at least 50%, more preferably at least 60%, more preferably at least 70%, even more preferably at least 80%, even more preferably at least 90%, even more preferably at least 95%, and most preferably at least 99% of the entire entity.

The term "clonal expansion" refers to a process wherein a specific entity is multiplied. In the context of the present invention, the term is preferably used in the context of an immunological response in which lymphocytes are stimulated by an antigen, proliferate, and the specific lymphocyte recognizing said antigen is amplified. Preferably, clonal expansion leads to differentiation of the lymphocytes, preferably into, for example, lymphocytes producing and secreting antibodies. B lymphocytes secreting antibodies are, for example, plasma cells.

The term "antigen" relates to an agent comprising an epitope against which an immune response is to be generated. The term "antigen" includes, in particular, proteins, peptides, polysaccharides, lipids, and nucleic acids, especially RNA and DNA, and nucleotides. The term "antigen" also includes derivatized antigens as secondary substance which becomes antigenic—and sensitizing—only through transformation (e.g., intermediately in the molecule, by completion with body protein), and conjugated antigens which, through artificial incorporation of atomic groups (e.g., isocyanates, diazonium salts), display a new constitutive specificity. In a preferred embodiment, the antigen is a tumor antigen, i.e., a constituent of cancer cells which may be derived from the cytoplasm, the cell surface and the cell nucleus, in particular those antigens which are produced, preferably in large quantity, intracellularly or as surface antigens on tumor cells. Examples are carcinoembryonic antigen, alpha-fetoprotein, isoferritin and fetal sulfoglycoprotein, a2-H-fetoprotein and γ-fetoprotein and various viral tumor antigens. In a further embodiment, the antigen is a part of a microbial pathogen (e.g., viral antigen) such as viral ribonucleoproteins or envelope proteins. In particular, the antigen or peptides thereof should be recognizable by a B cell receptor or an immunoglobulin molecule such as an antibody. Preferably, the antigen if recognized by a B cell receptor is able to induce in presence of appropriate co-stimulatory signals, clonal expansion of the B cell carrying the BCR specifically recognizing the antigen and the differentiation of such B cells into antibody secreting B cells. An antigen can present in a repetitive organization, i.e., the antigen comprises more than one, preferably at least 2, at least 3, at least 4, up to 6, 10, 12 or more agents or epitopes against which an immune response is to be generated or against which the antibodies which are to be produced. Such repetitive antigen preferably is capable of binding to more than one antibody of the same specificity. In other words, such repetitive antigen comprises more than one epitope, preferably identical epitope, and thus is capable of "cross-linking" antibodies directed to said epitope. The more than one agents or epitopes may be covalently or non-covalently linked, wherein a covalent linkage may be by any chemical grouping such as by peptide linkages. An antigen can be a fusion molecule comprising a repetition of an antigen peptide or comprising different antigen peptides having a common epitope. In one preferred embodiment, said antigen peptides are linked by peptide linkers.

As used herein, the terms "T lymphocyte" and "T cell," encompass any cell within the T lymphocyte lineage from T cell precursors (including Thy1 positive cells which do not have rearranged T cell receptor [TCR] genes) to mature T cells (i.e., single positive for $CD4^+$ or $CD8^+$, surface TCR positive cells).

As used herein, "$CD4^+$ T cell" and "CD4 T cell" refer to helper T cells, while "$CD8^+$ T cell" and "CD8 T cell" refer to cytotoxic T cells.

As used herein "T cell epitope" means a feature of a peptide or protein that is recognized by a T cell receptor in the initiation of an immunologic response to the peptide comprising that antigen. Recognition of a T cell epitope by a T cell is generally believed to be via a mechanism wherein T cells recognize peptide fragments of antigens which are bound to Class I or Class II Major Histocompatibility Complex (MHC) molecules expressed on antigen-presenting cells (See e.g., Moeller (ed.), Immunol. Rev., 98:187 [1987]).

As used herein, "T cell proliferation," refers to the number of T cells produced during the incubation of T cells with the antigen presenting cells, with or without antigen.

"Baseline T cell proliferation," as used herein, refers to the degree of T cell proliferation that is normally seen in an individual in response to exposure to antigen presenting cells in the absence of cognate peptide or protein antigen. For purposes herein, baseline T cell proliferation level is determined on a per sample basis for each individual as the proliferation of T cells in response to antigen presenting cells in the absence of antigen.

Ranges: throughout this disclosure, various aspects of the invention can be presented in a range format. It should be understood that the description in range format is merely for convenience and brevity, and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

According to the methods taught herein, the subject is administered an effective amount of the agent. The terms effective amount and effective dosage are used interchangeably. The term effective amount is defined as any amount necessary to produce a desired physiologic response. Effective amounts and schedules for administering the agent may be determined empirically, and making such determinations is within the skill in the art. The dosage ranges for administration are those large enough to produce the desired effect in which one or more symptoms of the disease or disorder are affected (e.g., reduced or delayed). The dosage should not be so large as to cause substantial adverse side effects, such as unwanted cross-reactions, anaphylactic reactions, and the like. Generally, the dosage will vary with the age, condition, sex, type of disease, the extent of the disease or disorder, route of administration, or whether other drugs are included in the regimen, and can be determined by one of skill in the art. The dosage can be adjusted by the individual physician in the event of any contraindications. Dosages can vary, and can be administered in one or more dose administrations daily, for one or several days. Guidance can be found in the literature for appropriate dosages for given classes of pharmaceutical products.

As used herein the terms treatment, treat, or treating refers to a method of reducing the effects of a disease or condition or symptom of the disease or condition. Thus in the disclosed method, treatment can refer to a 10%, 20%, 30%, 40%, 50%, 60%, 70%, 80%, 90%, or 100% reduction in the severity of an established disease or condition or symptom of the disease or condition. For example, a method for treating a disease is considered to be a treatment if there is a 10% reduction in one or more symptoms of the disease in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition.

As used herein, the terms prevent, preventing, and prevention of a disease or disorder refers to an action, for example, administration of a therapeutic agent, that occurs before or at about the same time a subject begins to show one or more symptoms of the disease or disorder, which inhibits or delays onset or exacerbation of one or more symptoms of the disease or disorder. As used herein, references to decreasing, reducing, or inhibiting include a change of 10%, 20%, 30%, 40%, 50%, 60%, 70%, 80%, 90% or greater as compared to a control level. Such terms can include but do not necessarily include complete elimination.

General Description

Disclosed herein is a platform for enhancing effectiveness of antigen-presenting cells (APCs), wherein the platform comprises: a composition comprising at least two cytokines, wherein two of the cytokines are Fms-related tyrosine kinase 3 ligand (Flt-3L) and granulocyte-macrophage colony-stimulating factor (GM-CSF), wherein Flt-3L is present in an amount to be administered at 8 µg/kg or less; and a population of APCs which have been loaded with antigen are intended to present the loaded antigen to endogenous immune cells, including APCs.

Also, disclosed herein is a platform for enhancing effectiveness of antigen presentation and antigen-specific immune responses, wherein the platform comprises a composition comprising FTY720; and a population of APCs which have been loaded with antigen.

The platform can also include other factors, which are described in more detail below. These factors include, but are not limited to, 1-ethyl 1-3-(3-dimethylaminopropyl)-carbodiimide (EDAC), cycloheximide (CHX), FTY720, and α-galactosylceramide (α-GalCer). EDAC (or other chemical crosslinkers), CHX, FTY720 and α-GalCer (or their equivalent adjuvants, which are discussed below) can be used together or individually with the platform comprising Flt-3L and GM-CSF.

Also disclosed herein is a method for enhancing effectiveness of in vivo antigen presentation in a subject in need thereof, the method comprising: administering to the subject a composition comprising at least two cytokines, wherein two of the cytokines are Flt-3L and GM-CSF, wherein Flt-3L is present at a dosage level of 8 µg/kg or less; and wherein administering to the subject a population of APCs which have been cross-linked or loaded with antigen and one or more adjuvants. It is possible that the administered APCs subsequently present the loaded antigen to endogenous host APCs and other endogenous immune cells.

FMS-like tyrosine kinase 3 ligand (Flt-3L) is an endogenous small molecule that functions as a cytokine and growth factor that increases the number of immune cells (lymphocytes (B cells and T cells)) by activating the hematopoietic progenitors. It acts by binding to and activating FLT3 (CD135) which is found on what (in mice) are called multipotent progenitor (MPP) and common lymphoid progenitor (CLP) cells. As used herein, the term "Flt3-ligand" refers to a genus of polypeptides that are described in U.S. Pat. No. 5,554,512, EP 0627487 A2 and in WO 94/28391, both incorporated herein by reference.

Granulocyte macrophage colony stimulating factor (GM-CSF), is a hematopoietic growth factor which promotes the proliferation and differentiation of hematopoietic progenitor cells. The cloned gene for GM-CSF has been expressed in bacteria, yeast and mammalian cells. The endogenous human protein is a monomeric glycoprotein with a molecular weight of about 22,000 daltons. GM-CSF produced in a yeast expression system is commercially available as Leukine® from Immunex Corporation, Seattle, Wash. It is a glycoprotein of 127 amino acids characterized by three primary molecular species having molecular masses of 19,500, 16,800, and 15,500 daltons. GM-CSF is described in U.S. Pat. Nos. 5,108,910, and 5,229,496 each of which is incorporated herein by reference.

The methods disclosed herein can be used to increase induction of antigen-specific T cells against tumors and pathogens for active or passive immunotherapy, immunomonitoring and research purposes. The methods disclosed herein can also be used to increase induction of antigen-specific T cells against tumors in individuals at high-risk for tumor development (i.e., individuals with pre-malignant or pre-cancerous states). APCs are capable of processing foreign protein antigens, presenting immunogenic peptides and stimulating T-cells, such as allogeneic naïve $CD4^+$ and $CD8^+$ T cells, as wells as naïve and memory antigen-specific $CD4^+$ and $CD8^+$ T cells. These properties allow for efficient priming of in vivo T cell responses, including those desirable in the treatment of cancer.

APCs produced under the conditions disclosed herein can be combined with any desired antigen or combination of antigens, as well as with immunogenic peptides, by a variety of techniques known to those of skill in the art. APCs treated with the methods disclosed herein can be administered intravenously to the subject, for example. The magnitude of T cell proliferation and activation is dependent on the number of APCs to be administered. Due to the high number of cells that can be obtained with the methods disclosed herein, for example, the treated APCs disclosed herein can be pulsed with cognate tumor antigens or tumor-specific peptides to induce tumor-specific $CD8^+$ T cells responses, capable of rejecting the corresponding tumor challenges in murine models.

As a result of the disclosed method of increasing APC numbers, these cells can be used in a wide range of approaches to present a desired antigen, such as a tumor-associated antigen to T cells. For example, human APCs can stimulate human allogeneic naïve $CD4^+$ and $CD8^+$ T cells. They can also prime autologous naïve and memory T cells specific for viral and tumor antigens in animals, including companion animals and humans. Furthermore, in mice these enhanced T cell responses are capable of promoting rescue from lethal viral infections and regressing established tumors.

The APCs used in the platform described herein (shown in the schematic of FIG. 1) can have multiple advantages in comparison to APCs which have not been used with the platform described herein. Therefore, disclosed herein are APCs that have an improved capacity to present antigen and activate T cells as compared to APCs which are not in a platform with FTY720, α-GalCer (or their equivalent adjuvants discussed below), Flt-3L, and GM-CSF. "Improved" is meant that, compared to administration of APCs without FTY720, α-GalCer (or their equivalent adjuvants discussed below), Flt-3L, and GM-CSF exposure, the APCs which are given to a subject who has been exposed to FTY720, α-GalCer (or their equivalent adjuvants discussed below), Flt-3L, and GM-CSF have a greater ability to present antigen and activate T cells. This increased ability can be a 10, 20, 30, 40, 50, 60, 70, 80, 90, or 100% increase. It can also be a 2, 3, 4, 5, 6, 7, 8, 9, or 10 fold increase, or more.

Also disclosed is an increased frequency of dendritic cells in secondary lymphoid organs and tumors in a platform using Flt-3L and GM-CSF (compared to a platform without Flt-3L and GM-CSF). By "increased frequency" is meant that, compared to hosts in a platform without Flt-3L and GM-CSF, hosts which have been exposed to Flt-3L and GM-CSF have a greater number of endogenous dendritic cells. This increased frequency can be a 10, 20, 30, 40, 50, 60, 70, 80, 90, or 100% or more increase. It can also be a 2, 3, 4, 5, 6, 7, 8, 9, or 10 fold increase of dendritic cells, or more.

Also disclosed is increased antigen-specific T cell priming compared to a platform without Flt-3L and GM-CSF. By "increased priming" is meant that, compared to a platform without Flt-3L and GM-CSF, antigen-specific T cell priming occurs more frequently. This increased frequency can be a 10, 20, 30, 40, 50, 60, 70, 80, 90, or 100% or more increase in antigen-specific T cell priming. It can also be a 2, 3, 4, 5, 6, 7, 8, 9, or 10 fold increase, or more.

Also disclosed is decreased myeloid derived suppressor cell (MDSC) frequency compared to a platform without Flt-3L and GM-CSF. By "decreased MDSC" frequency is meant that, compared to a platform without Flt-3L and GM-CSF, MDSCs occur less frequently. This decreased frequency can be a 10, 20, 30, 40, 50, 60, 70, 80, 90, or 100% decrease in MDSC frequency.

Also disclosed is an increased differentiation of intra-tumoral macrophages as compared to a platform without Flt-3L and GM-CSF. By "increased differentiation" is meant that, compared to a platform without Flt-3L and GM-CSF, differentiation of intra-tumoral macrophages occurs more frequently. This increased frequency can be a 10, 20, 30, 40, 50, 60, 70, 80, 90, or 100% or more increase in differentiation of intra-tumoral macrophages. It can also be a 2, 3, 4, 5, 6, 7, 8, 9, or 10 fold increase of intra-tumoral macrophages, or more.

Also disclosed is an increased frequency of infused APCs in secondary lymphoid organs compared to a platform without FTY720. By "increased frequency" is meant that, compared to hosts in a platform without FTY720, hosts which have been exposed to FTY720 have a greater number of infused APCs in secondary lymphoid organs. This increased frequency can be a 10, 20, 30, 40, 50, 60, 70, 80, 90, or 100% or more increase. It can also be a 2, 3, 4, 5, 6, 7, 8, 9, or 10 fold increase of infused APCs, or more.

Further disclosed is increased antigen-specific T cell priming compared to a platform without FTY720. By "increased priming" is meant that, compared to a platform without FTY720, antigen-specific T cell priming occurs more frequently. This increased frequency can be a 10, 20, 30, 40, 50, 60, 70, 80, 90, or 100% or more increase in antigen-specific T-cell priming. It can also be a 2, 3, 4, 5, 6, 7, 8, 9, or 10 fold increase, or more.

Figure 2B:
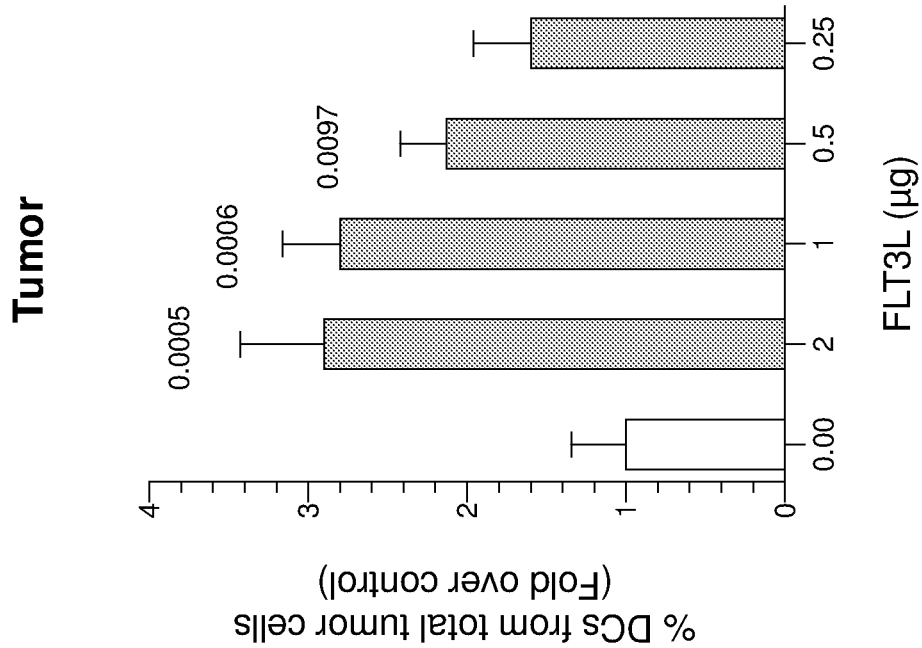
FIG. 2A-B shows that low dose treatment of mice with Flt-3L and GM-CSF increased the number of $CD8^+$ and CD11b DCs in a dose response manner with varying doses of Flt3-L (A). In addition, treatment increased percentages of $CD8^+CD103^+$ DCs (DCs with the capacity for cross-presentation) (B).
Figure 2A:
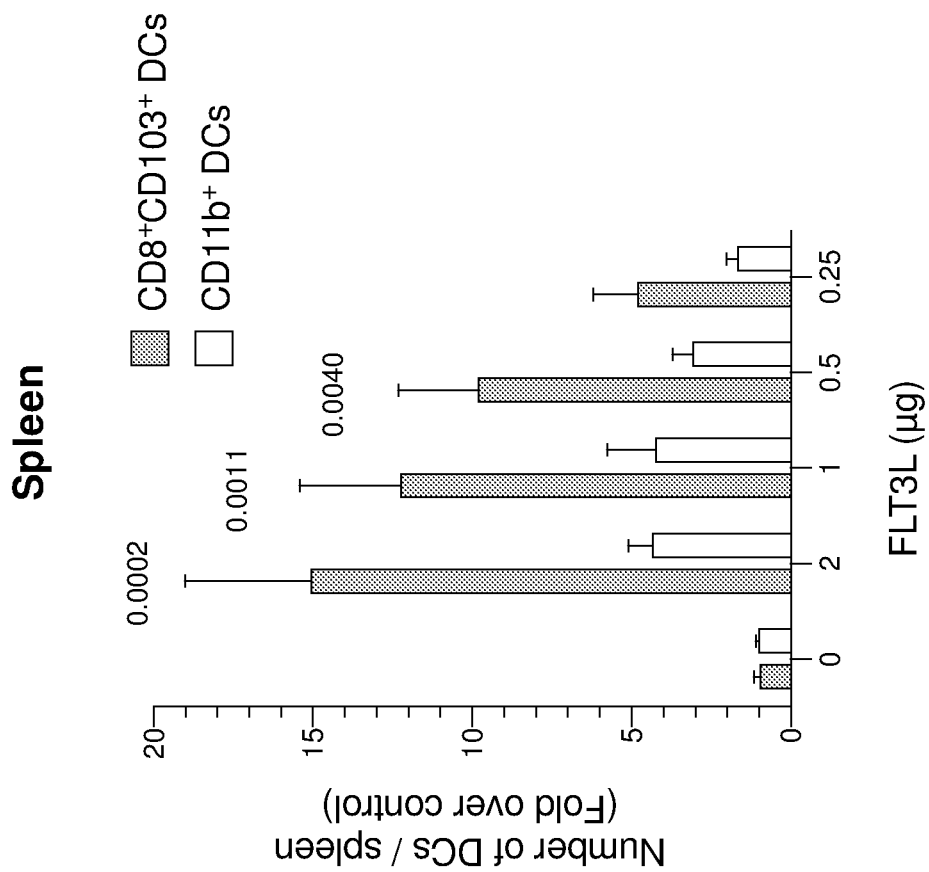
Figure 3B:
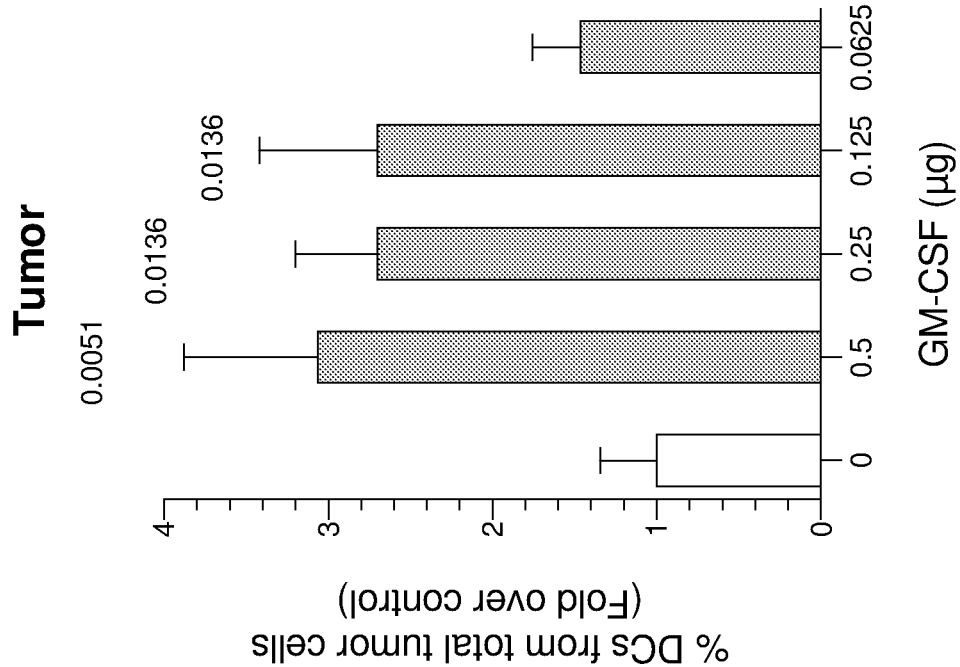
FIG. 3A-B shows that low dose treatment of mice with Flt-3L and GM-CSF increased the number of $CD8^+$ and CD11b DCs in a dose response manner with varying doses of GM-CSF (A). In addition, treatment increased percentages of $CD8^+CD103^+$ DCs (DCs with the capacity for cross-presentation) (B).
Figure 3A:
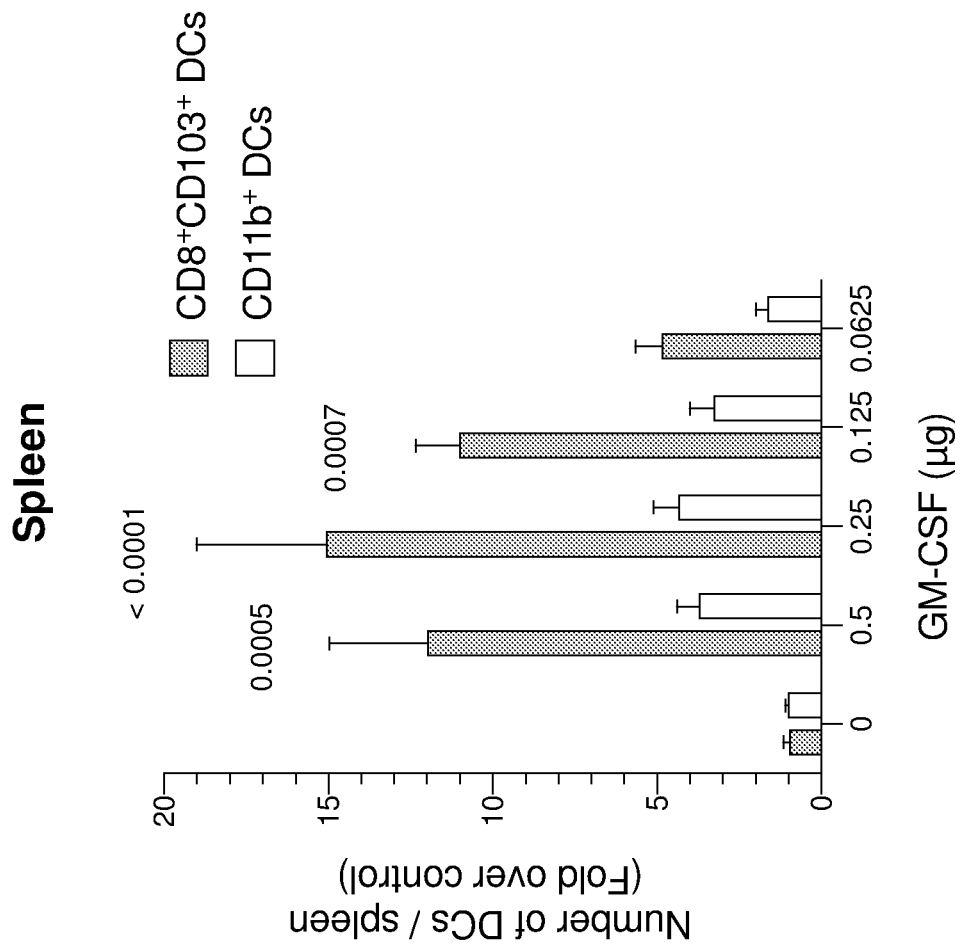
Figure 7:
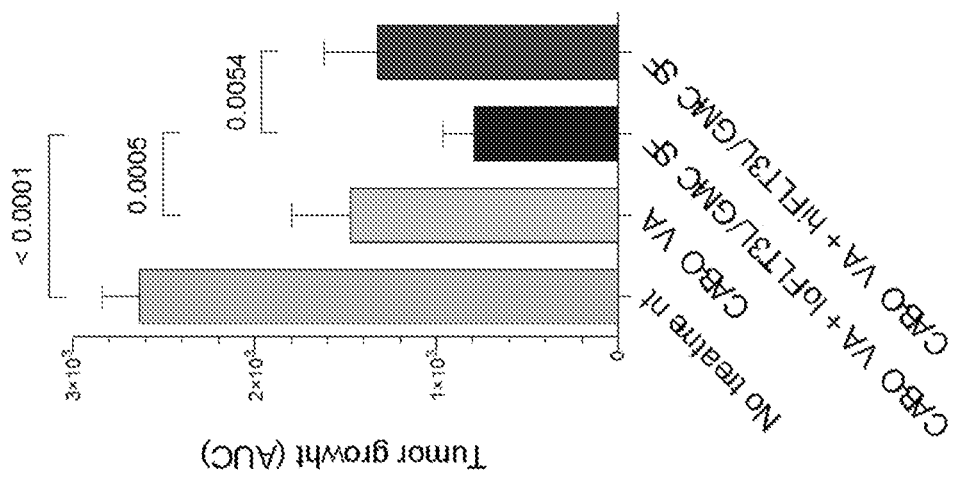
FIG. 7 shows low-dose Flt-3L/GM-CSF increases antitumor activity of CABs.
Figure 7:
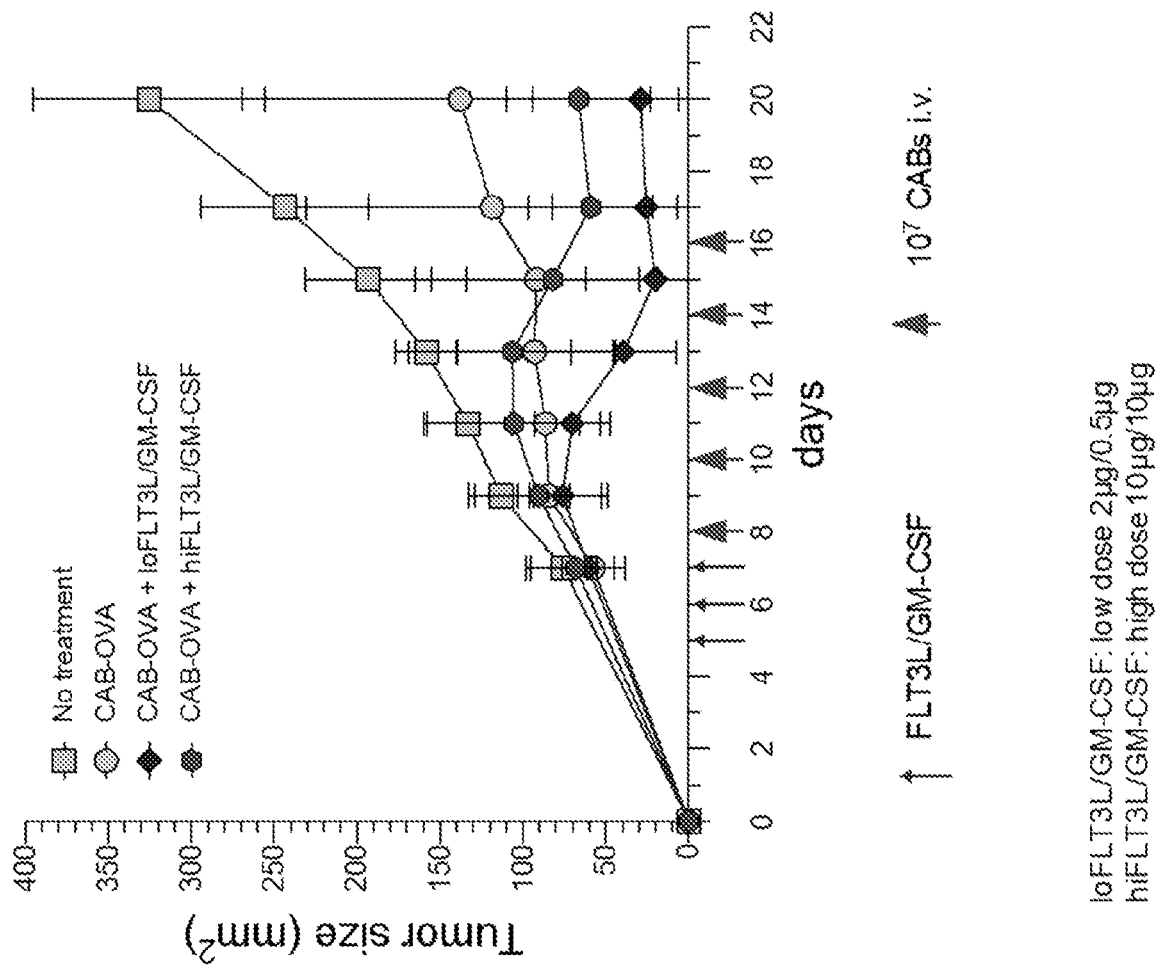

Importantly, FIG. 7 shows the effectiveness of low-dose versus high dose treatment using GM-CSF and Flt-3L. It is demonstrated that low doses of GM-CSF and Flt-3L (as defined herein) are more effective at reducing tumor size than higher doses of GM-CSF and Flt-3L. It is noted that in FIGS. 2, 3 and 7, the Flt-3L mouse dose is 0.5 μg-2 μg per mouse (20 g), or 25 μg-100 μg per Kg (the calculated comparable human dose is 2 μg-8 μg per kg). For GM-CSF, the mouse dose is 0.125 μg-0.5 μg per mouse (20 g), 6.25 μg-25 μg per kg (the calculated comparable human dose is 0.5 μg-2 μg per kg). "Low dose" is therefore defined as 2 μg-8 μg per kg in humans for Flt-3L, and 0.5 μg-2 μg per kg in humans for GM-CSF. "High dose" is defined as any amount above 8 μg/kg of Flt-3L and above 2 μg/kg of GM-CSF.

FTY720 can be given to the subject with antigen presenting cells. For example, FTY720 can be given concomitantly with APCs. Alternatively, FTY720 can be given to a subject prior to APCs, such as 1, 2, 3, 4, 5, 6, 7, 8, 9, 10, 11, 12, 24, 36, 48, 60, or 72 hours or more before the APCs. FTY720 can also be given to a subject after APCs. For example, FTY720 can be given 1, 2, 3, 4, 5, 6, 7, 8, 9, 10, 11, 12, 24, 36, 48, 60, or 72 hours or more after APCs are administered. The dosage of FTY720 given to the subject can be 1, 2, 3, 4, 5, 6, 7, 8, 9, 10, 20, 50 µg/kg, or any amount lesser, greater, or in-between these amounts.

Administering FTY720 to a subject can be done in conjunction with other treatments, factors, or APC-enhancing methods, which are discussed in more detail below. These include the use of cytokines such as GM-CSF and/or Flt-3L. Flt-3L, for example, can be present in an amount to be administered at 8 µg/kg or less. Other factors include, but are not limited to, 1-ethyl 1-3-(3-dimethylaminopropyl)-carbodiimide (EDAC), cycloheximide (CHX), and α-galactosylceramide (α-GalCer). EDAC (or other chemical cross-linkers), CHX, and α-GalCer (or other comparable adjuvants detailed below) can be used together or individually in this platform.

In the platform described herein, the APCs can be cross-linked or loaded with adjuvant. Adjuvants are described in more detail below. The population of APCs which have been loaded with antigen, present the loaded antigen to endogenous immune cells. The antigen can be a protein, peptide, or any amine-containing molecule. The antigen can be cross-linked to an APC, such as with (1-ethyl-3-(3-dimethylaminopropyl) carbodiimide hydrochloride (EDAC). The APCs can be treated with cycloheximide (CHX) prior to being cross-linked with antigen. Antigens, as well as cross-linking antigen methods, are described in more detail below. The APCs can be exposed to α-galactosylceramide (α-GalCer) or an equivalent adjuvant. This is described in more detail below as well.

Exposure of a subject to the platforms disclosed herein can result in increased anti-tumor or anti-microbial pathogen effector function of a host's antigen-specific T cell response compared to a platform without FTY720, α-GalCer (or equivalent adjuvants discussed below), Flt-3L or GM-CSF. The platform disclosed herein can be used to increase induction of antigen-specific T cells against tumors and pathogens for active or passive immunotherapy, immuno-monitoring and research purposes. The methods disclosed herein can also be used to increase induction of antigen-specific T cells against tumors in individuals at high-risk for tumor development (i.e., individuals with pre-malignant or pre-cancerous states). As introduced above, APCs are capable of processing foreign protein antigens, presenting immunogenic peptides and stimulating T cells, such as allogeneic naïve CD4$^+$ and CD8$^+$ T cells, as wells as naïve and memory antigen-specific CD4$^+$ and CD8$^+$ T cells. These properties allow for efficient priming of in vivo T cell responses, including those desirable in the treatment of cancer.

APCs produced under the conditions disclosed herein can be combined with any desired antigen or combination of antigens, as well as with immunogenic peptides, by a variety of techniques known to those of skill in the art. APCs treated with the methods disclosed herein can be administered intravenously to the subject, for example. The magnitude of T cell proliferation and activation is dependent on the number of APCs to be administered. Due to the high number of cells that can be obtained with the methods disclosed herein, for example, the treated APCs disclosed herein can be pulsed with cognate tumor antigens or tumor-specific peptides and induce tumor-specific CD8$^+$ T cells responses (these responses were shown capable of rejecting the corresponding tumor challenges in murine models).

The APCs used in the platform described herein (shown in the schematic of FIG. 1) can have multiple advantages in comparison to APCs which have not been used with the platform described herein. Some of these advantages can be seen in FIGS. 22, 23, 24, 25 and 26. Therefore, disclosed herein are APCs that have an improved capacity to present antigen and activate T cells as compared to APCs which are not in a platform with Flt-3L, GM-CSF, α-GalCer (or other comparable adjuvants discussed below), and/or FTY720. By "improved" is meant that, compared to administration of APCs without Flt-3L, α-GalCer (or other equivalent adjuvants discussed below), GM-CSF, and/or FTY720 exposure, the APCs which are given to a subject who has been exposed to Flt-3L, GM-CSF, α-GalCer (or other equivalent adjuvants discussed below), and/or FTY720 have a greater ability to present antigen and activate T cells. This increased ability can be a 10, 20, 30, 40, 50, 60, 70, 80, 90, or 100% increase. It can also be a 2, 3, 4, 5, 6, 7, 8, 9, or 10 fold increase, or more.

Also disclosed is an increased frequency of dendritic cells in secondary lymphoid organs and tumors compared to a platform without FTY720, α-GalCer (or other equivalent adjuvants discussed below), Flt-3L and/or GM-CSF. By "increased frequency" is meant that, compared to hosts in a platform without FTY720, α-GalCer (or other equivalent adjuvants detailed below), Flt-3L and/or GM-CSF, the hosts which have been exposed to FTY720, α-GalCer (or other comparable adjuvants discussed below), Flt-3L and/or GM-CSF have a greater number of endogenous dendritic cells. This increased frequency can be a 10, 20, 30, 40, 50, 60, 70, 80, 90, or 100% or more increase. It can also be a 2, 3, 4, 5, 6, 7, 8, 9, or 10 fold increase of dendritic cells, or more. This increased frequency of endogenous DCs, combined with the increased recruitment of infused APCs, and the activation of endogenous APCs boosts antigen-specific T cell responses and increases the efficacy of the platform described herein.

Further disclosed is increased antigen-specific T cell priming compared to a platform without Flt-3L, GM-CSF, α-GalCer (or other equivalent adjuvants discussed below), and/or FTY720. By "increased priming" is meant that, compared to a platform without FTY720, antigen-specific T cell priming occurs more frequently. This increased frequency can be a 10, 20, 30, 40, 50, 60, 70, 80, 90, or 100% or more increase in antigen-specific T-cell priming. It can also be a 2, 3, 4, 5, 6, 7, 8, 9, or 10 fold increase, or more. Also disclosed is the enhanced anti-tumor or anti-microbial pathogen effector function of the host's antigen-specific T cell responses induced with use of the platform.

Disclosed herein is a vaccine created using the platform described herein. Such vaccines are described in more detail below.

Disclosed herein are kits comprising Flt-3L, GM-CSF, and/or FTY720 and a population of APCs which have been loaded with antigen and adjuvants to prime host antigen-specific immune responses in vivo. The kit can also comprise CHX, EDAC, and α-GalCer or other equivalent adjuvants, including adjuvants of FTY720 In another embodiment, the kit can comprise instructions for producing antigen-loaded APCs, along with an immunogenic cell such as a B cell or a dendritic cell. The kit can also comprise anti-CD40 monoclonal antibodies, and anti-IL6 and/or anti-PDL-1, for example.

Anti-CD40 Monoclonal Antibodies

Disclosed herein is a method for producing activated, antigen-presenting *Chlamydia*-activated antigen presenting cells (APCs) in a subject, the method comprising: a) obtaining APCs from a subject; b) exposing the APCs from step a)

to *Chlamydia* spp., or an activating protein, peptide, or fragment thereof; c) exposing the APCs to anti-CD40 monoclonal antibodies; and d) exposing the APCs to a desired antigen, wherein the antigen is not derived from *Chlamydia* spp., thereby obtaining activated, antigen-presenting cells (such as *Chlamydia*-active B cells, i.e., CABs). It is noted that steps b), c), and d) can occur in any order. Anti-IL6 and anti-PDL-1 monoclonal antibodies can be given along with CABs derived from this method to a subject in need thereof.

The APCs can also be exposed to interleukin-2 (IL-2) and IL-4, and these cytokines can be further combined with anti-CD40 monoclonal antibodies to increase APC expansion. The APCs disclosed in this method can be cross-linked or loaded with adjuvant. The population of APCs which have been loaded with antigen present the loaded antigen to endogenous immune cells in the host.

When the APCs which have been exposed to anti-CD40 monoclonal antibodies are to be given to a subject, they can be given with other platforms and methods disclosed herein. For example, FTY720 can be given to the subject. Anti-IL-6 and anti-PDL-1 monoclonal antibodies can also be given to the subject. GM-CSF and/or Flt-3L can also be given. Flt-3L, for example, can be present in an amount to be administered at 8 µg/kg or less. Other factors include, but are not limited to, 1-ethyl 1-3-(3-dimethylaminopropyl)-carbodiimide (EDAC), cycloheximide (CHX), and α-galactosylceramide (α-GalCer) (or other equivalent adjuvants discussed below). EDAC (or other chemical crosslinkers), CHX, and α-GalCer (or other comparable adjuvants detailed below). These can be used together or individually.

In the platform described herein, the APCs can be cross-linked or loaded with adjuvant. Adjuvants are described in more detail below. The population of APCs which have been loaded with antigen present the loaded antigen to endogenous immune cells. The antigen can be a protein, peptide, or any amine-containing molecule. The antigen can be cross-linked to an APC, such as with (1-ethyl-3-(3-dimethylaminopropyl) carbodiimide hydrochloride (EDAC). The APCs can be treated with cycloheximide (CHX) prior to being cross-linked with antigen. Antigens, as well as cross-linking antigen methods, are described in more detail below. The APCs can be exposed to α-galactosylceramide (α-GalCer) or an equivalent adjuvant. This is described in more detail below.

The methods disclosed herein of exposing APCs to anti-CD40 antibodies results in an increase in ex vivo expansion of APCs when compared to a population of APCs not exposed to anti-CD40 monoclonal antibodies. As used herein expansion of APCs includes stimulation of proliferation of the cells as well as prevention of apoptosis or other processes that lead to death of the cells. As used herein, "culturing" and "incubation" are used to indicate that the cells are maintained in cell culture medium for a period of time with the appropriate additives (feeder cells, cytokines, agonists, other stimulatory molecules or media, which may include buffers, salts, sugars, serum or various other constituents). Those of skill in the art will appreciate that the culturing or incubation time may be varied to allow proper expansion, to adjust for different cell densities or frequencies of individual subsets, and to allow an investigator to properly time use of the cells. Thus precise culture length may be determined empirically by one of skill in the art.

Anti-IL6 and Anti-PDL-1 Monoclonal Antibodies

Disclosed herein is a method for enhancing effectiveness of antigen-presenting cells (APCs) in a subject in need thereof, the method comprising: a) administering to the subject a composition comprising anti-IL6 and anti-PDL-1 monoclonal antibodies; and b) administering to the subject a population of APCs which have been cross-linked or loaded with antigen and adjuvant. The antibodies can be administered simultaneously to the subject in need thereof, or one can be administered before the other. For example, they can be administered 1, 2, 3, 4, 5, 6, or more hours apart from each other.

Anti-IL6 and anti-PDL-1 monoclonal antibodies can be given to subjects in conjunction with APCs. For example, anti-IL6 and anti-PDL-1 monoclonal antibodies can be given concomitantly with APCs. Alternatively, anti-IL6 and anti-PDL-1 monoclonal antibodies can be given to a subject prior to APCs, such as 1, 2, 3, 4, 5, 6, 7, 8, 9, 10, 11, 12, 24, 36, 48, 60, or 72 hours or more before APC administration. Anti-IL6 and anti-PDL-1 monoclonal antibodies can also be given to subjects after APCs. For example, anti-IL6 and anti-PDL-1 monoclonal antibodies can be given 1, 2, 3, 4, 5, 6, 7, 8, 9, 10, 11, 12, 24, 36, 48, 60, or 72 hours or more after APCs are administered.

Administering anti-IL6 and anti-PDL-1 monoclonal antibodies to a subject can be done in conjunction with other treatments, factors, or APC-enhancing methods, which are discussed in more detail below. In the platform described herein, the APCs can be cross-linked or loaded with antigen and adjuvant. Adjuvants are described in more detail below. The population of APCs which have been loaded with antigen present the loaded antigen to endogenous immune cells. The antigen can be a protein, peptide, or any amine-containing molecule. The antigen can be cross-linked to an APC, such as EDAC). The APCs can be treated with CHX prior to being cross-linked with antigen. Antigens, as well as cross-linking antigen methods, are described in more detail below. The APCs can be exposed to α-GalCer or an equivalent adjuvant. This is also described in more detail below.

Exposure of a subject to the platform using anti-IL6 and anti-PDL-1 monoclonal antibodies can result in increased antigen-specific T cell priming compared to a platform without anti-IL6 and anti-PDL-1 monoclonal antibodies. These results are displayed in FIGS. 27 and 28. The platform disclosed herein can be used to increase induction of antigen-specific T cells against tumors and pathogens for active or passive immunotherapy, immunomonitoring and research purposes. The methods disclosed herein can also be used to increase induction of antigen-specific T cells against tumors in individuals at high-risk for tumor development (i.e., individuals with pre-malignant or pre-cancerous states). APCs are capable of processing foreign protein antigens, presenting immunogenic peptides and stimulating T cells, such as allogeneic naïve $CD4^+$ and $CD8^+$ T cells, as wells as naïve and memory antigen-specific $CD4^+$ and $CD8^+$ T cells. These properties allow for efficient priming of in vivo T cell responses, including those desirable in the treatment of cancer.

Disclosed herein is a vaccine created using the platform described herein. Such vaccines are described in more detail below.

Disclosed herein are kits comprising anti-IL6 and anti-PDL-1 monoclonal antibodies and a population of APCs which have been loaded with antigen and adjuvants to prime host antigen-specific immune responses in vivo. The kit can also comprise FTY720, Flt3-L, GM-CSF, CHX, EDAC, and α-GalCer or an equivalent thereof. In another embodiment, the kit can comprise instructions for producing antigen-loaded APCs, along with an immunogenic cell such as a B cell or a dendritic cell. The kit can also comprise anti-CD40 monoclonal antibodies.

Antigen Presenting Cells (APCs)

The antigen-presenting cells (APCs) disclosed herein can be from a variety of sources. Examples include, but are not limited to, B cells, such as *Chlamydia*-activated B cells (CABs), CD40-activated B cells, dendritic cells, and artificial APCs (cell-derived or synthetic), such as nanoparticles, anti-DEC-205 antibody conjugates, and anti-CLEC9 antibody conjugates.

B cells used herein can be obtained from a number of sources, including peripheral blood mononuclear cells, bone marrow, lymph node tissue, cord blood, tissue from a site of infection, splenic tissue, and tumors. Any number of B cell lines available in the art can be used with the platforms and methods disclosed herein. In certain embodiments of the methods described herein, B cells can be obtained from a unit of blood collected from a subject using any number of techniques known to the skilled artisan, such as FICOLL™ (copolymers of sucrose and epichlorohydrin that may be used to prepare high density solutions) separation. B cells can also be obtained from cadaveric splenic tissue. The B cells can be pre-treated to increase their effectiveness, such as CD40-activated B cells and *Chlamydia*-activated B-Cells (CABs).

Figure 24:
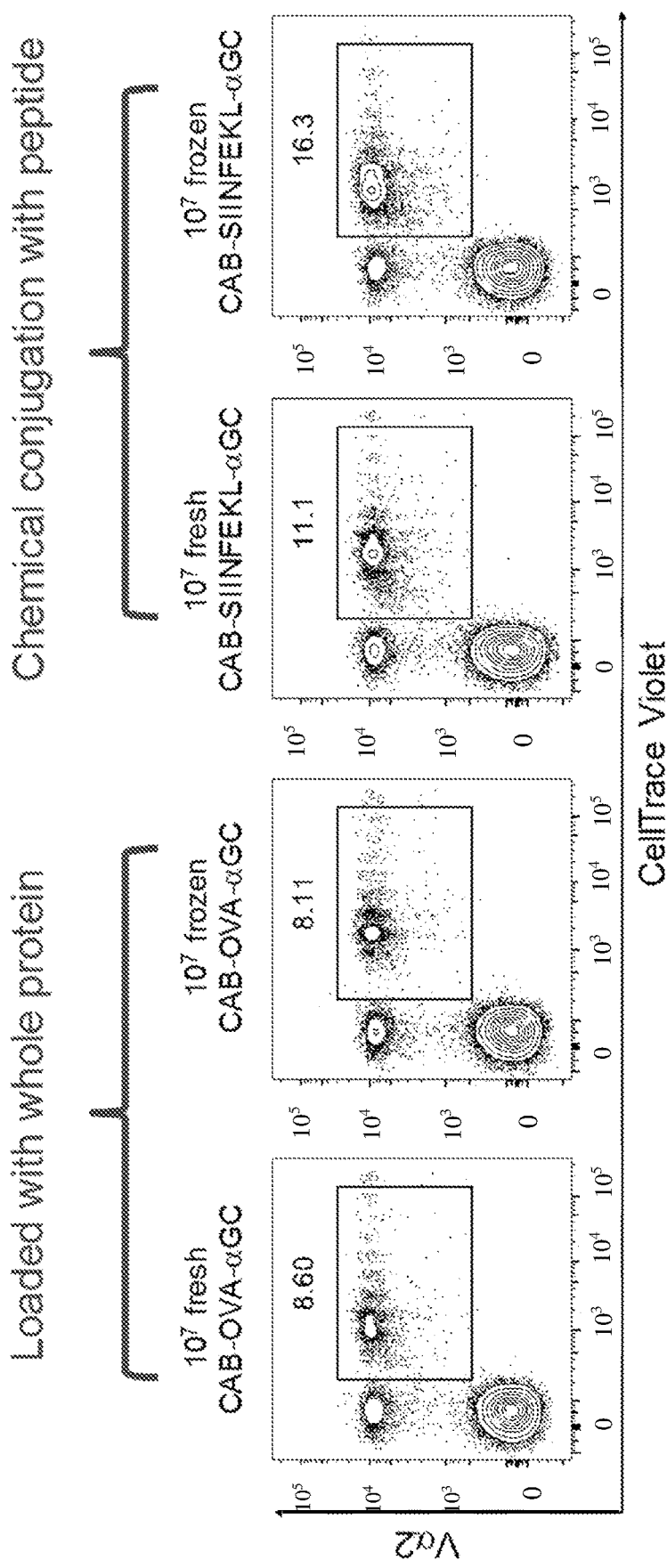
FIG. 24 shows that cryopreserved CABs do not lose their ability to prime robust $CD8^+$ T cells responses.
Figure 25:
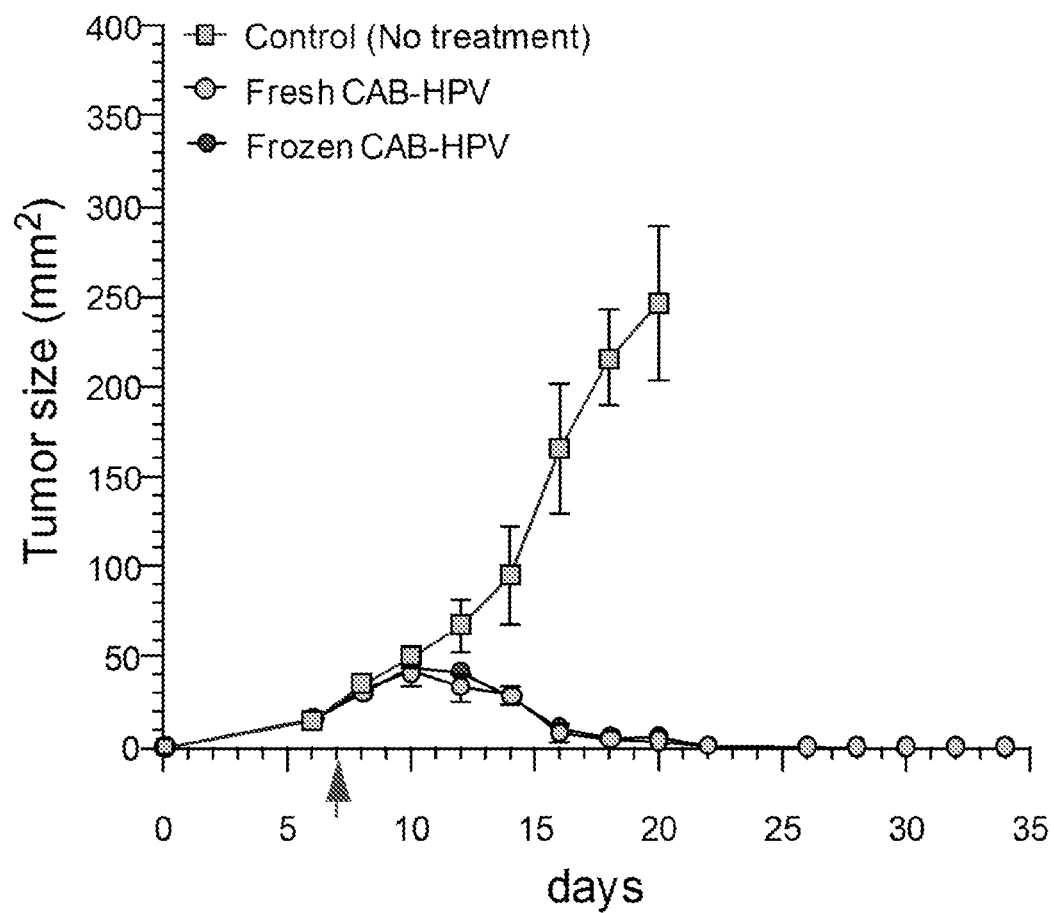
FIG. 25 shows that combination of FTY720 and cryopreserved CAB therapy significantly increases survival of mice bearing HPV-associated tumors. TC-1 cells (HPV18 E6/E7) were used ($2 \times 10^5$ tumor cells).

Specifically regarding CABs, *Chlamydia* spp. have the unique ability to induce selective polyclonal activation of resting B cells, easily obtained from peripheral blood or secondary lymphoid organs (e.g., lymph nodes), as well as from a wide variety of mammals (mouse, cats, dogs, rhesus macaques, and humans). Inactivated *Chlamydia* spp. elementary bodies (EB), reticulate bodies (RB), or their lysates are able to activate resting B cells obtained from peripheral blood or secondary lymphoid organs and induce their proliferation. This allows for their numbers to be expanded by significant amounts, which are further enhanced by additional factors, disclosed herein. This makes their subsequent immunomagnetic selection quite efficient. Their robust expansion also facilitates their utilization as an immunotherapy without antecedent selection processes. CABs can express high levels of costimulatory molecules, and are able to acquire soluble proteins and process them more efficiently than resting B cells. These requisites allow the generated CABs to be able to present antigens to T cells. The generated CABs can be used for autologous or allogenic infusion using various administration protocols, due to the ability of the platform to generate large numbers of APCs and the amenability of CABs to be cryopreserved and still maintain their full functionality as APCs, as shown in FIGS. 24 and 25.

Dendritic cells (DCs), belonging to the bone marrow-derived cell lineage, are present throughout the body in multiple tissues, and function as the central part of the mammalian immune system. Their main function is to process antigen material and present it on their surface to other cells of the immune system. Thus, DCs function as antigen-presenting cells (APCs).

DCs are present in tissues that are in direct contact with the external environment, such as the skin (where there is a specialized DC type called Langerhans cells) and the inner lining of the nose, lungs, stomach and intestines. They can also be found in an immature state (iDCs) in the blood. Once activated, they migrate to the lymph nodes where they interact with T cells and B cells to initiate and shape the adaptive immune response. DCs for therapeutic use can also be generated from differentiation of peripheral blood monocytes using a combination of cytokines, such as, but not limited to, GM-CSF and IL-4.

Antigens

The antigens disclosed herein for use with the platform can be any protein, peptide, whole inactivated organism, or any amine-containing molecule. Relevant antigens from a great number of diseases, disorders, or conditions may be used. Exemplary antigens include, but are not limited to, bacterial, viral, parasitic, allergens, autoantigens and tumor-associated antigens. If a DNA or RNA based vaccine is used, the antigen will typically be encoded by a sequence of the administered DNA or RNA construct. Alternatively, if antigen is administered as a conjugate, the antigen will typically be a protein comprised in the administered conjugate. The APCs disclosed herein can be exposed or crosslinked to more than one antigen simultaneously, or sequentially. For example, the APCs disclosed herein can be exposed to 2, 3, 4, 5, 6, or more antigens simultaneously or sequentially, or APCs loaded with different single antigens can be combined together for administration.

Specific examples of antigens that can be used include, but are not limited to, antigens from hepatitis A, B, C or D, Epstein-Barr virus, influenza virus, *Listeria, Clostridium botulinum*, tuberculosis, tularemia, Variola major (smallpox), viral hemorrhagic fevers, *Yersinia pestis* (plague), HIV, herpes, papilloma virus, and other antigens associated with infectious agents. Other antigens include antigens associated with autoimmune conditions, inflammatory conditions, allergy, asthma, and transplant rejection. Antigen-loaded APCs can be administered alone or in conjunction with other therapeutic agents, such as CD40 agonist or TLR agonists. As specific example, in conjunction with anti-CD40 antibody for use in therapeutic or prophylactic vaccines that treat disease conditions or enhancing immunity. In another example, the APC platform disclosed herein can be used in conjunction with checkpoint inhibitors. Examples of checkpoint inhibitor technology can be found in WO1999015157A2, WO2015016718A1, and WO2010149394A1, which are hereby incorporated in their entireties for their disclosure concerning checkpoint inhibitors. Other combination therapies are discussed herein as well.

In one embodiment, the antigen can comprise a tumor-related antigen. Examples of tumors that can be treated include the following: pancreatic tumors, such as pancreatic ductal adenocarinomas; lung tumors, such as small and large cell adenocarcinomas, squamous cell carcinoma, and bronchoalveolar carcinoma; colon tumors, such as epithelial adenocarcinoma and their metastases; and liver tumors, such as hepatoma and cholangiocarcinoma. Also included are HPV- and other virus-induced tumors; breast tumors, such as ductal and lobular adenocarcinoma; gynecologic tumors, such as squamous and adenocarcinoma of the uterine cervix, and uterine and ovarian epithelial adenocarcinoma; prostate tumors, such as prostatic adenocarcinoma; bladder tumors, such as transitional squamous cell carcinoma; tumors of the reticuloendothelial (RES) system, such as nodular or diffuse B or T cell lymphoma, plasmacytoma, and acute or chronic leukemia; skin tumors, such as malignant melanoma; and soft tissue tumors, such as soft tissue sarcoma and leiomyosarcoma. Of especial interest are brain tumors, such as astrocytoma, oligodendroglioma, ependymoma, medulloblastomas, and primitive neural ectodermal tumor. Included in this category are gliomas, glioblastomas, and gliosarcomas.

Specifically, the following antigens are associated with the following types of cancer, and can be used in the platforms and methods disclosed in Table 1:

TABLE 1

Cancers and Associated Antigens

| | |
|---|---|
| Melanoma | Tyrosinase, Tyrosinase-related protein (Trp-1), gp100, Melan/MART-1 |
| Prostate adenocarcinoma | Prostate-specific membrane antigen, Prostate-specific acid phosphatase, Prostate specific antigen |
| Pancreatic, lung, breast and colon adenocarcinoma | MUC1 |
| Non-small-cell lung carcinoma | MUC1, MAGE antigens, EGFR |
| Cancer/testis antigens | LAGE/NY-ESO1, MAGE antigens, CEA, AFP |
| Breast cancer | HER-2 |
| Acute myelogenous leukemia | Aurora-A kinase, BRAP, Cyclin A1, hTert, WT1 |
| Chronic lymphocytic leukemia | ROR1 |
| Chronic myelogenous leukemia | BCR/ABL, BRAP, CML28, CML66, PR1, Proteinase 3, survivin, WT1 |

The immune status of the treated individual may be any of the following: the individual may be immunologically naïve with respect to certain tumor-associated antigens present in the composition, in which case the compositions may be given to initiate or promote the maturation of an anti-tumor response. The individual may not currently be expressing anti-tumor immunity, but may have immunological memory, particularly T cell memory relating to a tumor-associated antigen comprised in the vaccine, in which case the compositions may be given to stimulate a memory response. The individual may also have active immunity (either humoral or cellular immunity, or both) to a tumor-associated antigen comprised in the vaccine, in which case the compositions may be given to maintain, boost, or maturate the response, or recruit other arms of the immune system. The subject should be at least partly immunocompetent, so that the vaccine can induce endogenous T cell responses.

In another embodiment, the antigen can comprise an infectious agent. Examples of infectious agents which can be treated using the platforms and methods disclosed herein include, but are not limited to, Influenza viruses, Respiratory Syncytial Virus (RSV), Human Papilloma Virus (HPV), Hepatitis B Virus (HBV), Hepatitis C Virus (HCV), Human T-Lymphotropic Virus Type-1, Human Immunodeficiency Virus 1 (HIV), Epstein-Barr Virus (EBV), Cytomegalovirus (CMV), and other Herpesviridae. Other examples include *Listeria monocytogenes, Salmonella, Mycobacterium tuberculosis, Plasmodium* sp. (Malaria), *Toxoplasma gondii*, and *Trypanosoma cruzi*.

Adjuvants

A wide variety of adjuvants may be used in accordance with the methods and compositions described herein. Examples adjuvants include, but are not limited to, a mineral salt, a saponin, a polysaccharide, a lipid, a lipopolysaccharide (endotoxin), a nucleic acid or a protein.

An adjuvant maybe a synthetic imidazoquinoline such as imiquimod (S-26308, R-837) (Harrison et al., Vaccine 19: 1820-1826 (2001)) or resiquimod (S-28463, R-848) (Vasilakos et al., Cellular Immunology 204: 64-74 (2000)).

An adjuvant may be a nucleic acid. Examples of nucleic acid adjuvants include, but are not limited to, CpG, polyadenylic acid/polyuridylic acid, polyinosinic:polycytidylic acid and Loxorbine (7-allyl-8-oxoguanosine) (see e.g., U.S. Pat. No. 6,406,705).

An adjuvant may be natural or synthetic MR1 ligands, such as vitamin B2 biosynthetic intermediates. Examples of these compounds include, but are not limited to, 5-amino-6-d-ribitylaminouracil (natural) or water stable synthetic MR1 ligands, such as compounds 9-11 derived as of 3c 5-OP-RU 3c (Mak, Nature Communications 2016).

An adjuvant may be a protein or protein fragment. Examples of protein adjuvants include hemocyanins, hemoerythrins, serum proteins, cytokines, macrophage inflammatory proteins, bacterial antigens, yeast antigens, mammalian polypeptides, and superantigens.

Adjuvants may be hemocyanins and hemoerythrins. An exemplary hemocyanin is from keyhole limpet (KLH), although other molluscan and arthropod hemocyanins and hemoerythrins may be employed. In another exemplary embodiment, a protein adjuvant may be *bacillus* calmette guerin (BCG).

A protein adjuvant may be a serum protein, such as, for example, complement factor C3d. C3d is a 16 amino acid peptide (See, e.g., Fearon et al., 1998, Semin. Immunol. 10: 355-61; Nagar et al., 1998, Science; 280(5367):1277-81, Ross et al. 2000, Nature Immunol., Vol. 1(2)) which is available commercially (e.g., Sigma Chemical Company Cat. C 1547).

A protein/peptide adjuvant may be a bacterial or yeast antigen. Examples of suitable bacterial or yeast antigens include, for example, muramyl peptides (such as, Immther™ theramide (MDP derivative), DTP-N-GDP, GMDP (GERBU adjuvant), MPC-026, MTP-PE, muramyl etide, and murapalmitine); MPL derivatives (such as, MPL-A, MPL-SE, 3D-MLA, and SBAS-2); mannon, N-acetyl-muramyl-L-threonyl-D-isoglutamine (thr-MDP), N-acetyl-nor-muramyl-L-alanyl-D-isoglutamine (nor-MDP), and N-acetylmuramyl-L-alanyl-D-isoglutaminyl-L-alanine-2-(1'-2'-dipalmitoyl-sn-glycero-3-hydroxyphosphoryloxy)-ethylamine (MTP-PE). Such agents are commercially available, for example, MPL-A may be obtained from ICN Chemical Company (Cat #150012) and Immther™ may be obtained from Dor Pharma Inc.

A protein adjuvant may be a mammalian peptide. Examples of mammalian peptides that may be used as adjuvants include, for example, melanoma peptide 946, neutrophil chemo-attractant peptide, and elastin repeating peptide.

An adjuvant may be a superantigen. Superantigens may be particularly useful for generating or enhancing the immune response against intracellular antigens, including intracellular tumor antigens. Superantigens are bacterial products that stimulate a greater proportion of T lymphocytes than peptide antigens without a requirement for antigen processing (Mooney et. al., (1994), Mol. Immunol. 31: 675-681). Superantigens include *Staphylococcus* exoproteins, such as the alpha, beta, gamma and delta enterotoxins from *S. aureus* and *S. epidermidis*, and the alpha, beta, gamma and delta *E. coli* exotoxins, and other membrane proteins and toxins from bacteria such as *Clostridium perfringens* and *Streptococcus pyogenes*. In other embodiments, an adjuvant may be a polysaccharide. Various polysaccharide adjuvants may also be used, such as, for example, pneumococcal polysaccharide adjuvants (see e.g., Yin et al., (1989) J. Biological Response Modifiers 8: 190-205). Polyamine varieties of polysaccharides, such as chitin and chitosan, and deacetylated chitin, may also be used.

Adjuvant may also be a lipopolysaccharide (endotoxin). This class of adjuvants may be exemplified by lipid A, which may be used in animals, and detoxified endotoxins, which may be used in animals and humans. Detoxified and refined endotoxins, and combinations thereof, are described in U.S. Pat. Nos. 4,866,034; 4,435,386; 4,505,899; 4,436,727; 4,436,728; 4,505,900.

Adjuvants may also be teichoic acids from Gram negative cells. These include the lipoteichoic acids (LTA), ribitol teichoic acids (RTA) and glycerol teichoic acid (GTA). Active forms of their synthetic counterparts may also be employed (Takada et al., (1995) Infection and Immunity 63: 57-65)). BCG and BCG-cell wall skeleton (CWS) may also be used as adjuvants, with or without trehalose dimycolate. Trehalose dimycolate may be used itself. Trehalose dimycolate may be prepared as described in U.S. Pat. No. 4,579,945. Adjuvants described herein are commercially available, or can be obtained using conventional methods well-known in the art.

Additional Platform Factors

As mentioned above, the platform described herein can also include other factors. These factors include, but are not limited to, 1-ethyl 1-3-(3-dimethylaminopropyl)-carbodiimide (EDAC), cycloheximide (CHX), and α-galactosylceramide (α-GalCer) or an equivalent. EDAC, CHX, and α-GalCer (or other equivalent adjuvants, which are discussed below) can be used together or individually with the platform comprising FTY720, Flt-3L and/or GM-CSF.

A protein or peptide antigen can be cross-linked to an APC with EDAC, or any other reagent capable of cross-linking. A cross-linker such as EDAC can greatly enhance the antigen presenting ability of APCs. This can be done prior to in vivo administration of the APC, as in the following example: chemical conjugation of peptide to *Chlamydia* activated B cells (CABs) with EDAC increases antitumor therapeutic activity compared to simple peptide pulsing/loading of CABs. Any known cross-linker can be used, as long as it is non-cytotoxic to the APCs. In a specific example, APCs are re-suspended in PBS (pH 6.0) at a concentration of $10^8$-$2.5 \times 10^8$ cells/ml. Amine-containing antigen is added (protein or peptide), and then fresh EDAC is added for a final concentration of 25.65 mg/ml. Mixture is well mixed, and incubated on ice for 1 hour. After incubation, APCs are washed with PBS (pH 7.4).

The APCs can also be treated with cycloheximide (CHX) prior to being cross-linked with the antigen. This can be used to boost antigen presenting capacity, such as activated B cells. Cycloheximide is an inhibitor of protein biosynthesis in eukaryotic organisms, produced by the bacterium *Streptomyces griseus*. Cycloheximide exerts its effect by interfering with the translocation step in protein synthesis (movement of 2 tRNA molecules and mRNA in relation to the ribosome) thus blocking translational elongation. Typically, CHX is added to APCs at a final concentration of 2.5 μg/ml and then incubated for 45-60 minutes. APCs are washed after this step with PBS (pH 7.4) before APCs are used or conjugated with antigen.

The APCs can also be exposed to an adjuvant, such as α-galactosylceramide (α-GalCer) or an equivalent, such as α-C-GC, C18, C22, C23, 7DW8-5, 7DW8-6, α-GC C24:0, or α-Carba-GC. Examples of this can be seen in FIGS. 12, 22 and 23. Other NKT cell activators can also be used. Examples include, but are not limited to, α-C-galactosylceramide (Fujii, PNAS 2006). Also, α-GalCer can be combined with another activator of other types of natural killer T (NKT) cells such as lysophosphatidylcholine or β-mannosylceramide. Lysophosphatidylcholine or β-mannosylceramide can also be used alone as the adjuvant. The use of natural or synthetic MR1 ligands, such as vitamin B2 biosynthetic intermediates, can also be considered. For example, CABs can be loaded with 5-amino-6-d-ribitylaminouracil alone or in conjunction with α-GalCer. Addition of other adjuvants, such as TLR ligands (e.g. polyinosinic: polycytidylic acid), and STING ligands, can also be performed alone or in conjunction with α-GalCer.

α-GalCer is described by Nattori, et al., Tetrahedron, 50:2271 (1994), incorporated by reference, has itself been shown to inhibit tumor growth. See, Koejuka, et al., Recent Res. Cancer, 1:341 (1999). Sharif, et al., Nature Med., 7:1057 (2001), and Hong, et al., Nature Med., 7:1052 (2002). Study of the structure of α-GalCer shows that it contains a sphingosine chain. Truncation of this chain has been shown, by Miyamoto, et al., Nature, 413:531 (2001), to result in a compound preventing autoimmune encephalomyelitis. In parallel work it was shown that NKT cells recognize lipid antigens that are presented by the major histocompatibility complex-class I like protein, CD1d, for example. See, Godfrey et al., J. Clin. Invest., 114:1379-1388 (2004). Singh, et al., J. Immunol., 163:2373 (1999), and Burdin, et al., Eur. J. Immunol., 29:2014 (1999), have shown that αGalCer and CD1d potentiate Th2-mediated, adaptive immune responses, via activation of Vα14 natural killer T (NKT) cells.

α-GalCer has been developed as a potential therapeutic compound and taken into clinical testing, see, for example, Giaccone et al., Clin Canc. Res., 8, 3702-3709 (2002). However, following treatment with α-GalCer, NKT cells in the peripheral blood of treated cancer patients treated fell to undetectable levels within 24 hours of treatment and failed to regain pretreatment levels for the duration of the study. Effects that are avoided when α-GalCer is administered as cell-associated (as described in these methods), for example, Chang, et al, J Exp Med, 201:1503 (2005). Chung, et al, Cancer Res, 66:6843 (2006).

Various publications describe synthesis of α-GalCer and its derivatives, which are herein incorporated by reference in their entirety. An exemplary, but by no means exhaustive list of such references includes Morita, et al., J. Med. Chem., 38:2176 (1995); Sakai, at al., J. Med. Chem., 38:1836 (1995); Morita, et al., Bioorg. Med. Chem. Lett., 5:699 (1995); Takakawa, et al., Tetrahedron, 54:3150 (1998); Sakai, at al., Org. Lett., 1:359 (1998); Figueroa-Perez, et al., Carbohydr. Res., 328:95 (2000); Plettenburg, at al., J. Org. Chem., 67:4559 (2002); Yang, at al., Angew. Chem., 116: 3906 (2004); Yang, at al., Angew. Chem. Int. Ed., 43:3818 (2004); and, Yu, et al., Proc. Natl. Acad. Sci. USA, 102(9): 3383-3388 (2005).

The addition of EDAC, CHX, and α-GalCer, or their equivalents thereof, each independently or in all possible combinations, can be used to increase the effectiveness of the platforms and methods described herein, but are not necessary for their effectiveness.

Administration and Vaccines

GM-CSF and Flt-3L can be administered individually, or in combination with each other. GM-CSF, for example can be present in an amount to be administered of 2 μg/kg or less. The amount of GM-CSF to be administered can be determined based on a variety of patient-specific factors. GM-CSF can be administered at a range of 0.5 to 2.0 μg/kg or less. Therefore, the amount to be administered can be 2.0, 1.9, 1.8, 1.7, 1.6, 1.5, 1.4, 1.3, 1.2, 1.1. 1.0, 0.9, 0.8, 0.7, 0.6, 0.5, 0.4, 0.3, 0.2, or 0.1 μg/kg, or any amount below, above, or in-between these amounts.

Flt-3L, for example, can be administered at a range of 2.0 to 8.0 μg/kg or less. Thus, the amount to be administered can be 8.0, 7.5, 7.0, 6.5, 6.0, 5.5, 5.0, 4.5, 4.0, 3.5, 3.0, 2.5, 2.0, 1.5, 1.0, or 0.5 μg/kg, or any amount below, above, or in-between these amounts.

GM-CSF, FTY720, and Flt-3L can be administered before, simultaneously with and/or after administration of the APCs. Preferably GM-CSF and Flt-3L are administered before administration of the APCs. They can be administered 1, 2, 3, 4, 5, 6, or 7 or more days prior to treatment with APCs. They can be administered in a variety of ways known to those of skill in the art. The cytokines can also be combined with other cytokines that have been found to be effective for increasing APC effectiveness. In one example, GM-CSF and Flt-3L can be used in a controlled, prolonged-release formula. Such formulas are known in the art. For FTY720, it is preferably administered after administration of the APCs. It can be administered 1, 2, 3, 4, 5, 6, or 7 or more days after to treatment with APCs. It can be administered in a variety of ways known to those of skill in the art. In one example, FTY720 can be used in a controlled, prolonged-release formula. Such formulas are known in the art.

In one specific example, a cancer patient undergoing treatment would be treated with the following protocol. By way of example, the patient first provides peripheral blood, usually around 500 ml, that would be used to generate APCs over the course of 5-30 days (depending on the type of APC). Then the patient would receive 3 days of cytokine combination treatment (i.e., low dose Flt-3L and GM-CSF), administered subcutaneously, before APC administration. APCs are prepared for antigen loading the day before by incubating them with the selected adjuvant (e.g. α-GalCer) and the selected antigen (if antigen is a protein or a polypeptide). On the day of administration, APCs are treated with CHX and conjugated with EDAC (if peptides are used). The patient then receives intravenous APCs (CABs, DCs, CD40-activated B cells) infusion (if CABs are being used). Cytokine combination treatment precedes APC administration so that it can stimulate in vivo generation of host DCs and also decrease the proportion of myeloid derived suppressor cells (MDSCs). FTY720 is given 2 hours after administration of APCs. Treatment can be repeated in as many as cycles as needed to induce antigen-specific T cell responses.

The compositions disclosed herein can be administered individually, or in combination with each other. They can be combined with other cytokines, antibodies, or compounds known to increase the effectiveness of APCs or treatment of the subject.

Disclosed herein is a vaccine created using the platform disclosed herein. Specifically, disclosed herein is a cell-based vaccine for ex vivo immunization, as well as compositions and methods for in vivo immunization to elicit an immune response directed against an antigen. In one embodiment, disclosed is a subject with a type of cancer which expresses a tumor-specific antigen. This can result in an improved therapeutic outcome for the patient, evidenced by, e.g., a slowing or diminution of the growth of cancer cells or a solid tumor which expresses the tumor-specific antigen or a reduction in the total number of cancer cells or total tumor burden. In a related embodiment, the patient has been diagnosed as having a viral, bacterial, fungal or other type of infection (or a viral-induced tumor) associated with expression of a particular antigen, e.g., a viral antigen. This vaccine can result in an improved therapeutic outcome for the patient as evidenced by a slowing in the growth of the causative infectious agent within the patient and/or a decrease in, or elimination of, detectable symptoms typically associated with the particular infectious disease.

The antibodies, cytokines, and compounds disclosed herein can be formulated according to known methods used to prepare pharmaceutically useful compositions. They can be combined in admixture, either as the sole active material or with other known active materials, with pharmaceutically suitable diluents (e.g., Tris-HCl, acetate, phosphate), preservatives (e.g., Thimerosal, benzyl alcohol, parabens), emulsifiers, solubilizers, adjuvants and/or carriers. Suitable carriers and their formulations are described in Remington's Pharmaceutical Sciences, 16th ed. 1980, Mack Publishing Co. In addition, such compositions can be complexed with polyethylene glycol (PEG), metal ions, or incorporated into polymeric compounds such as polyacetic acid, polyglycolic acid, hydrogels, etc., or incorporated into liposomes, microemulsions, micelles, unilamellar or multilamellar vesicles, erythrocyte ghosts or spheroblasts. Such compositions will influence the physical state, solubility, stability, rate of in vivo release, and rate of in vivo clearance of the cytokines.

The antibodies and compounds disclosed herein can be administered topically, parenterally, or by inhalation. The term "parenteral" includes subcutaneous injections, intravenous, intramuscular, intracisternal injection, or infusion techniques. These compositions will typically contain an effective amount of the compound, alone or combined with an effective amount of another active material, e.g. those described above. They can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

In general, water, suitable oil, saline, aqueous dextrose (glucose), and related sugar solutions and glycols such as propylene glycol or polyethylene glycols are suitable carriers for parenteral solutions. Solutions for parenteral administration contain the active ingredient, suitable stabilizing agents and, if necessary, buffer substances. Antioxidizing agents such as sodium bisulfate, sodium sulfite or ascorbic acid, either alone or combined, are suitable stabilizing agents. Also used are citric acid and its salts and sodium ethylenediaminetetraacetic acid (EDTA). In addition, parenteral solutions can contain preservatives such as benzalkonium chloride, methyl- or propyl-paraben and chlorobutanol. Suitable pharmaceutical carriers are described in Remington's Pharmaceutical Sciences, a standard reference text in this field. Additionally, standard pharmaceutical methods can be employed to control the duration of action. These are well known in the art, and include controlled release preparations and can include appropriate macromolecules, for example polymers, polyesters, polyamino acids, polyvinyl, pyrolidone, ethylenevinylacetate, methyl cellulose, carboxymethyl cellulose or protamine sulfate. The concentration of macromolecules as well as the methods of incorporation can be adjusted in order to control release. Additionally, the agent can be incorporated into particles of polymeric materials such as polyesters, polyamino acids, hydrogels, poly (lactic acid) or ethylenevinylacetate copolymers. In addition to being incorporated, these agents can also be used to trap the compound in microcapsules.

Pharmaceutical formulations containing the therapeutic agents disclosed herein can be prepared by procedures known in the art using well known and readily available ingredients. The therapeutic agents can also be formulated as solutions appropriate for parenteral administration, for instance by intramuscular, subcutaneous or intravenous routes. The pharmaceutical formulations of the therapeutic agents can also take the form of an aqueous or anhydrous solution or dispersion, or alternatively the form of an emulsion or suspension.

The various components of the cellular vaccine are present in an "effective combination", which means that there are sufficient amounts of each of the components for the vaccine to be effective. Any number of component cells or other constituents may be used, as long as the vaccine is effective as a whole. This will also depend on the method used to prepare the vaccine.

The pharmaceutical compositions may be given following, preceding, in lieu of, or in combination with, other therapies relating to generating an immune response or treating cancer in the subject. For example, the subject may previously or concurrently be treated by surgical de-bulking, chemotherapy, radiation therapy, checkpoint inhibitors, and other forms of immunotherapy and adoptive transfer. Where such modalities are used, they are preferably employed in a way or at a time that does not interfere with immunogenicity of the compositions disclosed herein. The subject may also have been administered another vaccine or other composition in order to stimulate an immune response. Such alternative compositions may include tumor antigen vaccines, nucleic acid vaccines encoding tumor antigens, anti-idiotype vaccines, and other types of cellular vaccines, including cytokine-expressing tumor cell lines.

Disclosed herein are combination therapies, comprising administration of a cellular vaccine described herein in conjunction with another strategy designed to enhance an anti-tumor immunological responses. In one combination therapy, the subject is given an intra-tumor implant, either before, during, or after treatment at a site distant from the tumor with a composition comprising the APCs disclosed herein. In another combination therapy, the subject is treated at sites distant from the tumor with an alternative cellular vaccine composition, either before, during, or after treatment with the antigen-loaded APCs disclosed herein. In another combination therapy, the subject is given checkpoint inhibitors. Where a plurality of different compositions or modes of administration are employed throughout the course of therapy, the order and timing of each element of treatment is chosen to optimize immunostimulatory and anti-tumor effects.

Production Methods

Any of a variety of culture media may be used in the present methods as is known to the skilled person (see e.g., Current Protocols in Cell Culture, 2000-2009 by John Wiley & Sons, Inc.). In one embodiment, media for use in the methods described herein includes, but is not limited to modified Dulbecco medium (with or without fetal bovine or other appropriate serum). Illustrative media also includes, but is not limited to, IMDM, RPMI 1640, AIM-V, DMEM, MEM, a-MEM, F-12, X-Vivo 15, and X-Vivo 20. In further embodiments, the medium may comprise a surfactant, an antibody, plasmanate or a reducing agent (e.g. N-acetylcysteine, 2-mercaptoethanol), or one or more antibiotics. In some embodiments, IL-2, IL-4, IL-6, IL-10, agonist anti-CD40 monoclonal antibody, soluble CD40L and a crosslinking enhancer, or irradiated tCD40L NIH/3T3 cells may also be used. B cells may be cultured under conditions and for sufficient time periods to achieve activation desired. In certain embodiments, the B cells are cultured under conditions and for sufficient time periods such that 10%, 15%, 20%, 25%, 30%, 35%, 40%, 45%, 50%, 55%, 60%, 65%, 70%, 75%, 80%, 85%, 90%, 95%, or even 100% of the B cells are activated as desired.

Maturation and activation status of APCs can be assessed by their expression of costimulatory molecules using flow cytometric assays. After culture for an appropriate period of time, such as from 2, 3, 4, 5, 6, 7, 8, 9, or more days, generally around 3 days, an additional volume of culture medium, containing fresh cytokines if needed, may be added.

In one embodiment, in particular, CABs and CD40-activated B cells can be contacted or cultured on feeder cells. In other embodiments, the culture system described herein is carried out in the absence of feeder cells, providing advantages over other systems known in the art that require feeder cells. Where feeder cells may be used, the feeder cells are a stromal cell line, e.g., the murine stromal cell lines S17 or MS5. In a further embodiment, purified $CD19^+$ cells may be cultured in the presence of fibroblasts expressing CD40-ligand in the presence of B cell activating factor cytokines such as IL-10 and IL-4. CD40L bound to a surface such as tissue culture plate or a bead may also be provided. In another embodiment, purified B cells may be cultured in presence or absence of feeder cells, with CD40L or agonist anti-CD40 monoclonal antibody, and in presence of one or more cytokines or factors selected from IL-10, IL-4, IL-7, p-ODN, CpG DNA, IL-2, IL-15, IL6, IFN-α, and IFN-δ. In another embodiment, dendritic cells can be matured using TLR ligands, such as CpG and poly I:C, and/or cytokines, such as IFN-γ, and/or CD40L or agonist anti-CD40 monoclonal antibody.

Any of the APCs indicated above could be loaded with antigen (e.g. protein or peptide) by simple loading or by crosslinking, then loaded with an adjuvant (e.g. α-GalCer, or natural or synthetic MR1 ligand, or a TLR or STING ligand). After incubation overnight, the loaded APCs can be treated with CHX before preparation of cells for administration.

The platform can be carried out either ex vivo or in vivo, in whole or in part. "Ex vivo" refers to methods conducted within or on cells or tissue in an artificial environment outside an organism with minimum alteration of natural conditions. In contrast, the term "in vivo" refers to a method that is conducted within living organisms in their normal, intact state, while an "in vitro" method is conducted using components of an organism that have been isolated from its usual biological context. For example, CABs can be generated by exposure of resting B cells to inactivated or live *Chlamydia* spp. (including *C. trachomatis, C. psittaci, C. pneumoniae* and *C. muridarum*) or peptide or fragment thereof in vivo, or peptide thereof ex vivo. The expanded B cells are then exposed or crosslinked to an antigen so that they may uptake it accordingly. Again, this can take place in vivo or ex vivo. For example, the antigen may be directly injected into a subject, or B cells of the subject can be exposed or crosslinked to the modified antigen in vitro (ex vivo), with the expanded, activated B cells then returned to the subject. The CABs can be used, for example, in direct in vivo administration, ex vivo somatic therapy, in vivo implantable devices and ex vivo extracorporeal devices.

A number of embodiments of the invention have been described. Nevertheless, it will be understood that various modifications may be made without departing from the spirit and scope of the invention. Accordingly, other embodiments are within the scope of the following claims.

EXAMPLES

Figure 27:
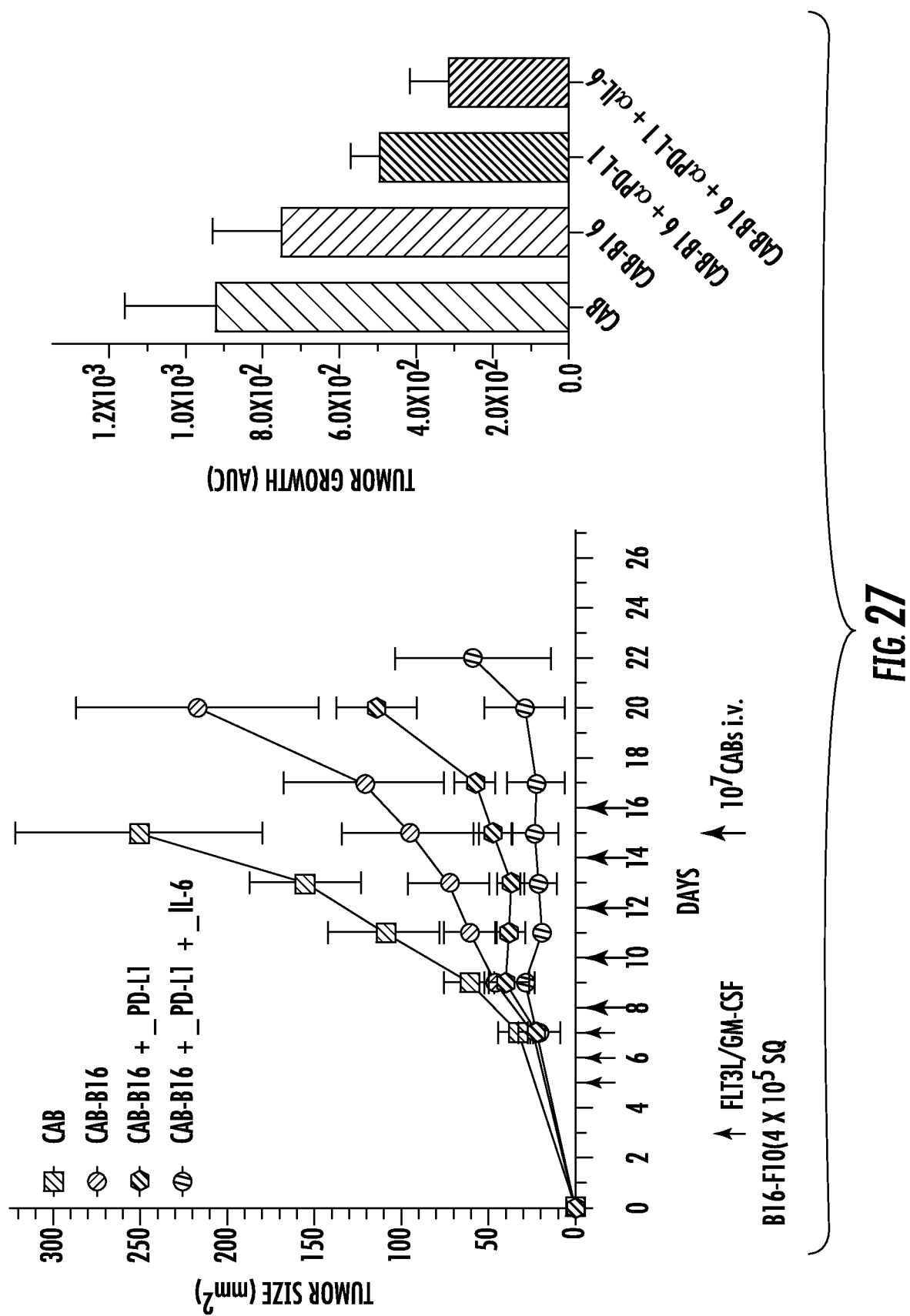
FIG. 27 shows that the addition of anti-IL6 mAb significantly increases antitumor therapeutic activity of CAB and anti-PDL-1 mAb combination therapy. Day 0: SQ administration of $4 \times 10^5$ B16-F10 melanoma cells (very high tumor burden of an aggressive tumor cell line). Administration of CABs conjugated with B16-specific peptides and loaded with α-GC was started on day 8.
Figure 28:
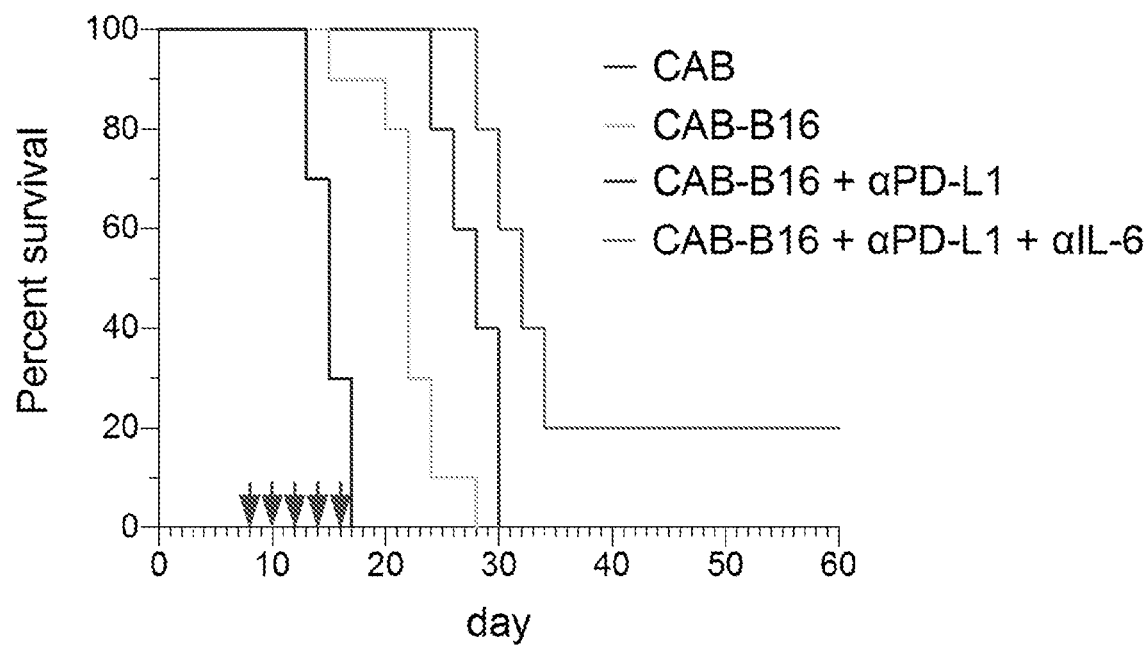
FIG. 28 shows the addition of anti-IL6 mAb to CAB and anti-PDL-1 mAb combination therapy significantly increases survival of treated animals. Day 0: SQ administration of $4 \times 10^5$ B16-F10 melanoma cells (very high tumor burden of an aggressive tumor cell line were used).

Example 1: Addition of Anti-IL6 mAb Significantly Increases Antitumor Therapeutic Activity of CAB and Anti-PDL-1 mAb Combination Therapy Using a very aggressive tumor model (i.e., B16-F10 melanoma), in which a very high dose of tumor cells ($4 \times 10^5$)

was administered, clear synergism between CAB therapy and anti-PDL-1 mAb was seen (of note, anti-PD-1 could alternatively be used). Interestingly, when anti-IL-6 was added to this combination therapy, a significant increase in antitumor activity was detected (as demonstrated by a decreased tumor burden and increased survival in the group treated with the addition of anti-IL-6), as shown in FIGS. 27 and 28. For these studies, Anti-PDL-1 mAb alone, or in combination with anti-IL-6 mAb, was given every other day for a total of 7 doses starting on day 8 after tumor injection (i.e. concomitant with CAB therapy for the first 5 doses). It appears that the addition of anti-IL-6 mAb can decrease deleterious inflammatory responses triggered by CAB and anti-PDL-1 combination therapy, without affecting the boost of the tumor-specific CD8$^+$ T cell response induced by the combination therapy. Combining anti-PDL1 mAb with anti-IL-6 mAb can have a synergistic effect if used earlier in tumor treatment, even if CAB therapy is not used.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

Figure 20:
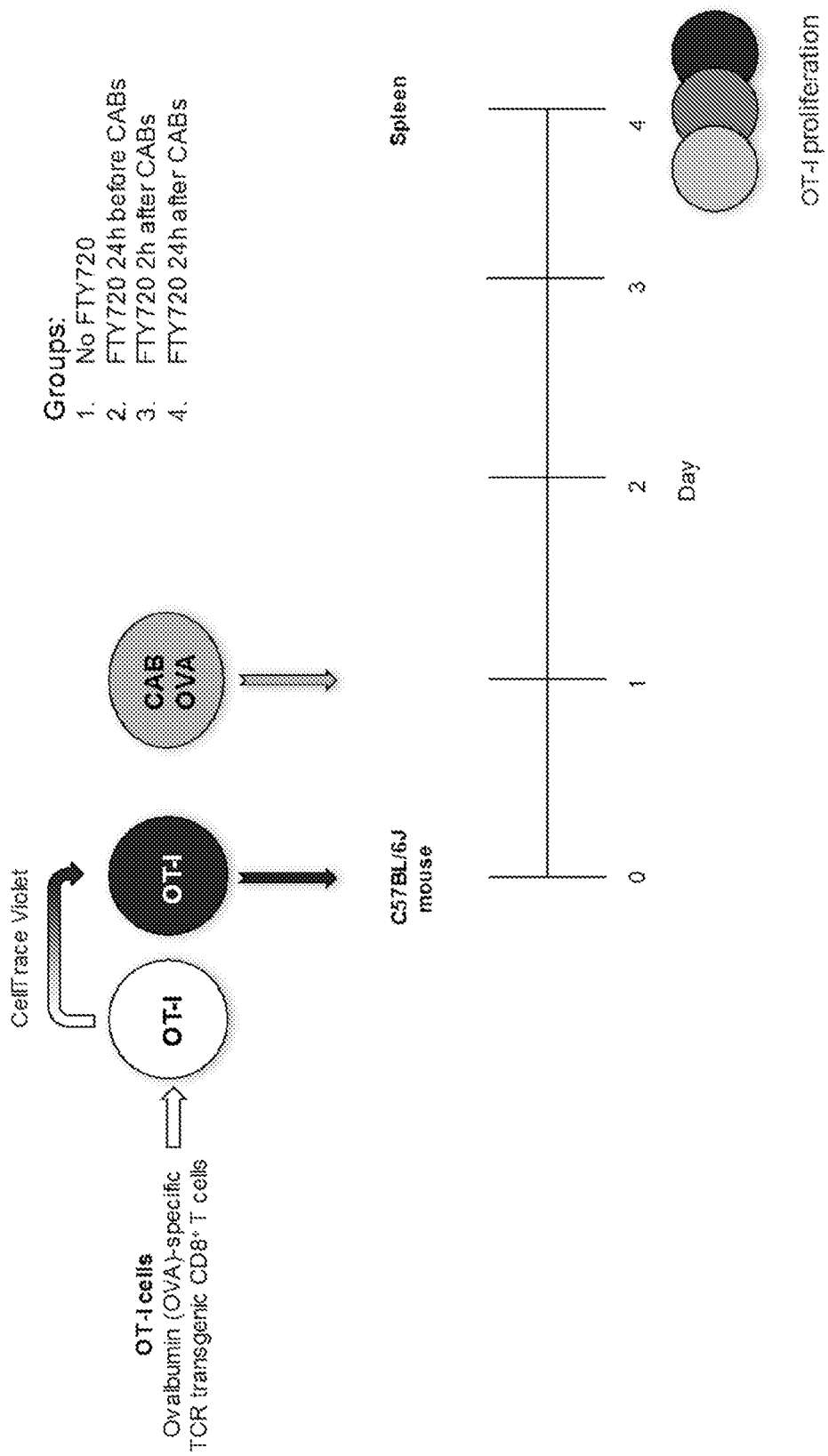
FIG. 20 shows the method to assess effect of FTY720 on CAB-mediated $CD8^+$ T cell priming.
Figure 21:
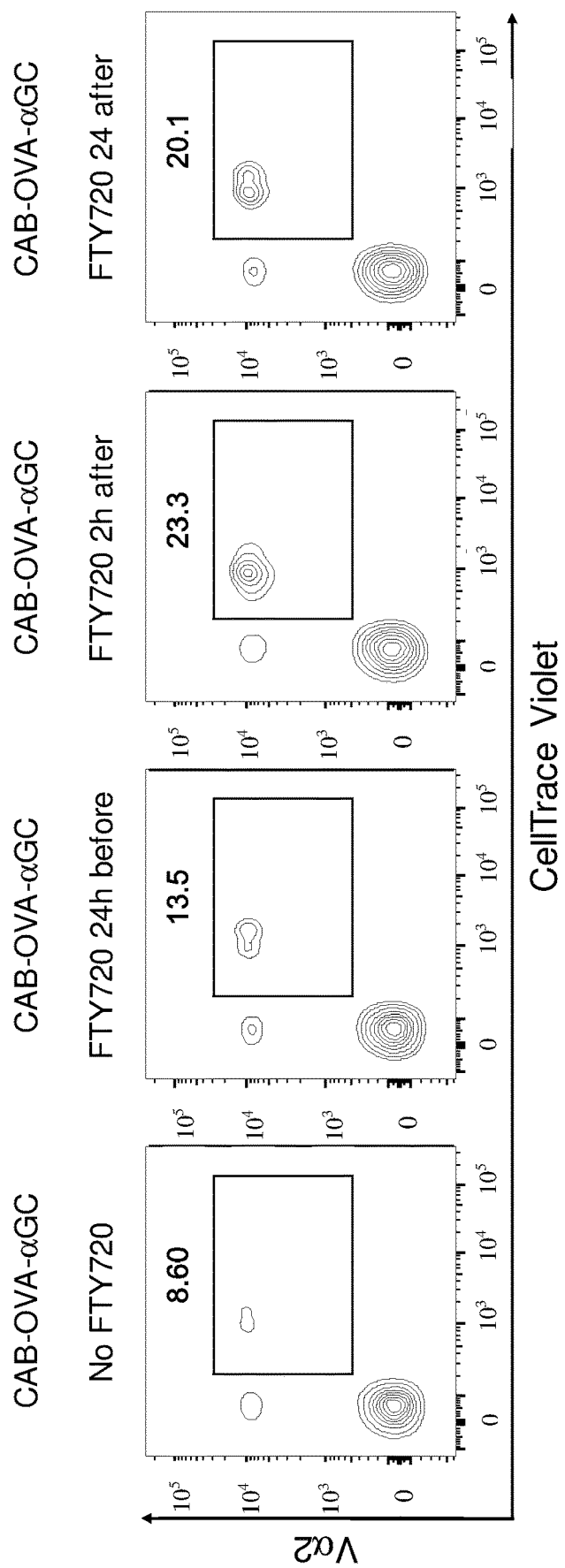
FIG. 21 shows that FTY720 increases the ability of CABs loaded with α-GC to prime robust $CD8^+$ T cells responses.
Figure 22:
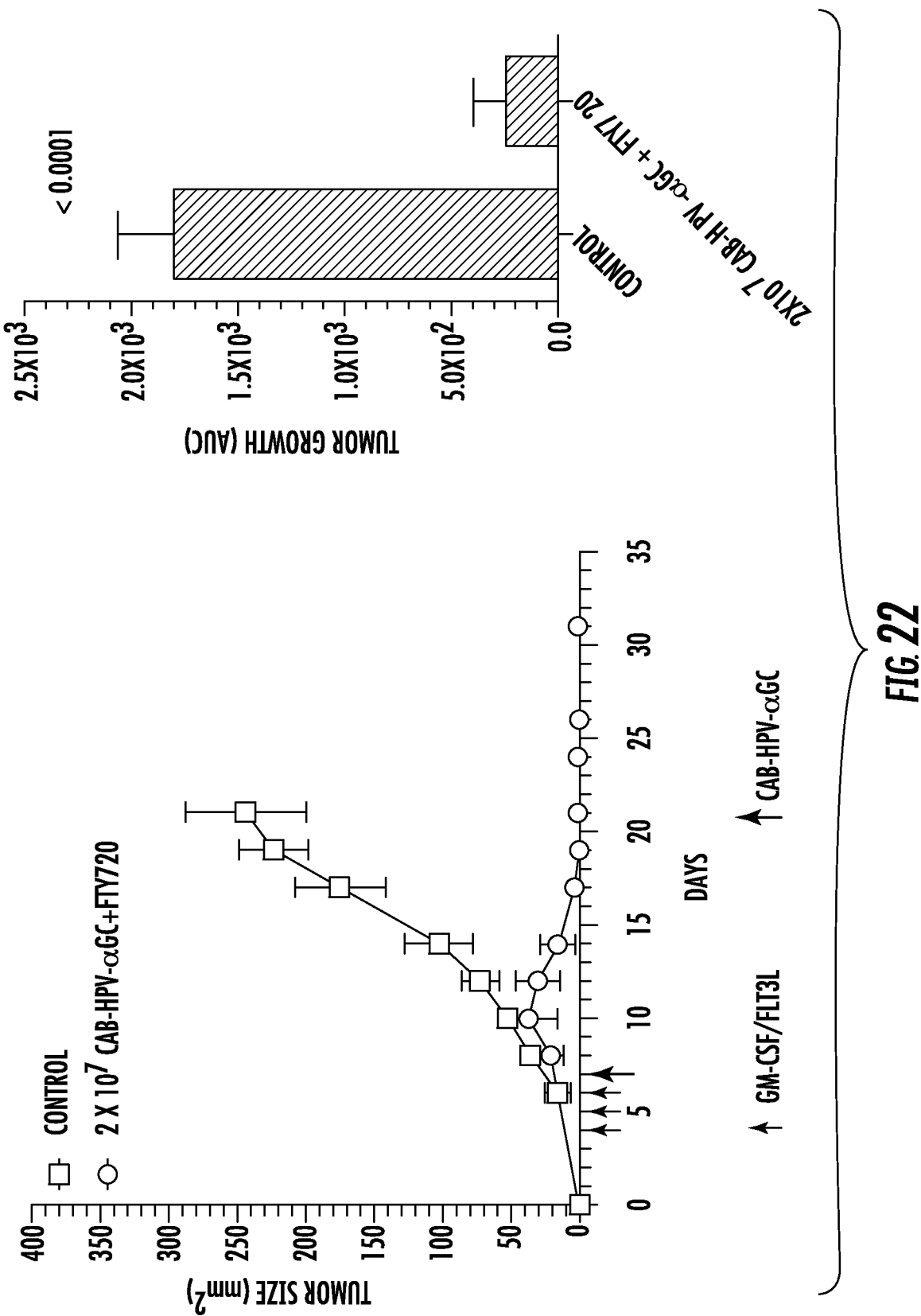
FIG. 22 show the ability of FTY720 in combination with CAB therapy to treat HPV-associated tumors. TC-1 cells (HPV18 E6/E7) were used ($2 \times 10^5$ tumor cells).
Figure 23:
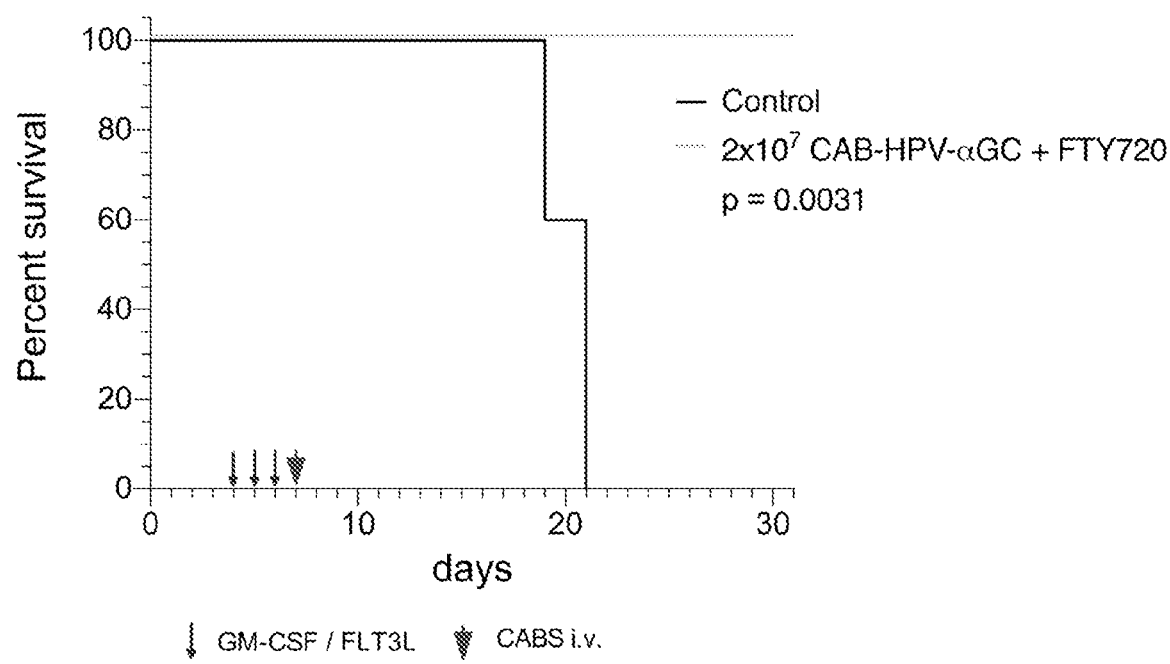
FIG. 23 shows combination of FTY720 and CAB therapy significantly increases survival of mice bearing HPV-associated tumors. TC-1 cells (HPV18 E6/E7) were used ($2 \times 10^5$ tumor cells).

Example 2: Addition of FTY720 Significantly Increases Priming of Antigen-Specific CD8$^+$ T Cells and Antitumor Therapeutic Activity of CABs Therapy This examples uses the experimental system depicted in FIG. 20, in which fluorescently-labeled ovalbumin-specific TCR-transgenic CD8$^+$ T cells were transferred into naïve C57BL/6 mice one day before infusion of CABs loaded with ovalbumin and α-GC. As indicated, these mice were also treated with FTY720 or vehicle. The data shown in FIG. 21 demonstrates that administration of FTY720 significantly increases the ability of CAB therapy to activate and induce proliferation of antigen-specific CD8$^+$ T cells in vivo. Furthermore, as shown in FIGS. 22 and 23, the addition of FTY720 to single dose CAB therapy led to the complete rejection of tumor in this murine model of HPV-associated tumor.

Figure 18:
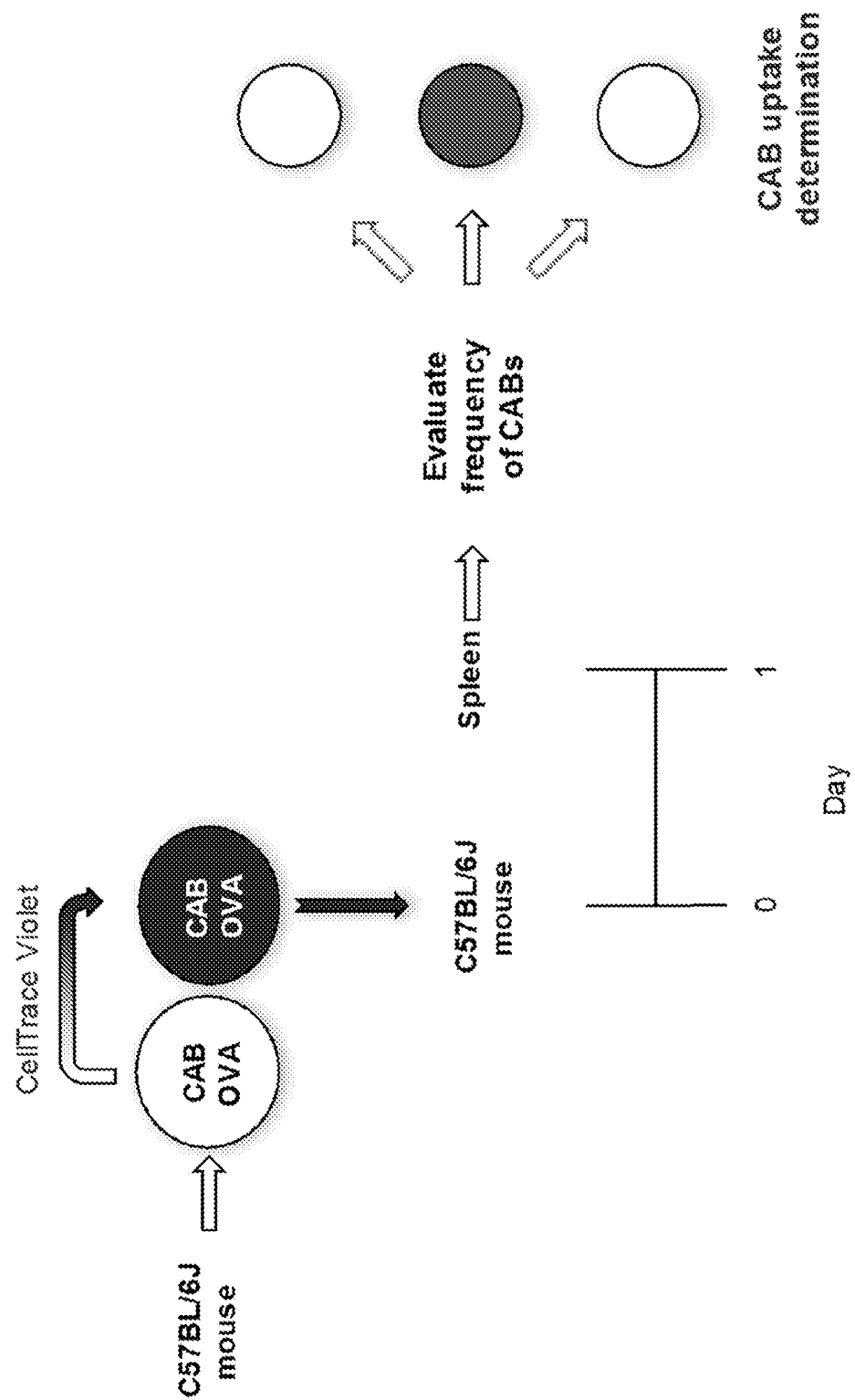
FIG. 18 shows the method to assess effect of FTY720 on CAB frequency in a host's spleen.
Figure 19:
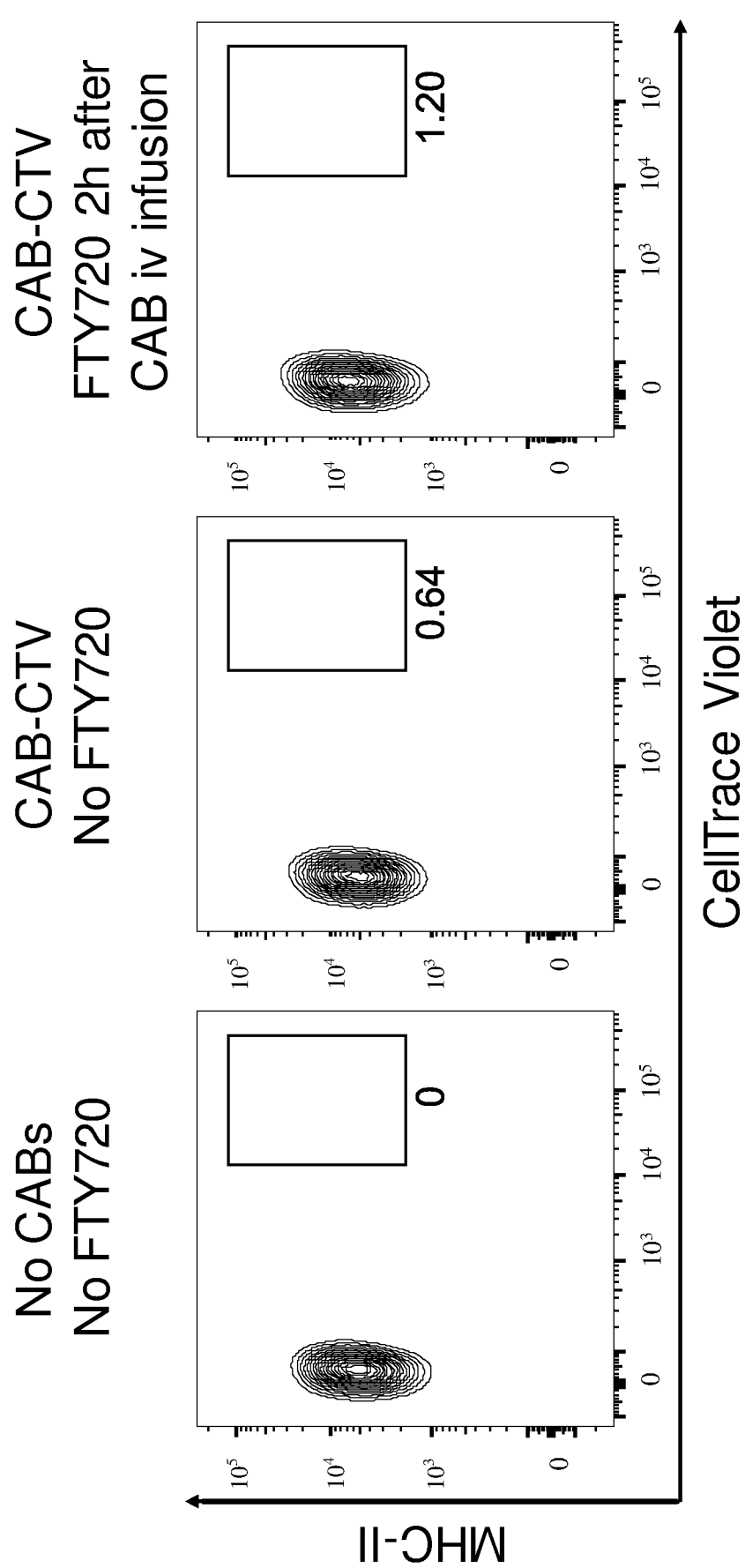
FIG. 19 shows FTY720 promotes CAB accumulation in a host's spleen. CAB-CTV denotes CABs labeled with CellTrace Violet™. FTY720 was used at 1.25 mg/kg.

It appears that the addition of FTY720 increases the frequency of CABs in secondary lymphoid organs, such as the spleen (FIGS. 18 and 19), increasing the amount of antigen available for priming of antigen-specific CD8$^+$ T cells. It may also increase the retention of CD8$^+$ T cells in secondary lymphoid organs, increasing the likelihood of activation of antigen-specific CD8$^+$ T cells.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize or ascertain using no more than routine experimentation, many equivalents to the specific embodiments of the invention described herein. Such equivalents are intended to be encompassed by the following claims.

Figure 29:
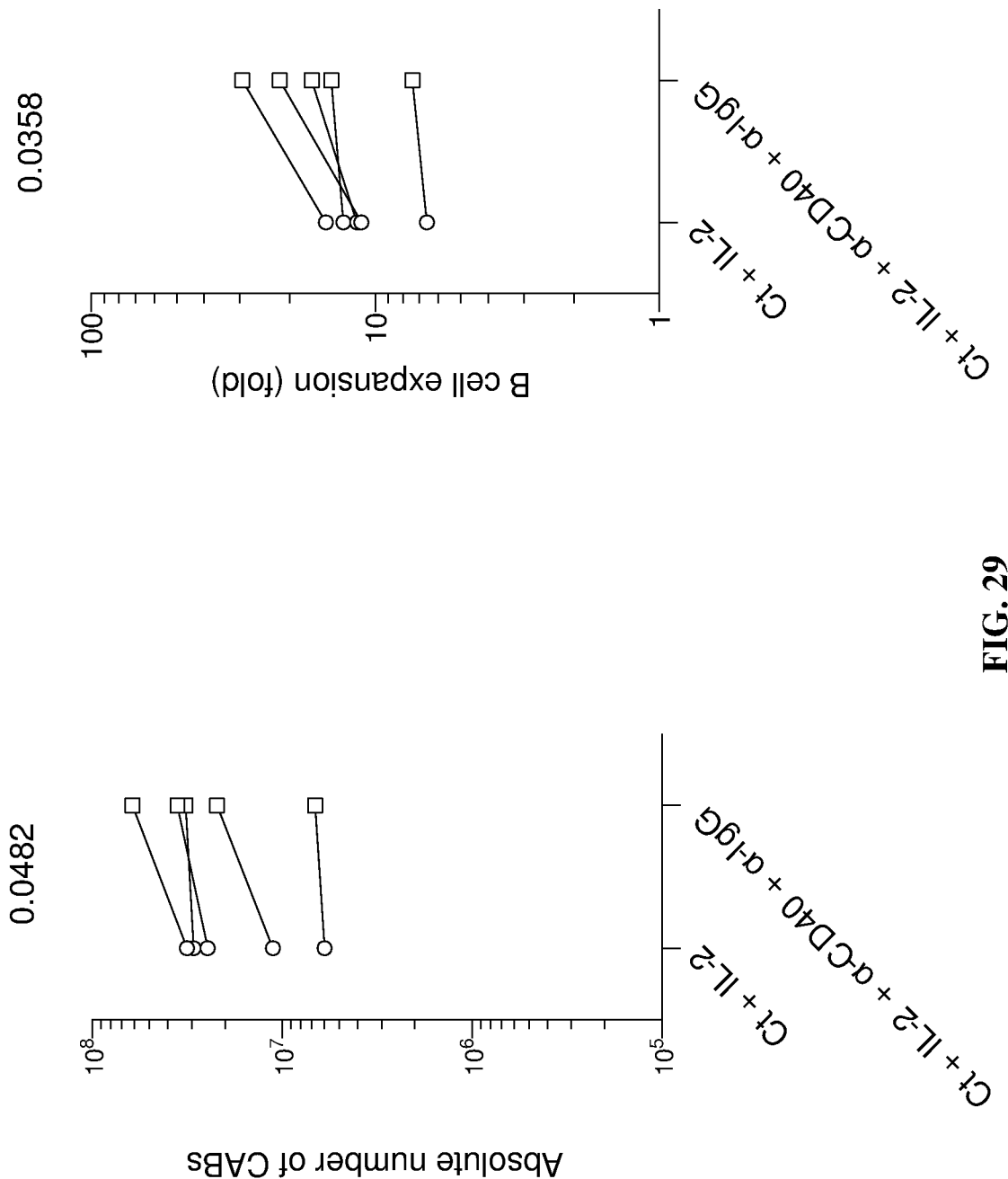
FIG. 29 shows the ability of anti-CD40 mAb to facilitate (i.e., further promote) the generation of human CABs in vitro.

Example 3: Addition of Anti-CD40 Agonist Antibody Increases Ability to Expand Human CABs In Vitro Human peripheral blood mononuclear cells depleted of monocytes by immunomagnetic negative selection are exposed to inactivated *C. trachomatis* serovar L2 RBs in the presence of human recombinant IL-2 and anti-CD40 agonist mAb for a total of 8 days. Using this system, it was found that there was clear synergism between *Chlamydia* and anti-CD40 agonist mAb for the generation of *Chlamydia*-activated B cells, as compared to cells expanded in the absence of this antibody (FIG. 29).

It appears that the addition of anti-CD40 agonist mAb promotes survival of *Chlamydia*-activated B cells, probably by preventing apoptotic cell death, without affecting their ability to prime T cell responses. Therefore, combining *Chlamydia* and anti-CD40 agonist mAb has a synergistic effect in the generation of activated B cells for immunotherapy.

Example 4: Flt-3L and GM-CSF Decrease Tumor Size

In a mouse model of EG.7-OVA tumor, mice were subcutaneously injected with approximately 1.2 million EG.7-OVA cells. 7, 8, and 9 days after this treatment, mice received low dose GM-CSF and Flt-3L. On the day following the third GM-CSF/Flt-3L treatment, mice were administered activated B cells loaded with OVA. It was found that tumor size steadily increased in untreated controls, but tumor size was reduced in mice treated with GM-CSF and Flt-3L (in 40% of these mice the tumor became undetectable). Conversely, tumor growth was uncontrolled in mice treated with GM-CSF/Flt-3L alone after tumor administration.

Figures 4A, 4B:
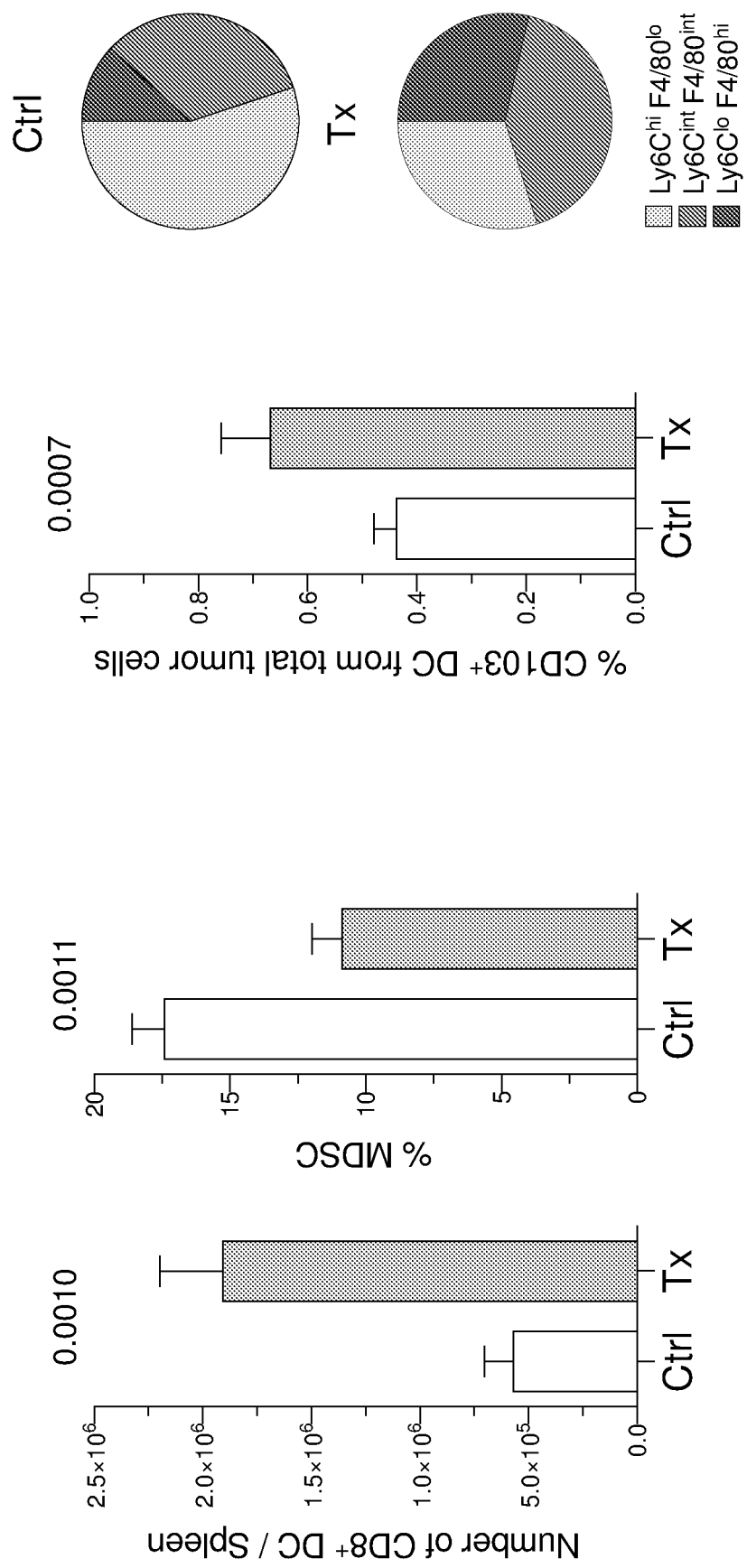
FIG. 4A-B shows that low dose treatment of mice with Flt-3L and GM-CSF increased the number of $CD8^+$ DCs and decreased the proportion of myeloid derived suppressor cells (MDSCs) (A). In addition, treatment increased percentages of $CD8^+CD103^+$ DCs (DCs with the capacity for cross-presentation) and reduced the proportion of immature DCs ($Ly6c^{hi}$) (B). Importantly, Flt-3L and GM-CSF treatment can also improve the efficacy of intervention with other antigen-loaded APCs (e.g. DC-based vaccine platforms), since it increased the frequency of intra-tumoral DCs, increased in vivo antigen-specific T cell priming, decreased myeloid derived suppressor cell frequency, and increased the differentiation of intra-tumoral macrophages.
Figure 5:
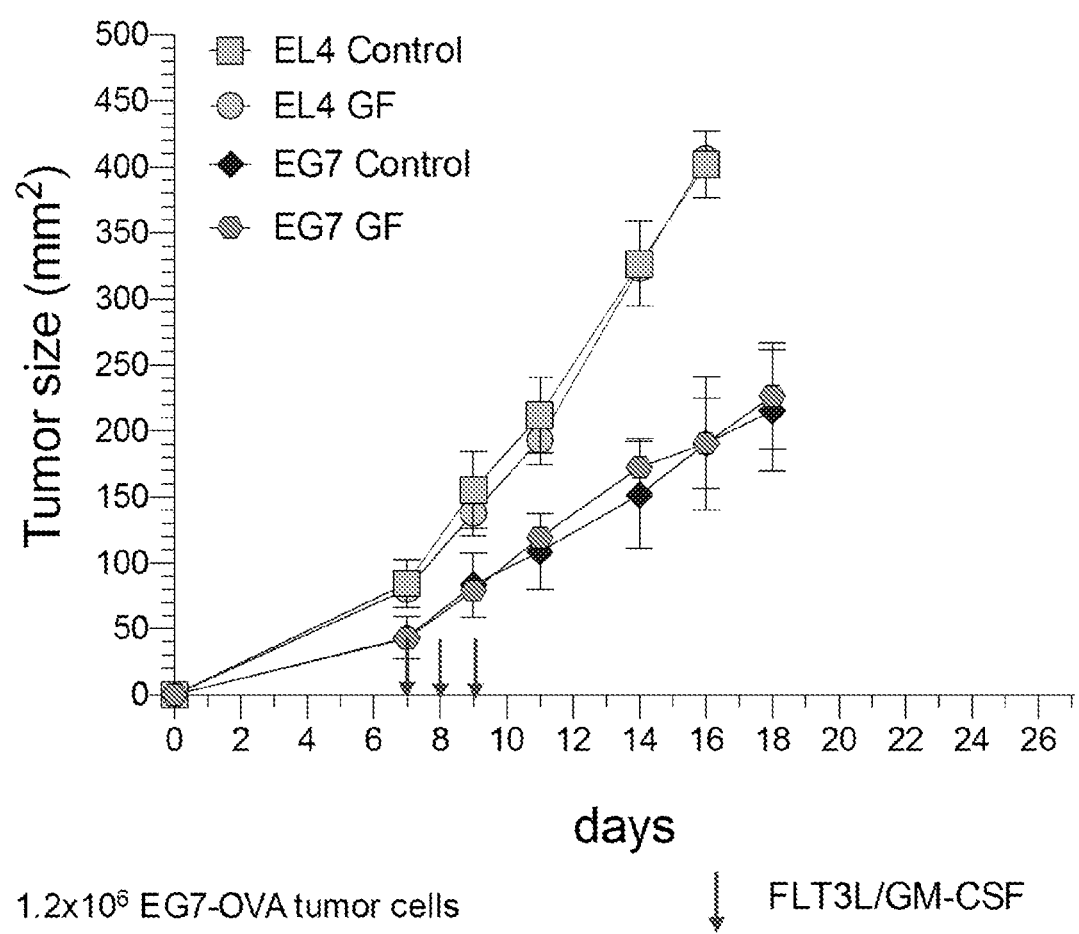
FIG. 5 shows that the increased anti-tumor efficacy of antigen-loaded activated B cells seen with treatment of a tumor-bearing host with Flt-3L and GM-CSF is not a direct anti-tumor effect of Flt-3L and GM-CSF. In figure legend, "GF" denotes treatment with Flt-3L and GM-CSF. As shown, tumor size was reduced in mice treated with GM-CSF and Flt-3L, whereas tumor growth was uncontrolled in mice treated with GM-CSF/Flt-3L alone after tumor administration.
Figure 6:
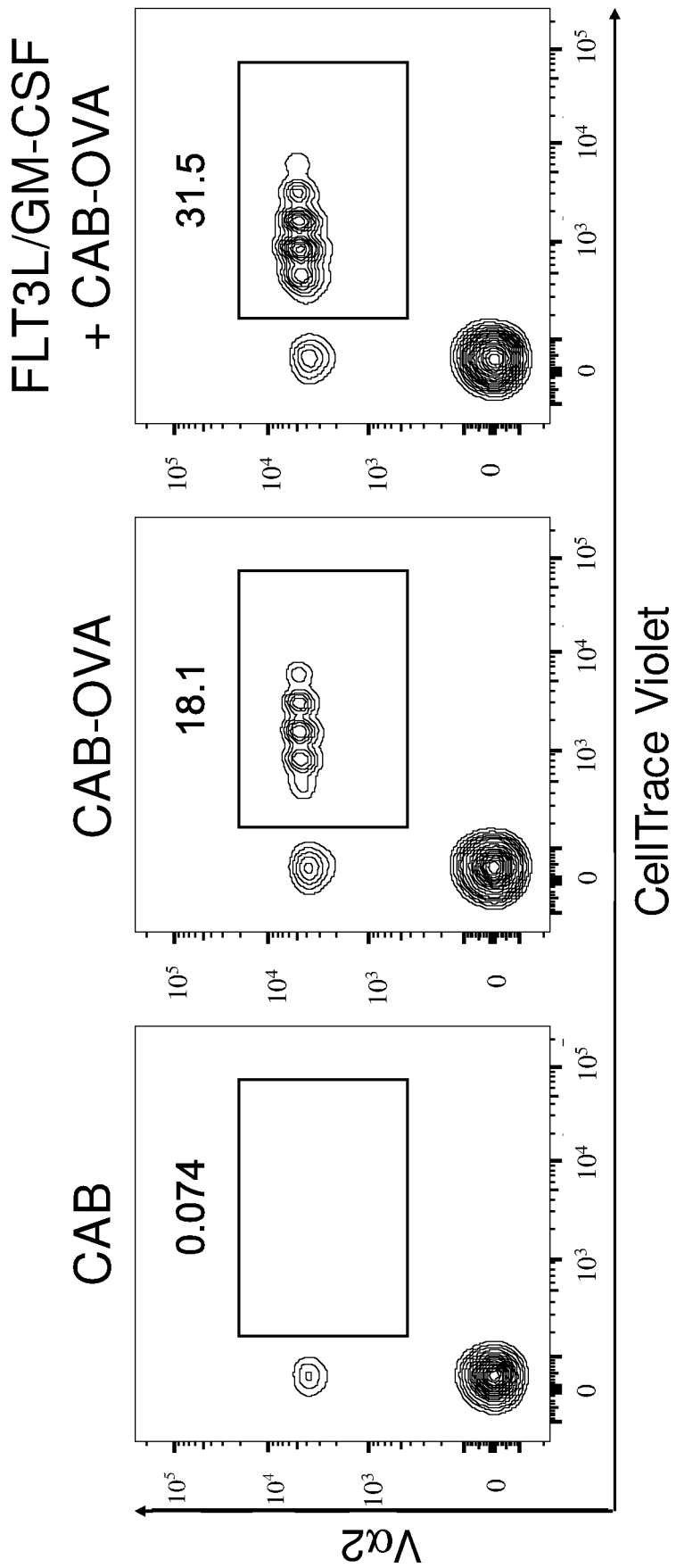
FIG. 6 shows that low dose Flt-3L/GM-CSF improves the ability of activated B cells to prime $CD8^+$ cells. In other words, in vivo $CD8^+$ T cell priming is increased by antecedent treatment with Flt-3L and GM-CSF.

While in this model, GM-CSF/Flt-3L administration improved the efficacy of OVA-loaded B cell treatment, it is important to note that this cytokine treatment can improve the efficacy of intervention with other antigen-loaded antigen presenting cells (e.g. dendritic cell-based vaccine platforms). In support of this, it was found that GM-CSF/Flt-3L administration increased the frequency of intra-tumoral CD103$^+$ dendritic cells (FIG. 2-5), increased in vivo antigen-specific T cell priming (FIG. 6), decreased myeloid derived suppressor cell frequency (FIG. 2-5), and increased the differentiation of intra-tumoral macrophages (FIG. 4).

Figure 10:
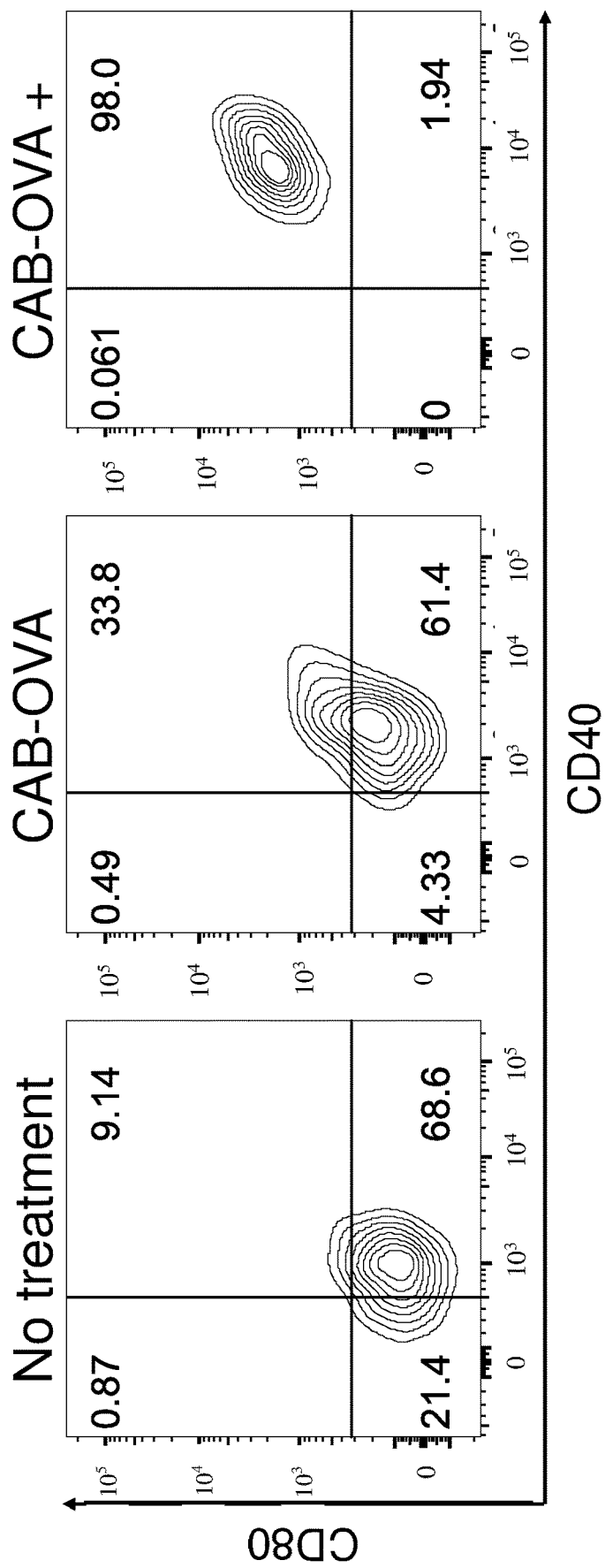
FIG. 10 shows α-GC loading of CABs prior to in vivo administration can dramatically increase activation of endogenous DCs. In addition to GM-CSF and Flt-3L, antigen presenting capabilities of activated B cells (or other professional APCs) are enhanced by in vitro loading of APCs with α-GC prior to in vivo administration.
Figure 10:
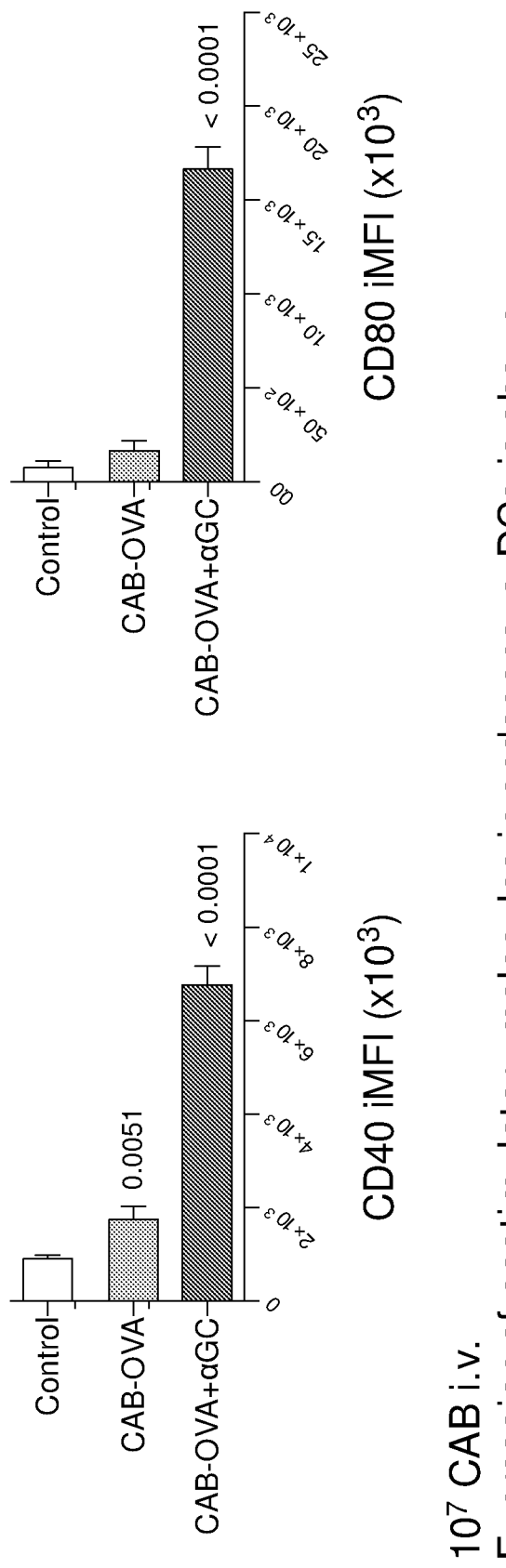
Figure 11:
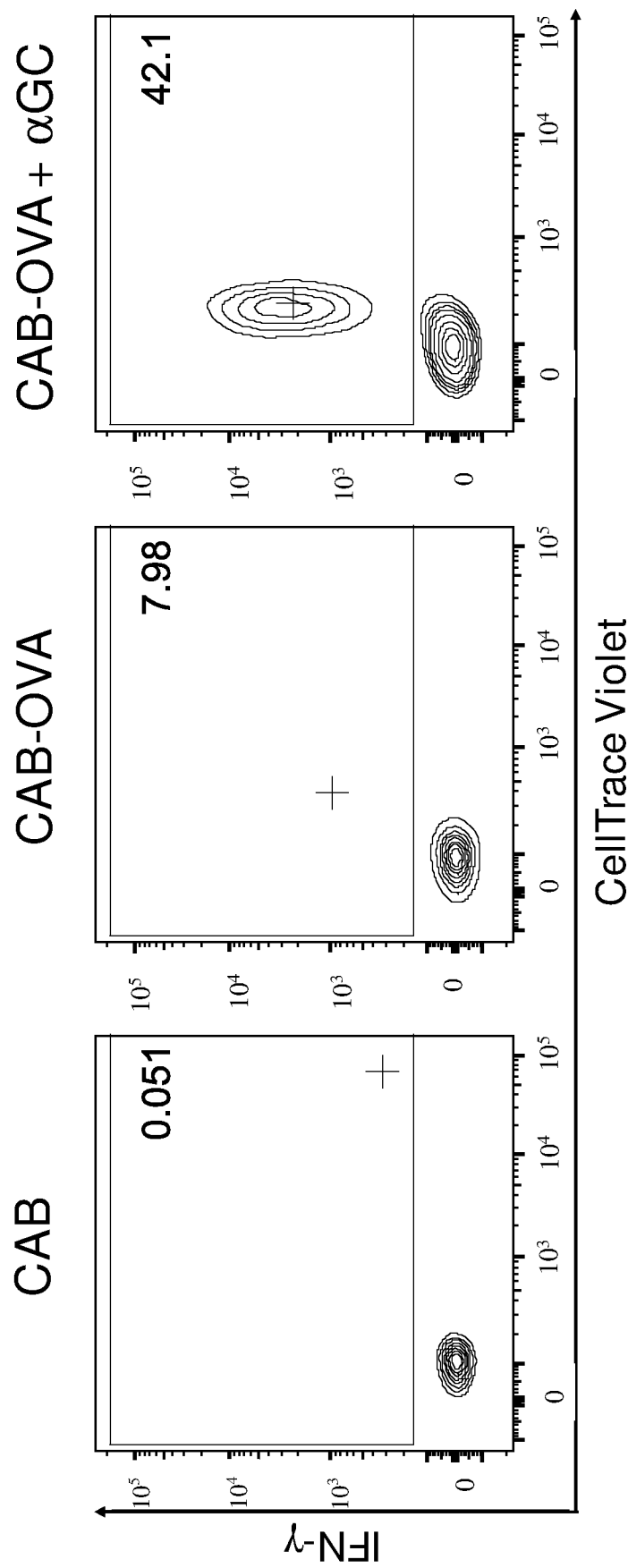
FIG. 11 shows that α-GC-loaded CABs enhance effector function of primed antigen-specific $CD8^+$ T cells.
Figure 12:
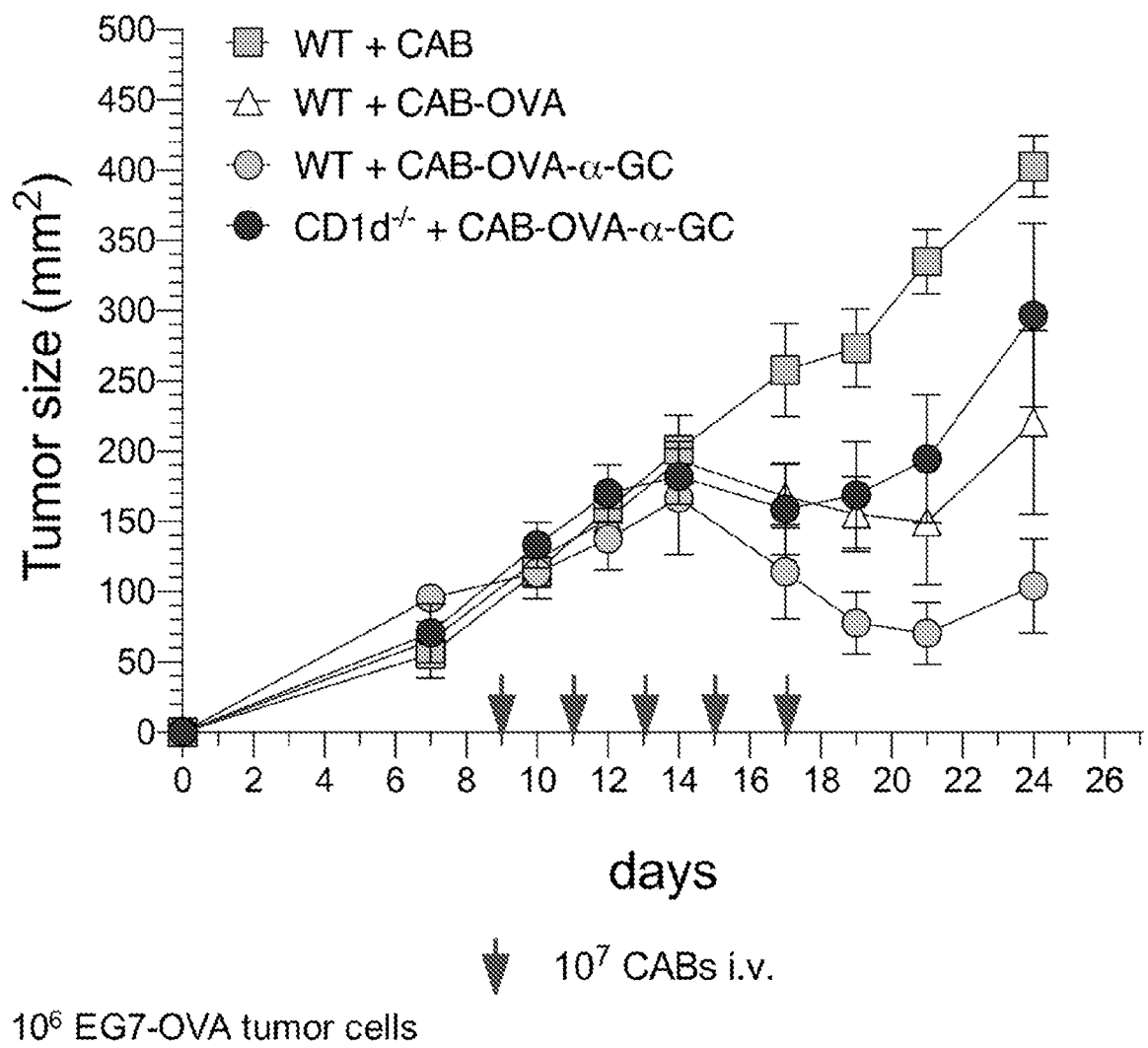
FIG. 12 shows that α-GC loaded activated B cells boost CAB efficacy and more effectively reduce tumor size, and that this effect is dependent on the presence of NKT cells.
Figure 13:
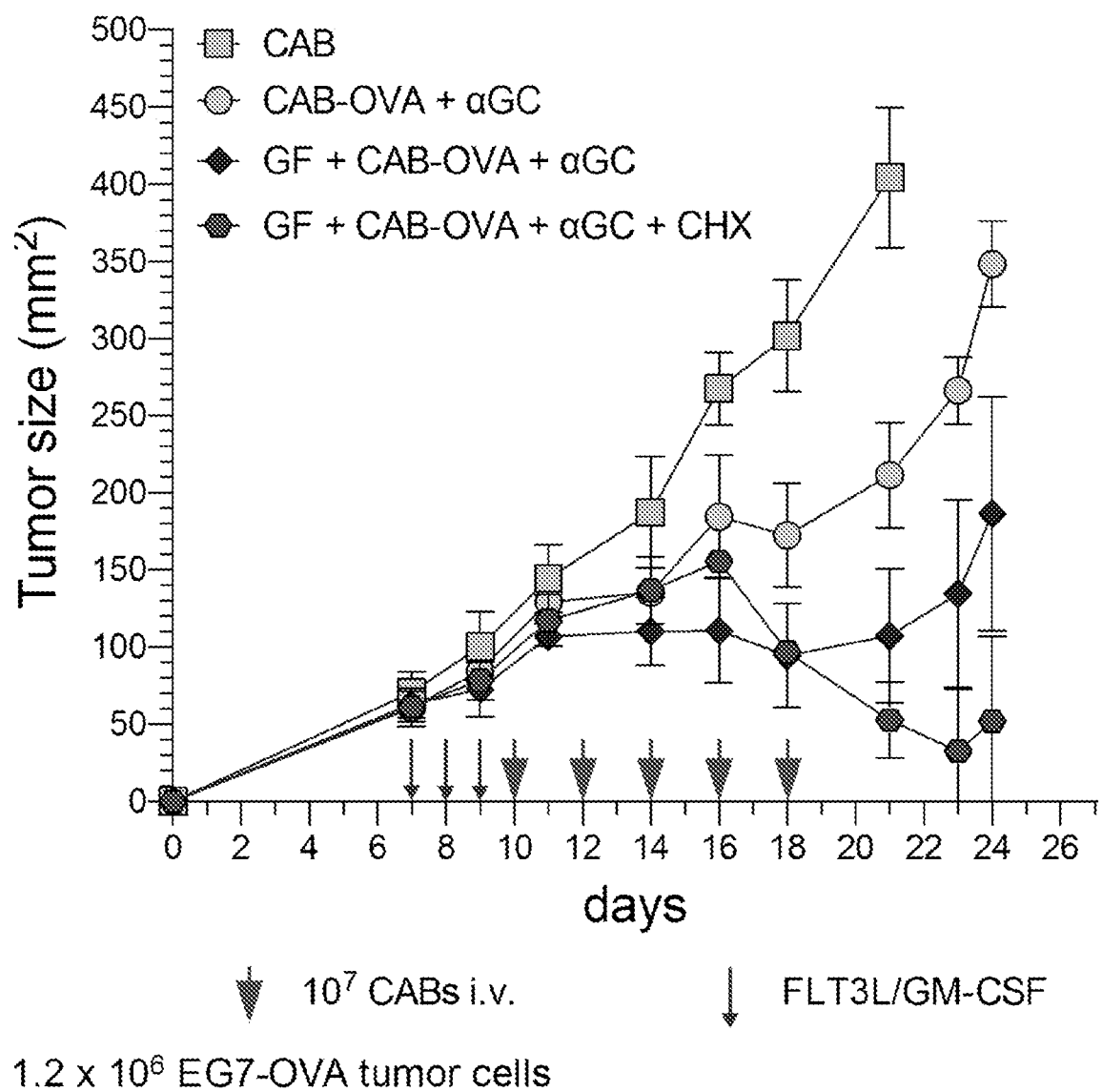
FIG. 13 shows that the entire optimized delivery system provides superior antitumor activity. The strategies described herein increase antigen presenting capacity of activated B cells. They can also be used with other cellular vaccine platforms (e.g., CD40 B cell- and DC-based vaccines) or combined in vivo with checkpoint inhibitors (e.g., anti-PDL1 mAb), for example.
Figure 14:
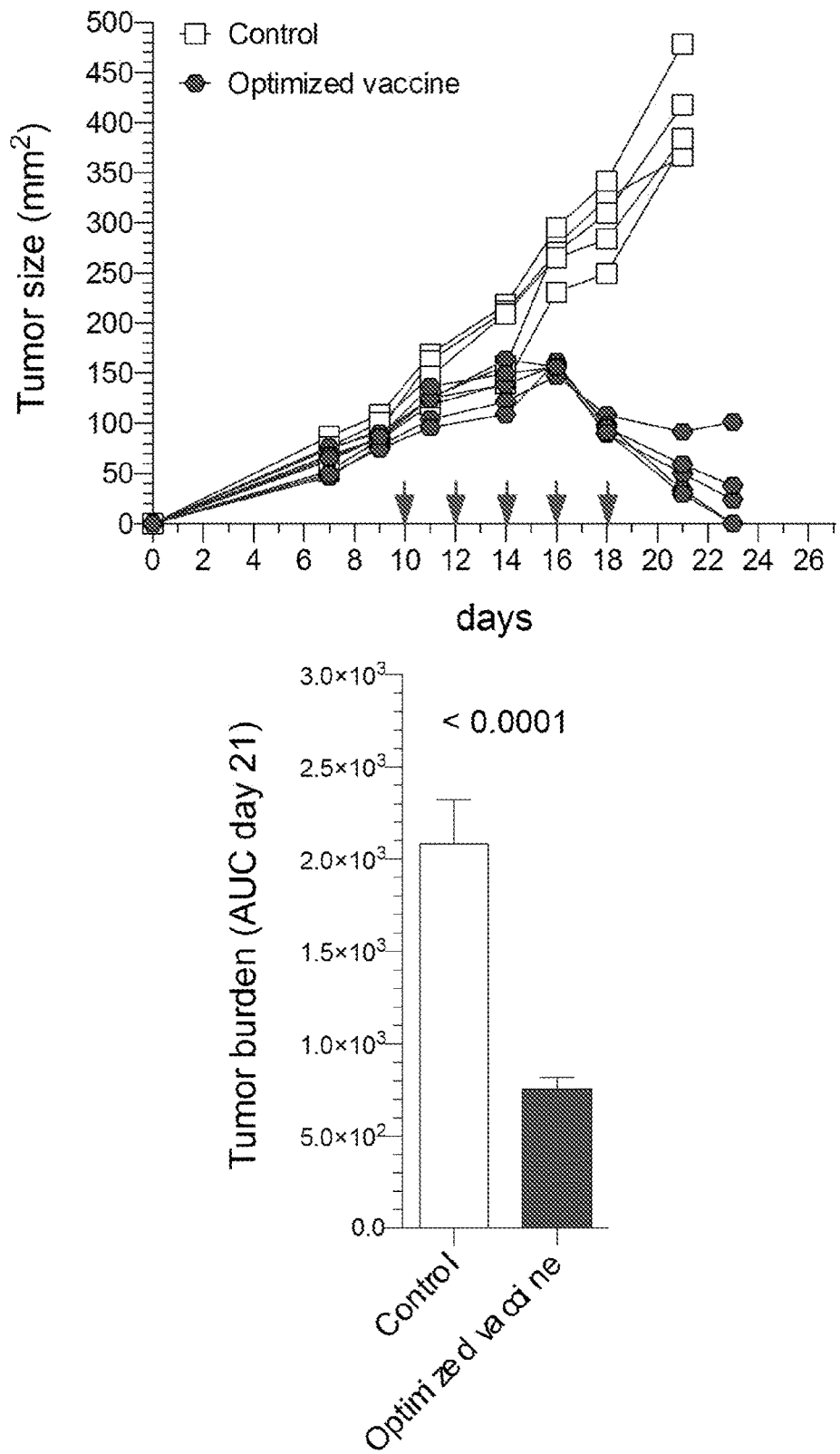
FIG. 14 shows that the optimized delivery system versus a control. Tumor size and tumor burden are reduced. Antecedent injection of low-dose Flt31/GMCSF increases efficacy of CHX-treated, antigen-loaded, α-GC-loaded antigen presenting cells (e.g. activated B cells or mature DCs). Antigen was loaded on antigen presenting cells with EDAC (but other zero-length crosslinking agents could be used).
Figure 15:
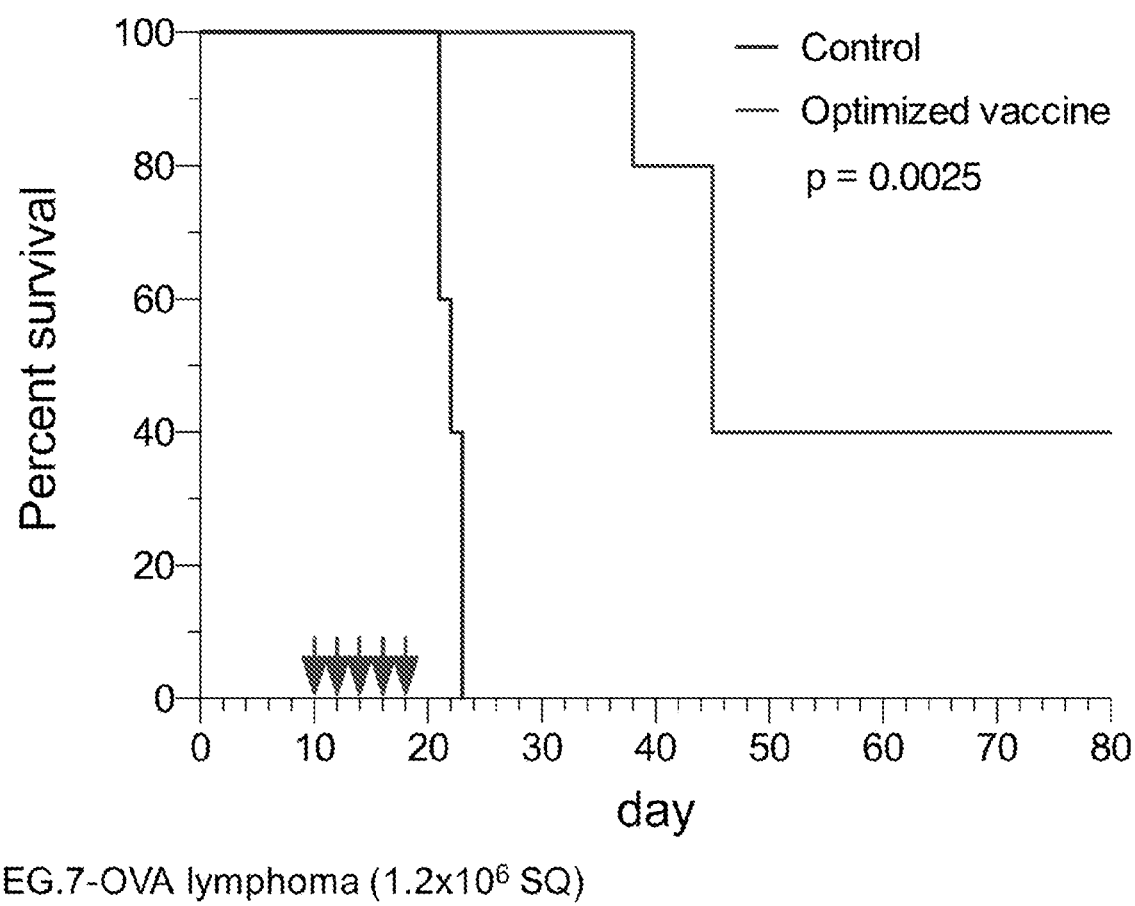
FIG. 15 shows that the optimized delivery system increases survival rates.
Figure 16:
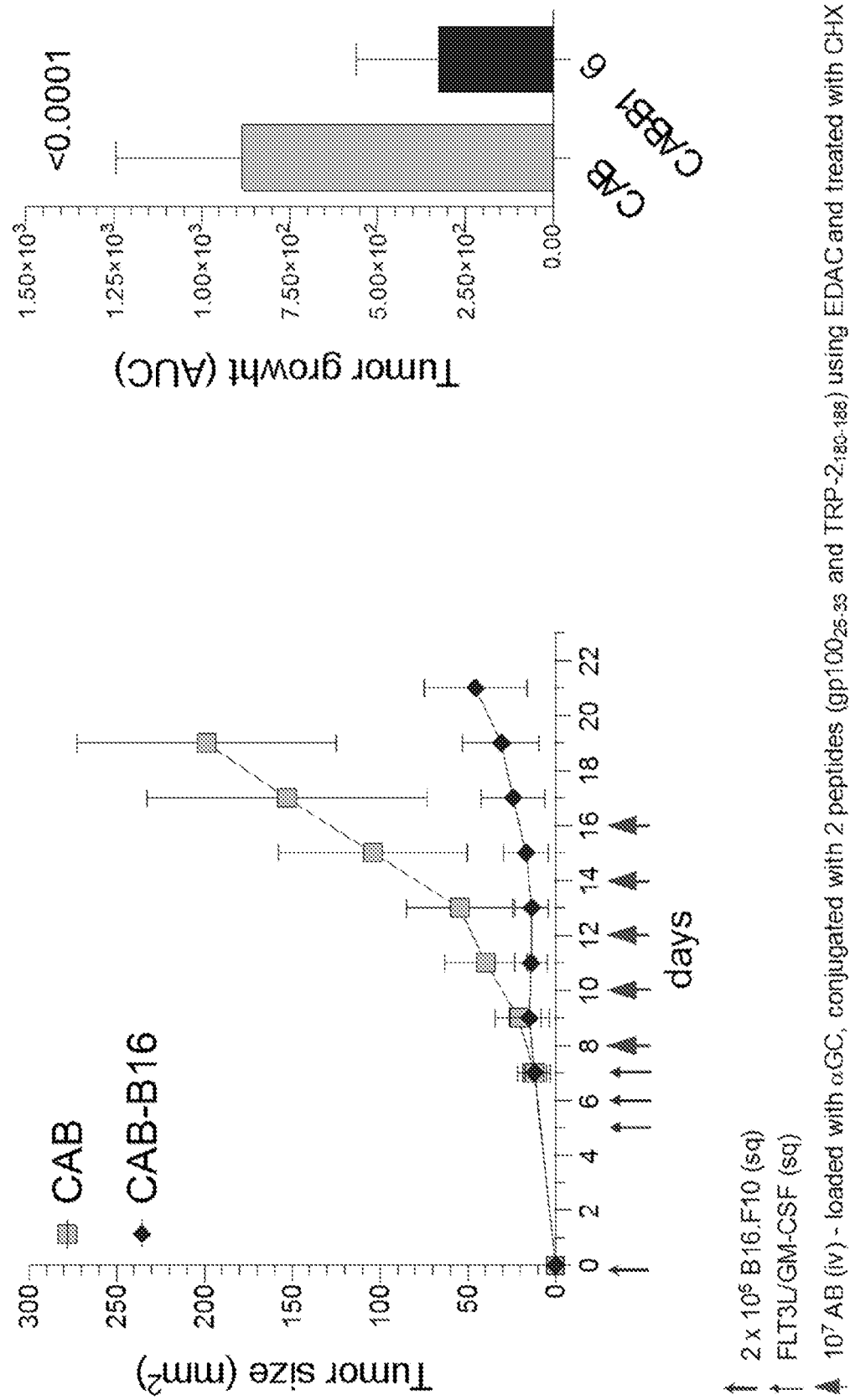
FIG. 16 shows control of B16.F10 melanoma with the optimized delivery system.
Figure 17:
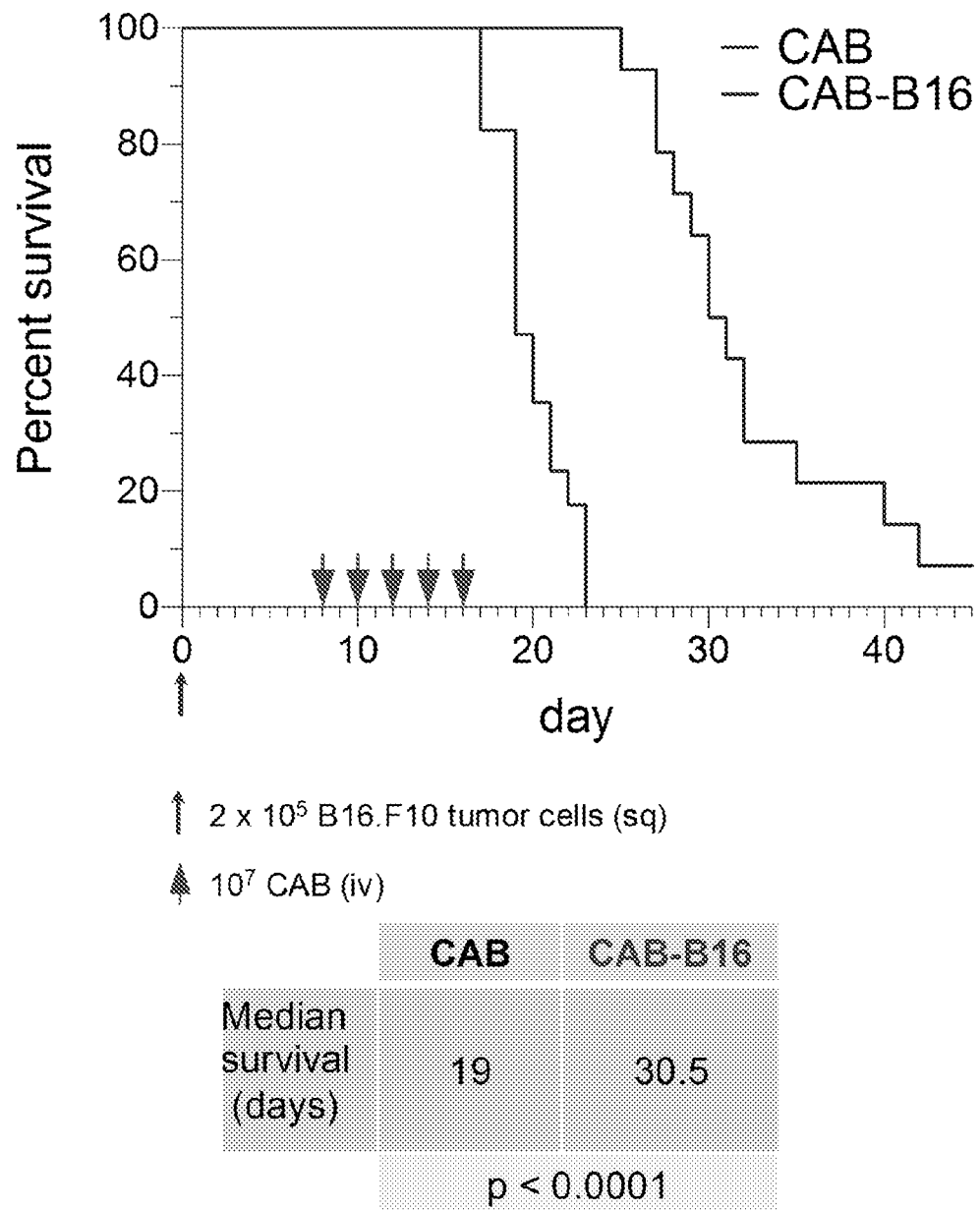
FIG. 17 shows that the optimized delivery system proved efficacious even using the extremely challenging B16.F10 mouse melanoma model, and survival rates were significantly increased.

In addition to novel use of GM-CSF/Flt-3L, it was found that antigen presenting capabilities of activated B cells (or other professional antigen presenting cells) can be enhanced by in vitro loading of α-GalCer and by the use of in vitro crosslinking of cognate antigen prior to in vivo administration of the activated B cells (FIGS. 10-12).

Figure 9:
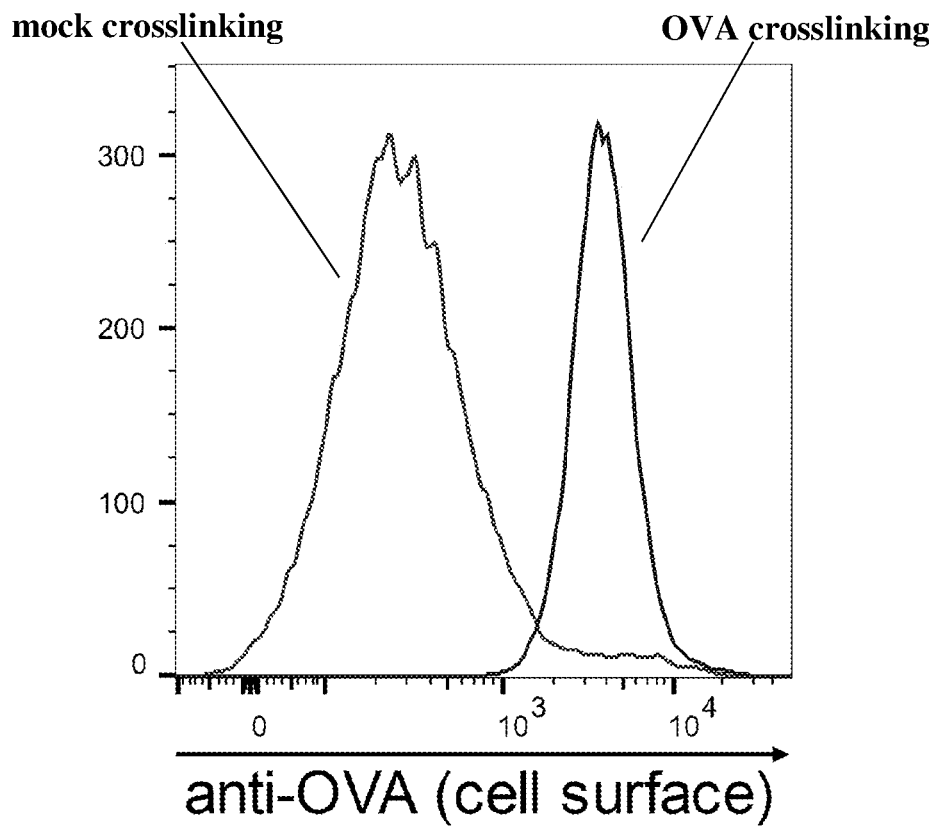
FIG. 9 shows cross-linking of antigen to activated B cells with EDAC. The zero-length cross linker EDAC promotes attachment of amino-containing molecules to activated B cells, such as CABs (*Chlamydia* activated B cells). In the bottom panel, the antigen presenting ability of activated B cells (or other professional APCs) can be enhanced by crosslinking desired antigen (protein or peptide) with EDAC prior to in vivo administration. Chemical conjugation of peptide to CABs using EDAC increases antitumor therapeutic activity compared to simple peptide pulsing/loading CABs.
Figure 9:
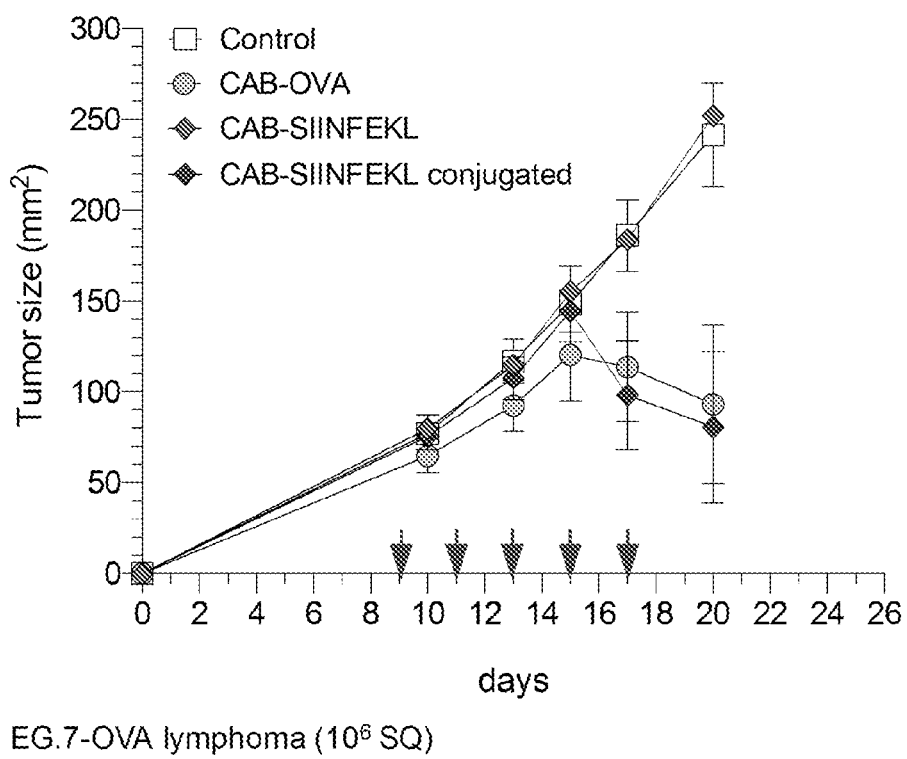
Figure 26:
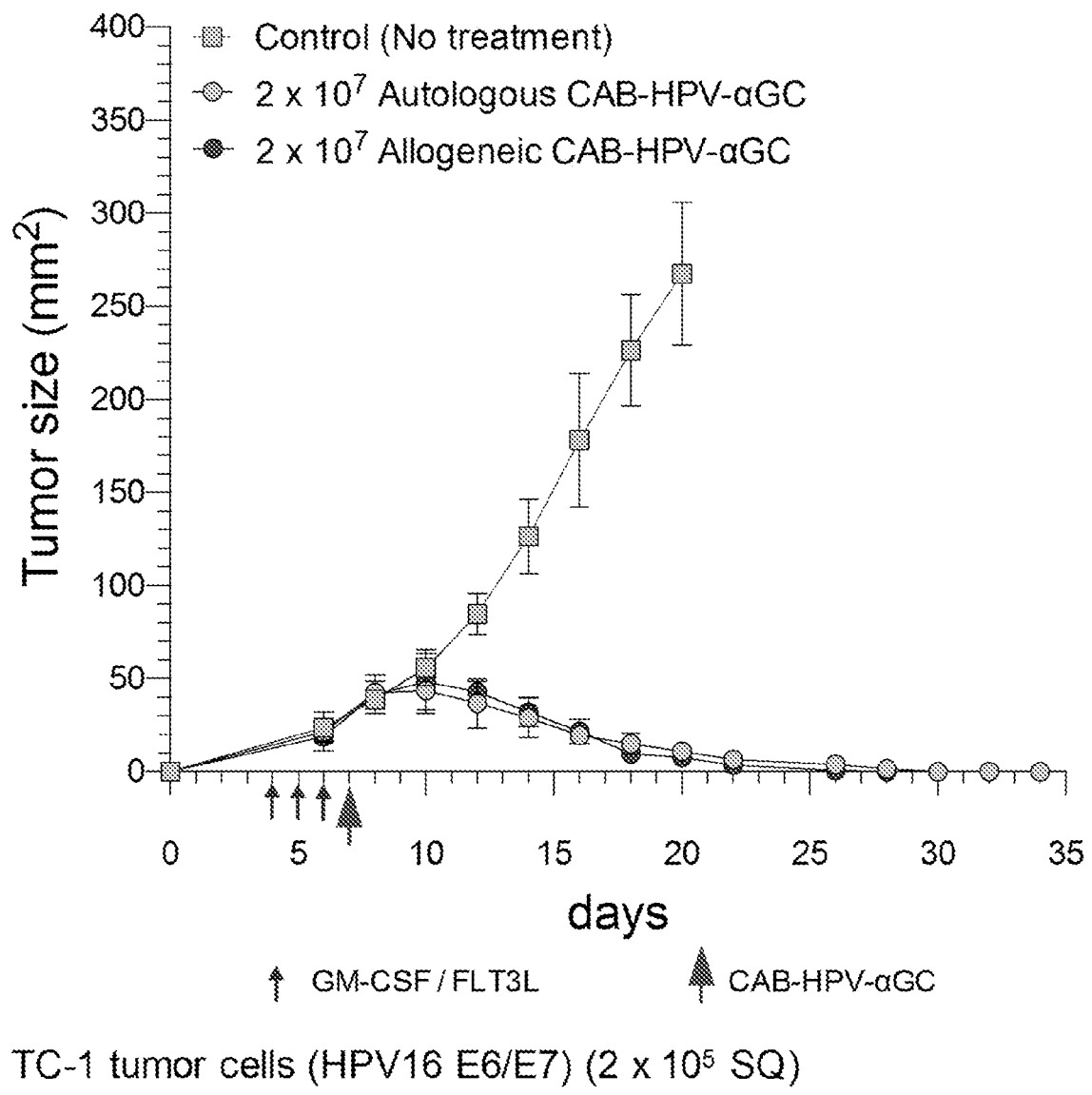
FIG. 26 shows combination of FTY720 and allogeneic CAB therapy significantly increases survival of mice bearing HPV-associated tumors. TC-1 cells (HPV18 E6/E7) were used ($2 \times 10^5$ tumor cells).

It was also found that the antigen presenting capacity of fresh or cryopreserved activated B cells (or other professional APCs) can be enhanced by crosslinking the desired antigen (protein or peptide) using EDAC (FIGS. 9, 24 and 25) prior to in vivo administration. Interestingly, the source of CABs (syngeneic vs allogeneic) did not affect therapeutic activity (FIG. 26).

Figure 8:
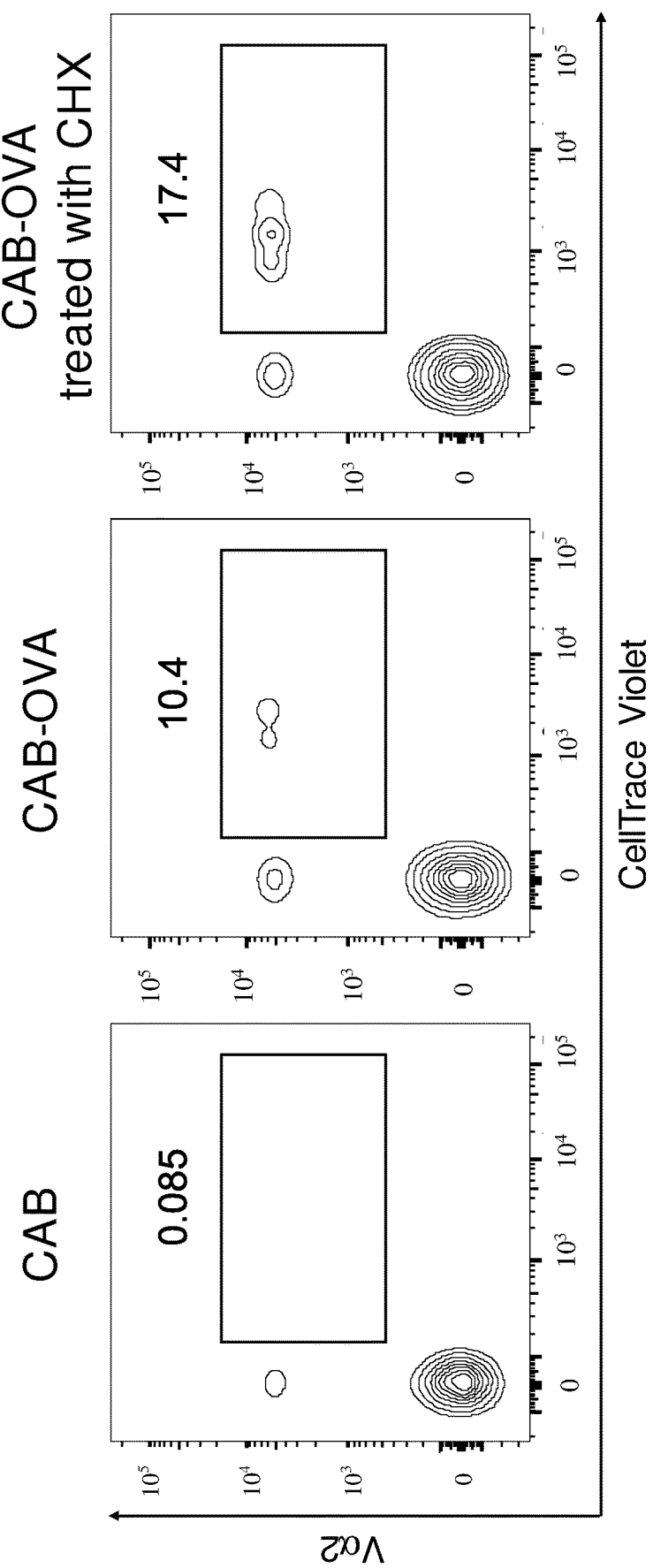
FIG. 8 shows CHX treatment of activated B cells prior to in vivo administration. In vivo $CD8^+$ T cell priming is increased by CHX treatment of activated B cells prior to injection. CHX can boost antigen presenting capacity by increasing survival of activated B cells.

It was also demonstrated in vitro that treatment with CHX can be used to boost antigen presenting capacity (FIG. 8).

Of note, the above strategies shown to increase antigen presenting capacity of activated B cells can also be applied to the use of other cellular vaccine platforms (e.g., CD40- activated B cells, DC-based vaccines, and artificial APCs) and combined in vivo with use of checkpoint inhibitors (e.g., anti-PDL1 mAb).

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize or ascertain using no more than routine experimentation, many equivalents to the specific embodiments of the invention described herein. Such equivalents are intended to be encompassed by the following claims.

What is claimed is:

1. An in vivo platform for enhancing effectiveness of antigen presentation and antigen-specific immune responses, wherein the platform comprises:
    a. a composition comprising at least two cytokines, wherein two of the cytokines are Flt-3L and GM-CSF, wherein Flt-3L is present in an amount to be administered at 8 µg/kg or less; and
    b. a population of antigen presenting cells (APCs) which have been loaded with antigen; wherein the APCs are *Chlamydia*-activated B cells (CABs), and further wherein the antigen is not derived from *Chlamydia* spp.

2. The platform of claim 1, wherein in step b, the APCs are also cross-linked or loaded with adjuvant.

3. The platform of claim 1, wherein the population of APCs which have been loaded with antigen present the loaded antigen to endogenous immune cells.

4. The platform of claim 1, wherein the endogenous immune cells include APCs.

5. The platform of claim 1, wherein the antigen is a protein, peptide, or any amine-containing molecule.

6. The platform of claim 5, wherein the protein or peptide is cross-linked to an antigen presenting cell with (1-ethyl-3-(3-dimethylaminopropyl) carbodiimide hydrochloride (EDAC) or an equivalent adjuvant.

7. The platform of claim 1, wherein the APCs are treated with cycloheximide (CHX) or a comparable adjuvant prior to being cross-linked with antigen.

8. The platform of claim 1, wherein the APCs are exposed to α-galactosylceramide (α-GalCer) or a comparable adjuvant.

9. The platform of claim 1, wherein the APCs are exposed to FTY720 or a comparable adjuvant.

10. The platform of claim 1, wherein the platform comprises more than one antigen.

11. The platform of claim 1, wherein the antigen comprises a tumor-related antigen or a viral-related tumor antigen.

12. The platform of claim 1, wherein the antigen comprises one or more components of an infectious agent.

13. The platform of claim 1, wherein GM-CSF is present in an amount to be administered of 2 µg/kg or less.

14. The platform of claim 1, wherein GM-CSF is present in an amount of be administered at a range of 0.5 to 2.0 µg/kg or less.

15. The platform of claim 1, wherein Flt-3L is present in an amount to be administered at a range of 2.0 to 8.0 µg/kg or less.

16. The platform of claim 9, wherein FTY720 is present in an amount to be administered at range of 50 µg/kg or less.

17. A vaccine created using the platform of claim 1.

18. A vaccine created using the platform of claim 9.

* * * * *